US012064200B2

(12) United States Patent
Song et al.

(10) Patent No.: US 12,064,200 B2
(45) Date of Patent: Aug. 20, 2024

(54) SURGICAL ROBOT ARM

(71) Applicant: LIVSMED INC., Seongnam-si (KR)

(72) Inventors: Youngjae Song, Seongnam-si (KR);
Jung Joo Lee, Seongnam-si (KR);
Heejin Kim, Seongnam-si (KR);
Dongkyu Jang, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

(21) Appl. No.: 18/432,754

(22) Filed: Feb. 5, 2024

(65) Prior Publication Data

US 2024/0173086 A1    May 30, 2024

Related U.S. Application Data

(63) Continuation of application No. PCT/KR2022/011624, filed on Aug. 5, 2022.

(30) Foreign Application Priority Data

| Aug. 6, 2021 | (KR) | 10-2021-0104224 |
| Aug. 27, 2021 | (KR) | 10-2021-0114303 |
| Sep. 17, 2021 | (KR) | 10-2021-0125316 |
| Sep. 24, 2021 | (KR) | 10-2021-0126775 |

(51) Int. Cl.
*G05B 1/02* (2006.01)
*A61B 34/30* (2016.01)

(52) U.S. Cl.
CPC ........ *A61B 34/30* (2016.02); *A61B 2034/301* (2016.02); *A61B 2034/305* (2016.02)

(58) Field of Classification Search
CPC ......... A61B 34/35; A61B 34/37; A61B 34/74; A61B 34/71; A61B 2090/066; A61B 2034/305; A61B 17/29; A61B 34/30; A61B 2090/064; A61B 2034/2059; A61B 2034/3011; A61B 1/0057; A61B 1/018; A61B 1/0011; A61B 1/0055; A61B 2017/00309; A61B 2017/00526; A61B 2034/303; A61B 1/008; A61B 2017/2906; A61B 2017/00323; A61B 2034/301;
(Continued)

(56) References Cited

U.S. PATENT DOCUMENTS 8,126,114 B2    2/2012  Naylor et al.
9,717,563 B2 *  8/2017  Tognaccini .............. A61B 1/04
(Continued)

FOREIGN PATENT DOCUMENTS

CN    109998685 A     7/2019
EP      2537483 A2    12/2012
(Continued)

OTHER PUBLICATIONS

Roh et al., Development of the SAIT single-port surgical access robot slave arm based on RCM Mechanism, 2015, IEEE, p. 5285-5290 (Year: 2015).*

(Continued)

*Primary Examiner* — McDieunel Marc
(74) *Attorney, Agent, or Firm* — Bridgeway IP Law Group, PLLC; Sang Ho Lee; Hyun Woo Shin

(57) ABSTRACT

Provided is a surgical robot arm, and more particularly, to a minimally invasive surgical robot arm that is formed in a modular manner for use in a laparoscopic surgery or other various surgeries.

30 Claims, 69 Drawing Sheets

(58) Field of Classification Search
CPC ..... A61B 2017/003149; B25J 15/0028; G02B 23/2476
See application file for complete search history.

(56) References Cited

U.S. PATENT DOCUMENTS

| | | | | |
|---|---|---|---|---|
| 10,130,366 | B2* | 11/2018 | Shelton, IV | A61B 17/072 |
| 10,154,822 | B2* | 12/2018 | Henderson | B25J 9/1674 |
| 10,245,069 | B2* | 4/2019 | Rogers | A61B 1/313 |
| 10,258,425 | B2* | 4/2019 | Mustufa | A61B 34/37 |
| 10,307,199 | B2* | 6/2019 | Farritor | A61B 18/00 |
| 10,716,636 | B2* | 7/2020 | Radgowski | A61B 34/30 |
| 11,413,428 | B2* | 8/2022 | Yu | A61B 1/00133 |
| 11,786,328 | B2* | 10/2023 | Deane | A61B 34/35 606/205 |
| 2023/0165644 | A1* | 6/2023 | Deane | A61B 1/0016 700/245 |
| 2023/0172680 | A1* | 6/2023 | Reid | A61B 34/71 606/1 |
| 2023/0233275 | A1* | 7/2023 | Veitch | A61B 34/70 606/1 |

FOREIGN PATENT DOCUMENTS

| | | |
|---|---|---|
| KR | 10-2017-0091588 A | 8/2017 |
| KR | 10-2186365 B1 | 12/2020 |
| WO | 2020-120901 A1 | 6/2020 |

OTHER PUBLICATIONS

Darbemamieh et al., Design and analysis of a mechanism for enhanced flexibility in minimally invasive surgical instruments, 2010, IEEE, p. 90-93 (Year: 2010).*

Li et al., Development of a novel mechanism for minimally invasive surgery, 2010, IEEE, p. 1370-1375 (Year: 2010).*

Degirmenci et al., Design and control of a parallel linkage wrist for robotic microsurgery, 2015, IEEE, p. 222-228 (Year: 2015).*

* cited by examiner

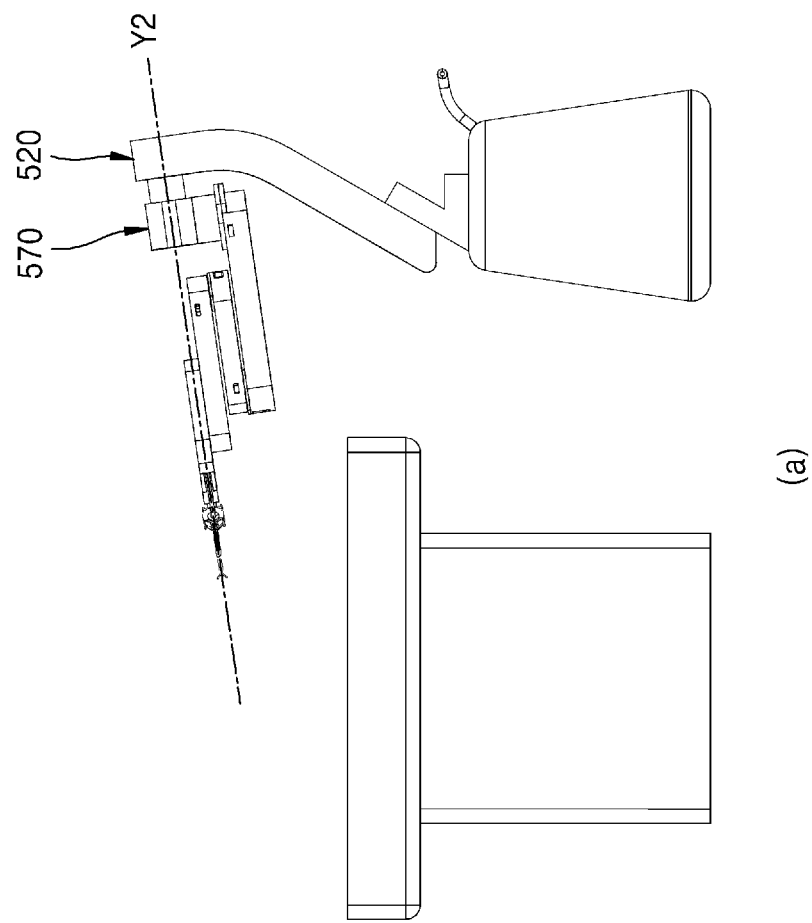
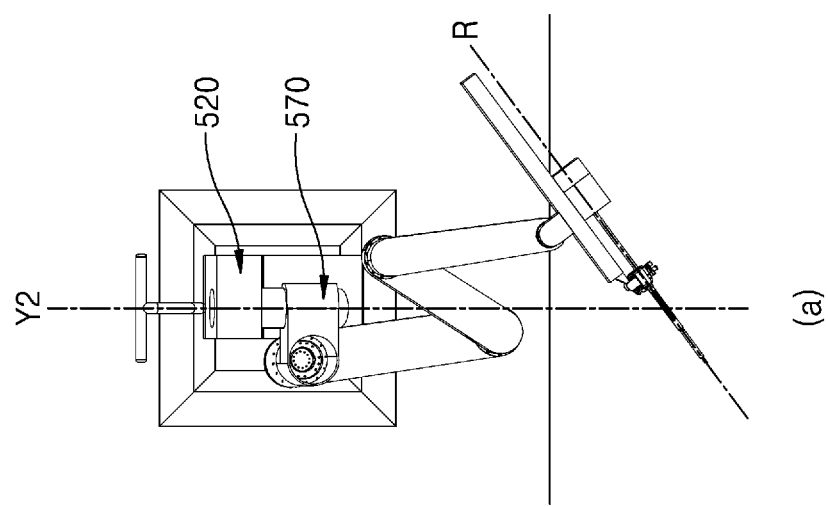
FIG. 20

FIG. 45
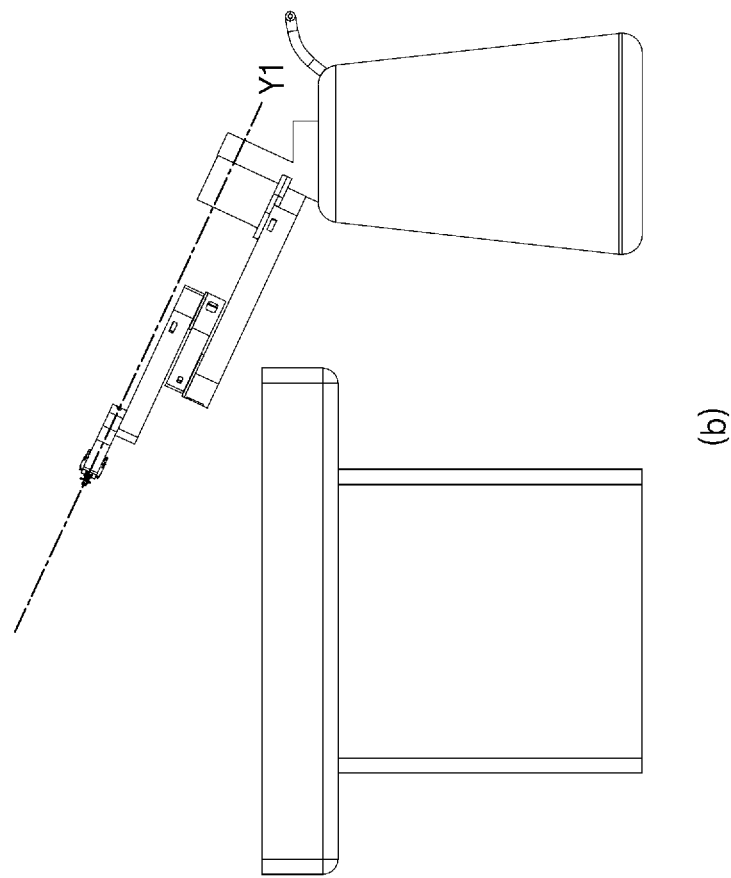
(b)
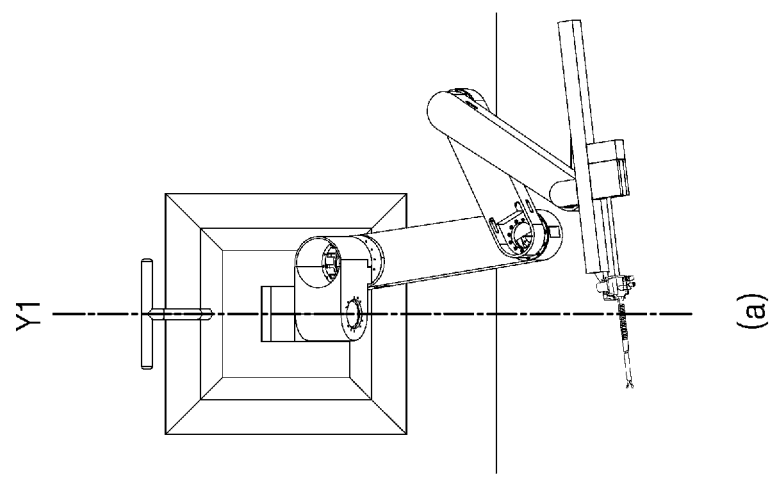
(a)

SURGICAL ROBOT ARM

CROSS-REFERENCE TO RELATED APPLICATION(S)

This application is a continuation of international application No. PCT/KR2022/011624, filed on Aug. 5, 2022, which claims priority to Korean Patent Application No. 10-2021-0104224, filed on Aug. 6, 2021, Korean Patent Application No. 10-2021-0114303, filed on Aug. 27, 2021, Korean Patent Application No. 10-2021-0125316, filed on Sep. 17, 2021, and Korean Patent Application No. 10-2021-0126775, filed on Sep. 24, 2021, with the Korean Intellectual Property Office, the disclosures of which are incorporated herein in their entirety by reference.

TECHNICAL FIELD

The present disclosure relates to a surgical robot arm, and more particularly, to a minimally invasive surgical robot arm that is formed in a modular manner for use in a laparoscopic surgery or other various surgeries.

BACKGROUND ART

Medically, surgery refers to the treatment of diseases by cutting, slitting, or manipulating the skin, mucous membranes, or other tissues using medical devices In particular, open surgery in which the skin of the surgical site is incised and opened to treat, shape, remove organs or the like therein and the like cause problems such as bleeding, side effects, patient pain, scarring. Accordingly, recently, surgery performed by inserting only a medical device, for example, laparoscopic surgical instrument, microsurgical microscope, and the like by forming a predetermined hole in the skin or surgery using a robot has been spotlighted as an alternative.

Here, a surgical robot refers to a robot that has a function of replacing a surgical action performed by a surgeon. Advantageously, the surgical robot may operate more accurately and precisely as compared with a human and enable remote operation.

Surgical robots that are currently being developed worldwide may include a bone surgical robot, a laparoscopic surgical robot, a stereotactic surgical robot, and the like. Here, the laparoscopic surgical robot is a robot that performs minimum invasive surgery using a laparoscope and small surgical instruments.

Laparoscopic surgery is a cutting-edge surgery technique that involves perforating a small hole in the abdomen and inserting a laparoscope, which is an endoscope for looking inside the abdomen to perform the surgery, and is a field that is expected to advance in the future. Today's laparoscopes are mounted with computer chips and have been developed to the extent that magnified images, which are clearer than images seen with the naked eye, can be obtained and when used with specially-designed laparoscopic surgical tools while looking at a monitor screen, any type of surgery is possible.

Moreover, laparoscopic surgery offers the same range of surgical procedures as open surgery, but with several advantages including fewer complications, the ability to initiate treatment shortly after the procedure, and the capability to maintain the patient's stamina and immune functions. As a result, laparoscopic surgery is becoming increasingly recognized as the standard surgery for treating colorectal cancer or the like in places such as the United States and Europe.

Meanwhile, a surgical robot is generally composed of a master robot and a slave robot. When a surgical operator manipulates a control lever (e.g., a handle) equipped on the master robot, a surgical tool coupled to or held by a robot arm on the slave robot may be manipulated to perform surgery.

The background art described above is technical information retained by the present inventors in order to derive the present disclosure or obtained by the present inventors in the process of deriving the present disclosure, and thus is not necessarily known art disclosed to the general public before the filing of the present application.

DESCRIPTION OF EMBODIMENTS

Technical Problem

The present disclosure is directed to providing a surgical robot arm allowing a surgical instrument to be disposed in a horizontal direction without inducing a gimbal lock phenomenon by forming a first yaw axis Y1 and an extension line connecting a third joint to a remote center of motion (RCM) to be different each other.

Solution to Problem

One aspect of the present invention provides a surgical robot arm to which a surgical instrument is mounted, the surgical robot arm including a body, a base link formed on one surface of the body, a yaw drive assembly coupled to the base link by a first joint and formed to be yaw rotatable around a first yaw axis with respect to the base link, a third link axially coupled to the yaw drive assembly so as to be rotatable around a third joint with respect to the yaw drive assembly, a fourth link axially coupled to the third link so as to be rotatable around a fourth joint with respect to the third link, and a fifth link axially coupled to the fourth link so as to be rotatable around a fifth joint with respect to the fourth link, and formed to allow the surgical instrument to be mounted thereto, wherein a remote center of motion (RCM) is formed at the remaining vertex of a parallelogram with the third joint, the fourth joint, and the fifth joint constituting vertices, and the first yaw axis and an extension line connecting the third joint to the RCM are formed to be different from each other.

Advantageous Effects of Disclosure

According to the present disclosure, by forming a first yaw axis and an extension line connecting a third joint to a remote center of motion (RCM) to be different from each other, a fifth link and a surgical instrument coupled thereto can be disposed in a horizontal direction without inducing a gimbal lock phenomenon. Furthermore, the surgical instrument can be disposed facing upward from below, beyond the horizontal direction. In addition, by disposing each of links to be offset by a certain degree, a rotational motion of each link is not constrained by another link, so that the range of motion of the instrument can be increased, such as a moving direction of the instrument is directed upward beyond the horizontal direction. Accordingly, even in the frequent case of surgery, in which the instrument is disposed in the horizontal direction, an effect of preventing gimbal lock and allowing the instrument to move with a sufficient range of motion can be obtained.

BRIEF DESCRIPTION OF DRAWINGS

FIG. 20 is a set of a plan view and a side view illustrating a state in which the surgical robot arm in FIG. 19B rotates further around the second yaw axis Y2 by approximately 90°.

FIG. 45 is a set of a plan view and a side view illustrating a state in which the surgical robot arm in FIG. 32 rotates further around the first yaw axis Y1 by approximately 90°.

BEST MODE

Figure 1:
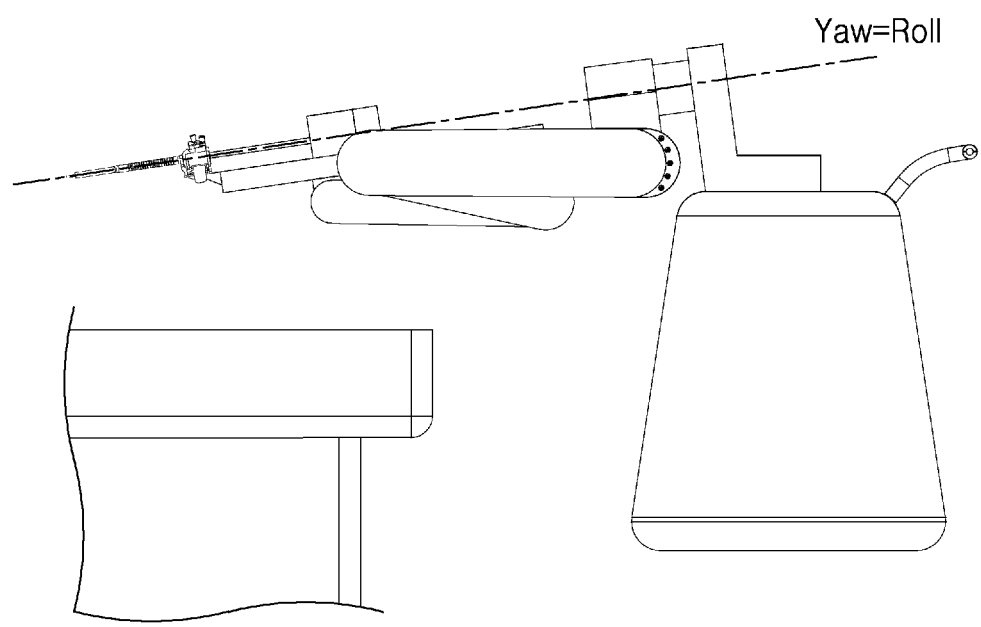
FIG. 1 is a view illustrating a surgical robot arm.

In the present disclosure, the first yaw axis and the extension line connecting the third joint to the RCM may be formed to form a predetermined angle rather than being parallel to each other.

In the present disclosure, the RCM may be positioned on an extension line of the first yaw axis.

In the present disclosure, when the third link rotates around the third joint, the third link and the fifth link rotate while maintaining a parallel state, and the fourth link and the extension line connecting the third joint to the RCM rotate while maintaining a parallel state.

In the present disclosure, the RCM may remain constant in position regardless of the rotation of the third link.

In the present disclosure, the third link and the fifth link may maintain a parallel state in any state of motion of the surgical robot arm, and the fourth link and the extension line connecting the third joint to the RCM may maintain a parallel state in any state of motion of the surgical robot arm.

In the present disclosure, a height of the RCM in a Z-axis direction may be formed to be greater than a height of a point of the base link, through which the first yaw axis passes, in the Z-axis direction.

In the present disclosure, the yaw drive assembly may further include a first link coupled to the base link by the first joint and formed to be yaw rotatable around the first yaw axis with respect to the base link, a sixth link coupled to the first link by a sixth joint and formed to be yaw rotatable around a second yaw axis with respect to the first link, and a second link having one end portion fixedly coupled to the sixth link and another end portion coupled to the third link.

In the present disclosure, the RCM may be positioned on an extension line of the second yaw axis.

In the present disclosure, an extension line of the first yaw axis and an extension line of the second yaw axis may intersect at the RCM.

In the present disclosure, the first link formed to be yaw rotatable around the first yaw axis and the sixth link formed to be yaw rotatable around the second yaw axis may be formed to be rotatable independently of each other.

In the present disclosure, when a roll axis of the surgical instrument is parallel to the first yaw axis, a yaw motion may be performed by rotation of the second yaw axis.

In the present disclosure, when a roll axis of the surgical instrument is parallel to the second yaw axis, a yaw motion may be performed by rotation of the first yaw axis.

In the present disclosure, the yaw drive assembly may further include a first link coupled to the base link by the first joint and formed to be yaw rotatable around the first yaw axis with respect to the base link, and a second link having one end portion fixedly coupled to the first link and another end portion coupled to the third link.

In the present disclosure, the second link may be formed parallel to the extension line connecting the third joint to the RCM.

In the present disclosure, the second link and the fourth link may be formed parallel to each other.

In the present disclosure, the second link may be formed to be inclined with respect to the extension line connecting the third joint to the RCM.

In the present disclosure, the second link the fourth link may be formed to form a predetermined angle rather than being parallel to each other.

In the present disclosure, the surgical robot arm may further include a setup link assembly formed between the body and the base link and configured to connect the body to the base link.

In the present disclosure, the setup link assembly may include a vertical setup link configured to connect the body to the base link and formed to be movable in a Z-axis direction with respect to the body.

In the present disclosure, the setup link assembly may include one or more horizontal setup links configured to connect the body to the base link and formed to be rotatable around a Z-axis with respect to the body.

In the present disclosure, the setup link assembly may include a pitch positioning joint configured to connect the body to the base link, and formed to be rotatable relative to the base link around an axis that is substantially parallel to a rotation axis of the third joint.

In the present disclosure, the setup link assembly may be formed to be operable only during a setup period in which the surgical robot arm is disposed at an appropriate position on one side of a patient.

In the present disclosure, each of the third link, the fourth link, and the fifth link may be formed to be offset by a certain degree in a direction of a rotation axis thereof.

In the present disclosure, based on a direction of a rotation axis of the third link, the fourth link may be disposed on one side of the third link, and the fifth link may be disposed on one side of the fourth link.

In the present disclosure, based on a direction of the first yaw axis, at least a portion of each of the third link, the fourth link, and the fifth link can overlap each other.

In the present disclosure, in a state in which the surgical instrument coupled to the fifth link is horizontal and an end tool of the surgical instrument is disposed in a direction away from the body, a first surface of the fifth link, to which the surgical instrument is coupled, may be disposed to face upward in a Z-axis direction.

In the present disclosure, in the state, the surgical instrument may be disposed above the fifth link.

In the present disclosure, in a state in which the surgical instrument coupled to the fifth link is horizontal and an end tool of the surgical instrument is disposed in a direction away from the body, a first surface of the fifth link, to which the surgical instrument is coupled, may be disposed to face downward in a Z-axis direction.

In the present disclosure, in the state, the surgical instrument may be disposed below the fifth link.

In the present disclosure, in the state, the links may not be disposed between the surgical instrument and a bed.

In the present disclosure, based on a plane perpendicular to a Z-axis, the first yaw axis and at least some of the third link, the fourth link, and the fifth link may be formed to form a predetermined angle.

In the present disclosure, the first yaw axis and at least some of the third link, the fourth link, and the fifth link may be formed parallel to each other.

In the present disclosure, a height of the first yaw axis in a Z-axis direction at a distal end may be formed greater than a height of the first yaw axis in the Z-axis direction at a proximal end.

In the present disclosure, the base link may be formed to be inclined at a predetermined angle with respect to the extension line connecting the third joint to the RCM, so that a central axis of the base link is formed to coincide with the first yaw axis.

In the present disclosure, the first yaw axis and the extension line connecting the third joint to the RCM may intersect at the RCM.

Another embodiment of the present disclosure provides a surgical method using a surgical robot, the surgical method including disposing a body of a modular surgical robot arm on one side of a port of a patient, into which a surgical instrument is to be inserted, disposing a fifth link to which the surgical instrument is mounted in a substantially horizontal state in the surgical robot arm, mounting the surgical instrument to the fifth link of the surgical robot arm, moving the surgical instrument mounted to the surgical robot arm and inserting the surgical instrument into a body of the patient, and performing a surgery by the surgical instrument while maintaining a remote center of motion (RCM).

In the present disclosure, in the disposing of the body of the modular surgical robot arm on one side of the port of the patient, into which the surgical instrument is to be inserted, the body of the surgical robot arm may be disposed on the same side as the port of the patient based on a bed.

In the present disclosure, in the disposing of the fifth link to which the surgical instrument is mounted in a substantially horizontal state in the surgical robot arm, at least some of a plurality of links of the surgical robot arm may be formed to overlap each other in an extension direction of each of the links.

In the present disclosure, in the mounting of the surgical instrument on the fifth link of the surgical robot arm, links of the surgical robot arm may not be disposed between the surgical instrument and the patient.

In the present disclosure, the surgical robot arm may include a base link, a yaw drive assembly formed to be yaw rotatable around a first yaw axis with respect to the base link, a third link axially coupled to the yaw drive assembly so as to be rotatable around a third joint with respect to the yaw drive assembly, a fourth link axially coupled to the third link so as to be rotatable around a fourth joint with respect to the third link, and a fifth link axially coupled to the fourth link so as to be rotatable around a fifth joint with respect to the fourth link, and formed to allow the surgical instrument to be mounted thereto, wherein the RCM may be formed at the remaining vertex of a parallelogram with the third joint, the fourth joint, and the fifth joint constituting vertices, and the first yaw axis and an extension line connecting the third joint to the RCM may be formed to be different from each other.

In the present disclosure, the first yaw axis and the extension line connecting the third joint to the RCM may intersect at the RCM.

In the present disclosure, the RCM may be positioned on an extension line of the first yaw axis.

In the present disclosure, when the third link rotates around the third joint, the third link and the fifth link rotate while maintaining a parallel state, and the fourth link and the extension line connecting the third joint to the RCM rotate while maintaining a parallel state.

In the present disclosure, a height of the RCM in a Z-axis direction may be formed to be greater than a height of a point of the base link, through which the first yaw axis passes, in the Z-axis direction.

In the present disclosure, a height of the first yaw axis in a Z-axis direction at a distal end may be formed greater than a height of the first yaw axis in the Z-axis direction at a proximal end.

In the present disclosure, the base link is formed to be inclined at a predetermined angle with respect to a horizontal plane so that a central axis of the base link coincides with a first yaw axis.

In the present disclosure, each of the third link, the fourth link, and the fifth link may be formed to be offset by a certain degree in a direction of a rotation axis thereof.

In the present disclosure, based on a direction of a rotation axis of the third link, the fourth link may be disposed on one side of the third link, and the fifth link may be disposed on one side of the fourth link.

In the present disclosure, based on a direction of the first yaw axis, at least a portion of each of the third link, the fourth link, and the fifth link can overlap each other.

In the present disclosure, in a state in which the surgical instrument coupled to the fifth link is horizontal and an end tool of the surgical instrument is disposed in a direction away from the body, a first surface of the fifth link, to which the surgical instrument is coupled, may be disposed to face downward in a Z-axis direction.

In the present disclosure, in the state, the surgical instrument may be disposed below the fifth link.

In the present disclosure, in the state, the links may not be disposed between the surgical instrument and a bed.

In the present disclosure, the first yaw axis and the extension line connecting the third joint to the RCM may be formed to form a predetermined angle rather than being parallel to each other.

Other aspects, features, and advantages other than those described above will become apparent from the following drawings, claims, and detailed description of the disclosure.

MODE OF DISCLOSURE

While the present disclosure may be susceptible to various modifications and include various embodiments, specific embodiments thereof have been shown in the drawings by way of example and will now be described in detail. However, it should be understood that there is no intent to limit the present disclosure to the specific embodiments disclosed herein, rather, the present disclosure should be construed to cover various modifications, equivalents, and alternatives of embodiments of the present disclosure. In describing the present disclosure, a detailed description of known related arts will be omitted when it is determined that the gist of the present disclosure may be unnecessarily obscured Although terms such as "first," "second," and the like may be used to describe various components, such components should not be limited to the above terms The terms are only used to distinguish one component from another.

The terms used herein are for the purpose of describing specific embodiments only and are not intended to be limiting to the present disclosure. Singular forms are intended to include plural forms as well, unless the context clearly indicates otherwise. In the present application, it will be further understood that the terms "comprise," "comprising," "include," and/or "including," when used in this specification, specify the presence of stated features, integers, steps, operations, elements, components and/or groups thereof but do not preclude the presence or addition of one or more other features, integers, steps, operations, elements, components and/or groups thereof.

Hereinafter, the embodiments of the present disclosure will be described below in detail with reference to the accompanying drawings, and when the embodiments of the present disclosure are described with reference to the drawings, the same or corresponding components are given the same reference numerals, and repetitive descriptions thereof will be omitted.

Further, in describing the various embodiments of the present disclosure, it is to be understood that each embodiment is not intended to be interpreted or implemented independently, and that the technical ideas described in each embodiment may be interpreted or implemented in combination with other embodiments described separately.

Hereinafter, an embodiment of the present disclosure will be described with reference to the accompanying drawings.

Figure 66:
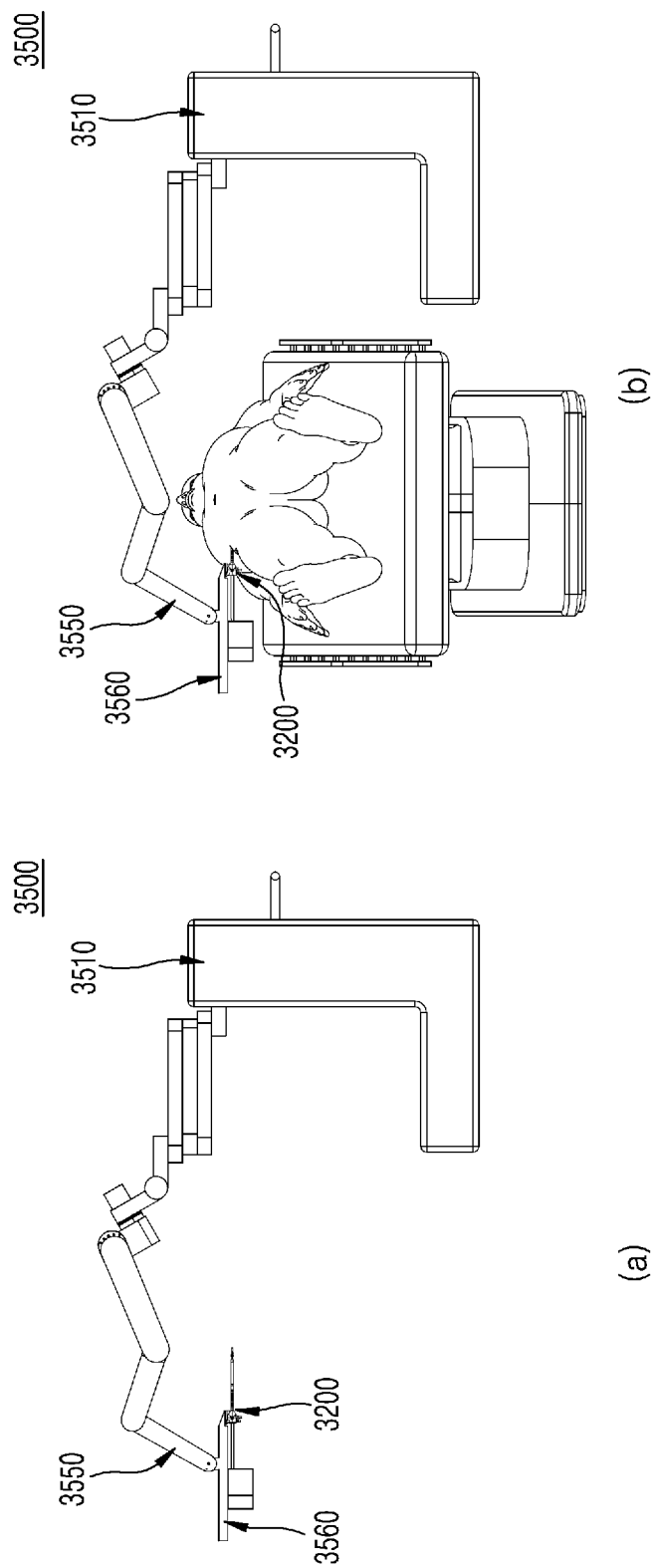

FIG. 66 is a view illustrating a surgical robot arm.

As shown in FIG. 66, a surgical robot arm 3500 typically operates in a manner in which one or a plurality of robot arms extend away from a single tower. In such a structure, in the case of surgery that requires a surgical instrument 3200 to be inserted in a direction horizontal to the plane of the operating table on which a patient is lying, it was common that a tower 3510 is positioned across from a patient's surgical site, the surgical robot arm 3500 is deployed to extend away from the tower 3510 as if covering an upper portion of a patient's body, and the surgical instrument 3200 is disposed in a direction opposite to a direction, in which the surgical instrument 3200 extends, so as to face toward the patient again. Thus, this may result in a disadvantage such as deploying multiple robot arms above the patient, along with other drawbacks like an increase in vibration and a reduction in rigidity occurring due to the way the surgical robot arm 3500 extends away from its support, i.e., the tower 3510.

In order to address these issues, as shown in FIG. 1, each robot arm may be formed in a modular manner, each module may be disposed near a surgical site, and an instrument may be formed to face directly toward a patient.

However, when one rotation axis (a yaw axis) among multiple rotation axes around which the surgical instrument rotates coincides with an instrument's roll axis, which corresponds to an extension line of the instrument, as shown in FIG. 1, a gimbal lock phenomenon may occur in which a motion (a yaw motion) of the surgical instrument expected when rotating around the one rotation axis (the yaw axis) becomes impossible. In particular, in a case in which the instrument is horizontally disposed, a situation corresponding to the gimbal lock phenomenon may frequently occur when the yaw axis is horizontally disposed.

In order to address such a problem, in the present disclosure, the yaw axis is disposed in a direction (e.g., an inclined direction with respect to the horizontal plane) other than a horizontal direction to prevent the gimbal lock phenomenon from occurring even when the instrument is horizontally disposed, so that gimbal lock may not occur even in the most commonly used positioning of the surgical instrument, thereby enabling a more compact configuration of the overall surgical robot.

Further, in the present disclosure, the surgical robot arm is formed in a modular manner in which a single surgical instrument is deployed from a single body of the surgical robot arm. In addition, a plurality of modular surgical robot arms, each equipped with a single surgical instrument, are provided. In addition, each of these surgical robot arms is disposed in the vicinity of each of a plurality of ports of the patient, so that the overall length of the deployed surgical robot arms is reduced, thereby obtaining an effect of reducing vibration and increasing rigidity.

Figure 17:
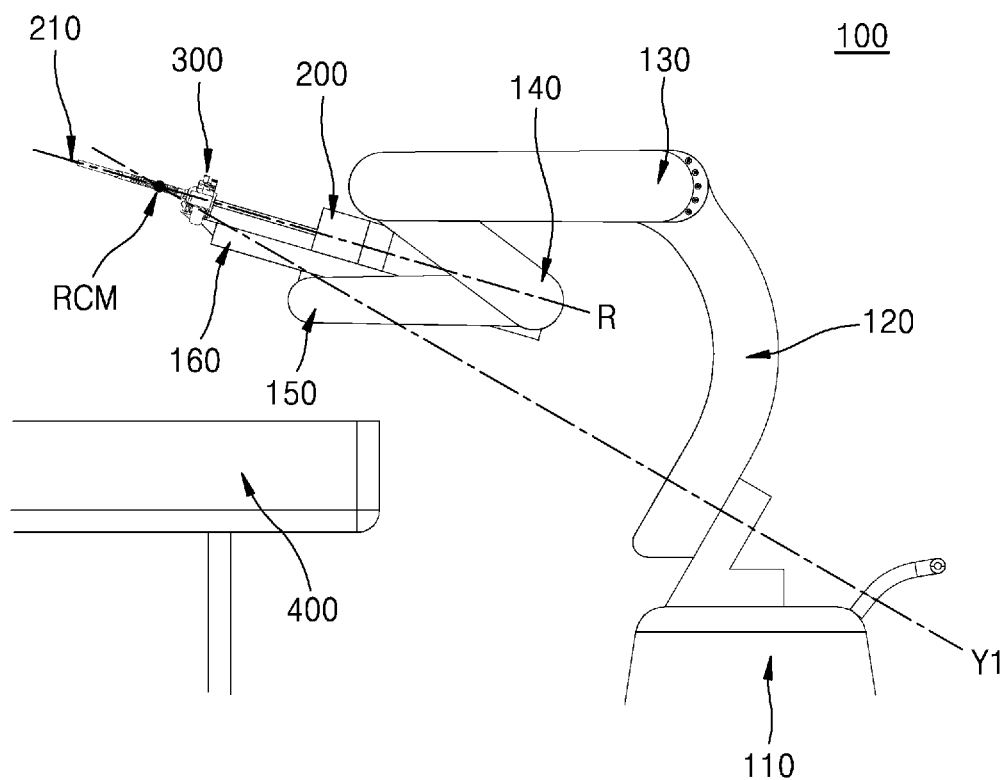
FIG. 17 is a view illustrating a state in which an end tool of the surgical instrument coupled to the fifth link of the surgical robot arm of FIG. 3 is disposed facing upward from below.

Furthermore, in the present disclosure, as shown in FIG. 9B and elsewhere herein, a fourth link 150 and a fifth link 160 are arranged side by side to be adjacent to each other (when viewed from an XY plane) so that the fourth link 150 and the fifth link 160 are formed to overlap each other (when viewed from an XZ plane), and thus, as shown in FIG. 17, a rotational motion of the fourth link is not constrained by other links such as the fifth link, thereby increasing the range of motion of the instrument, such as allowing a moving direction of the instrument to extend beyond the horizontal direction and face upward. Accordingly, even in the frequent case of surgery, in which the instrument is disposed in the horizontal direction, an effect of preventing the gimbal lock and allowing the instrument to move with a sufficient range of motion may be obtained. This will be described in more detail below.

Figure 2:
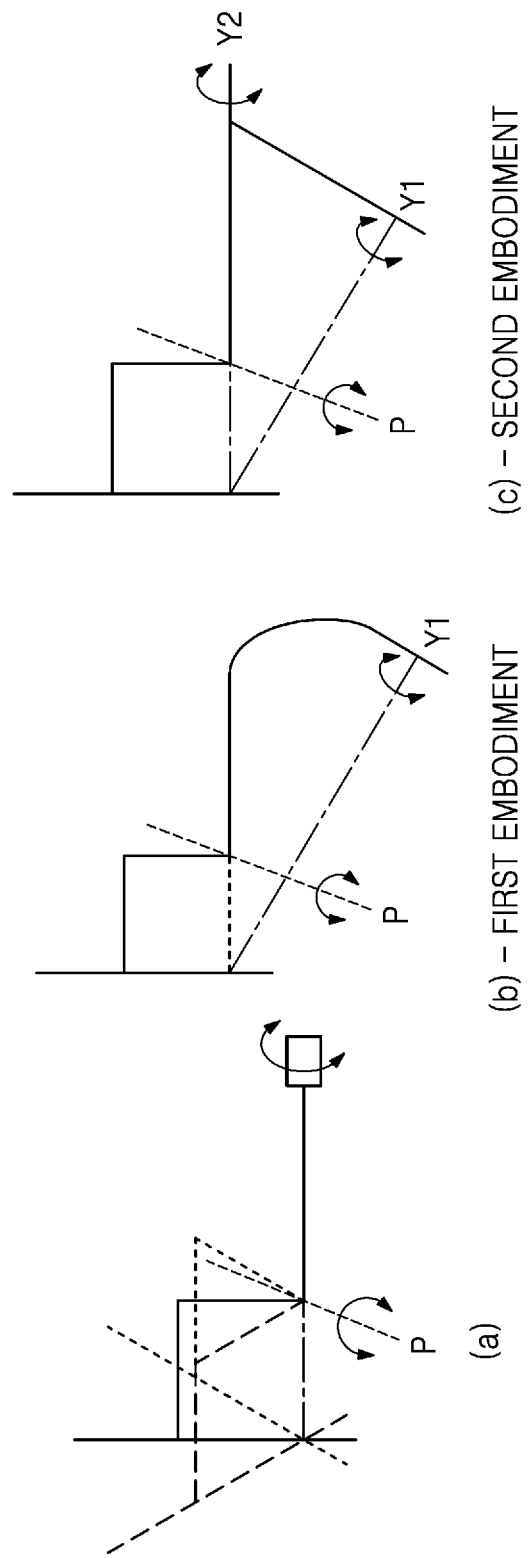
FIG. 2 is a conceptual view of a surgical robot arm according to each embodiment of the present disclosure.

FIG. 2 is a conceptual view of a surgical robot arm according to each embodiment of the present disclosure.

In detail, FIG. 2A is a conceptual view when a yaw axis is disposed in the horizontal direction. That is, a case in which the yaw axis is disposed on the XY plane is illustrated. In this case, it may be difficult to perform motions that require the instrument to face upward from below.

Meanwhile, FIG. 2B is a conceptual view of a surgical robot arm according to a first embodiment of the present disclosure. FIG. 2B illustrates a case in which one yaw axis is formed to be inclined in a direction different from the horizontal direction, more specifically, the yaw axis is formed to be inclined to face upward from below when viewed from a YZ plane. With this configuration, gimbal lock does not occur even when the instrument is horizontally disposed, that is, in the most commonly used positioning of the surgical instrument, thereby enabling a more compact configuration of the overall surgical robot.

Meanwhile, FIG. 2C is a conceptual view of a surgical robot arm according to a second embodiment of the present disclosure. In the case of FIG. 2C, two yaw axes are included. That is, a first yaw axis Y1 is formed to be inclined in a direction different from the horizontal direction, more specifically, the first yaw axis Y1 is formed to be inclined to face upward from below when viewed from the YZ plane. In addition, another yaw axis, i.e., a second yaw axis Y2, is disposed on the XY plane in the horizontal direction. By including two yaw axes as described above, one of the two yaw axes can be utilized to prevent gimbal lock regardless of the positioning the surgical robot arm. In addition, using one of the two yaw axes as a positioning arm facilitates easier module positioning and surgical configuration."

Specific configurations of each embodiment will be described in more detail in each embodiment.

<First Embodiment of Surgical Robot Arm>

Hereinafter, a first embodiment of the present disclosure will be described with reference to the accompanying drawings.

Figure 3:
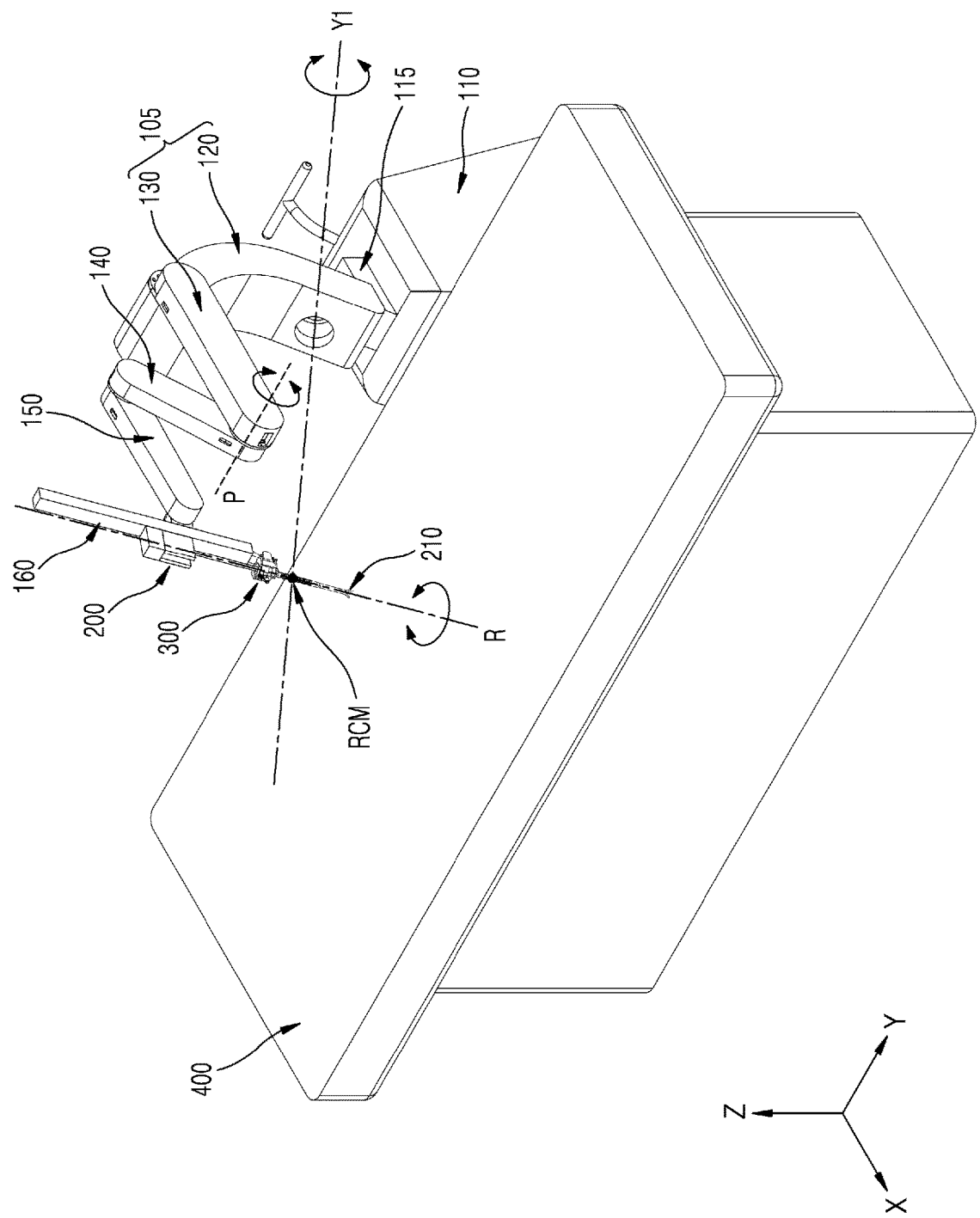
FIG. 3 is a perspective view illustrating a surgical robot arm according to a first embodiment of the present disclosure.
Figure 4:
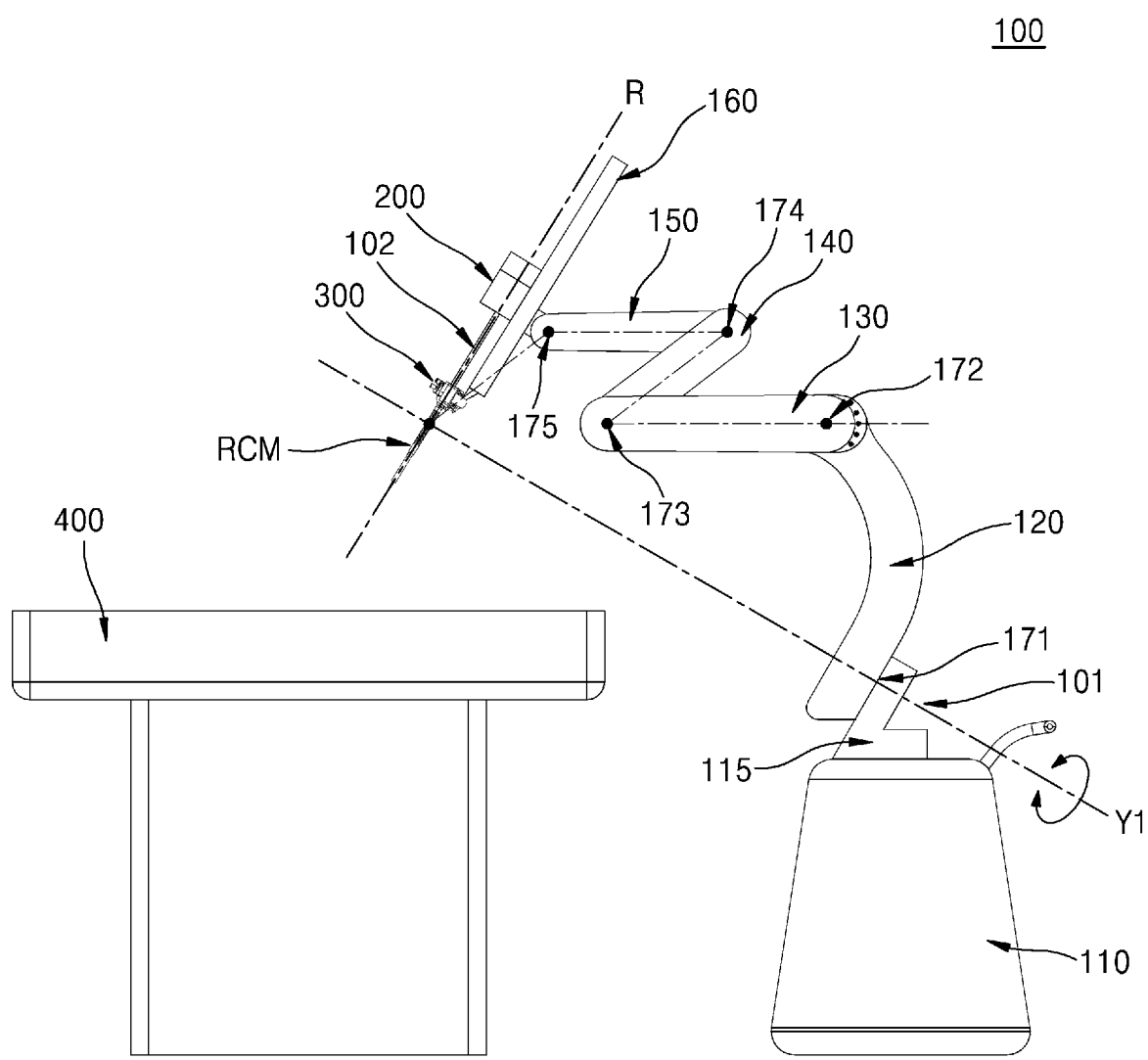
FIG. 4 is a plan view of the surgical robot arm of FIG. 3.
Figure 5:
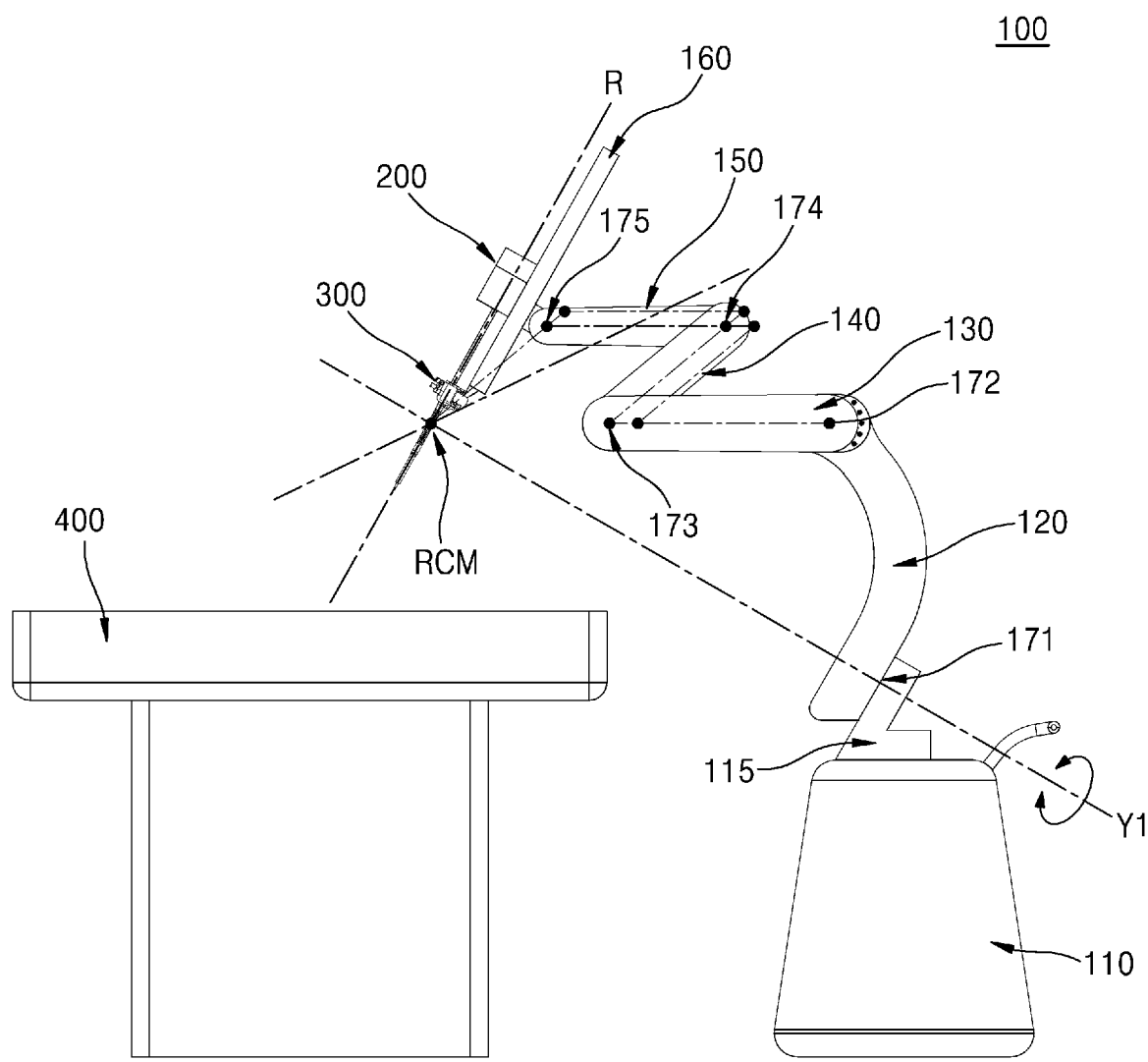
FIG. 5 is a view illustrating an example in which a remote center of motion (RCM) mechanism of a link structure is applied to the surgical robot arm of FIG. 2.
Figure 6:
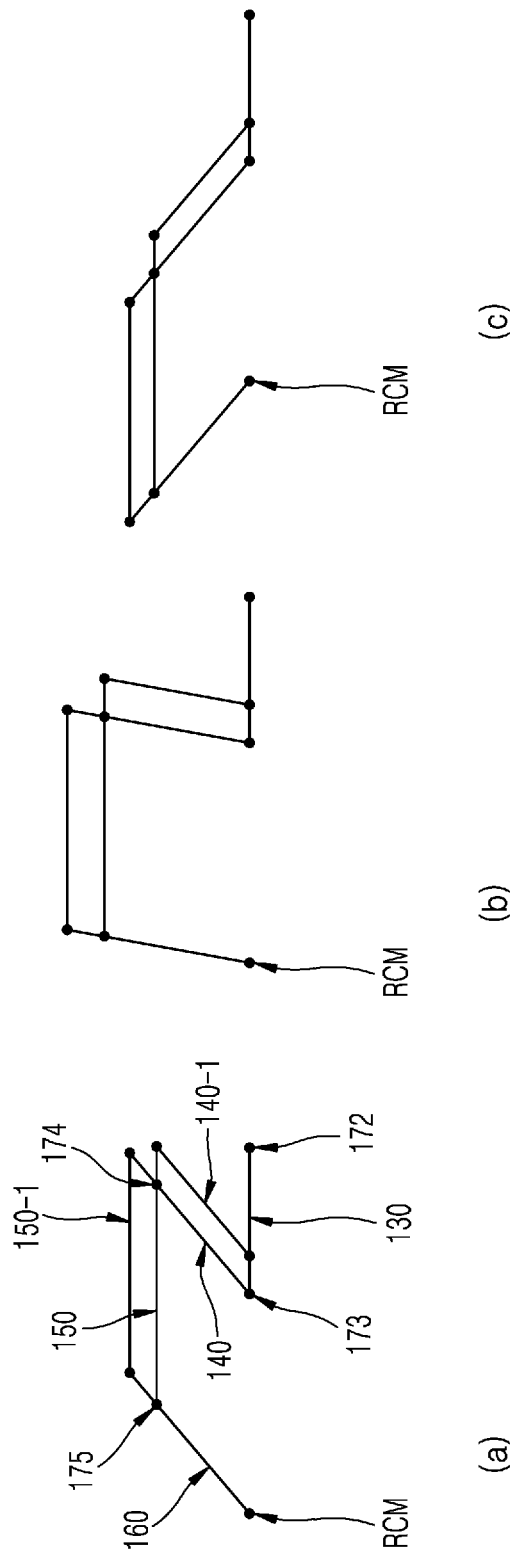
FIG. 6 is a view illustrating motion states of the RCM mechanism of a link structure.
Figure 7:
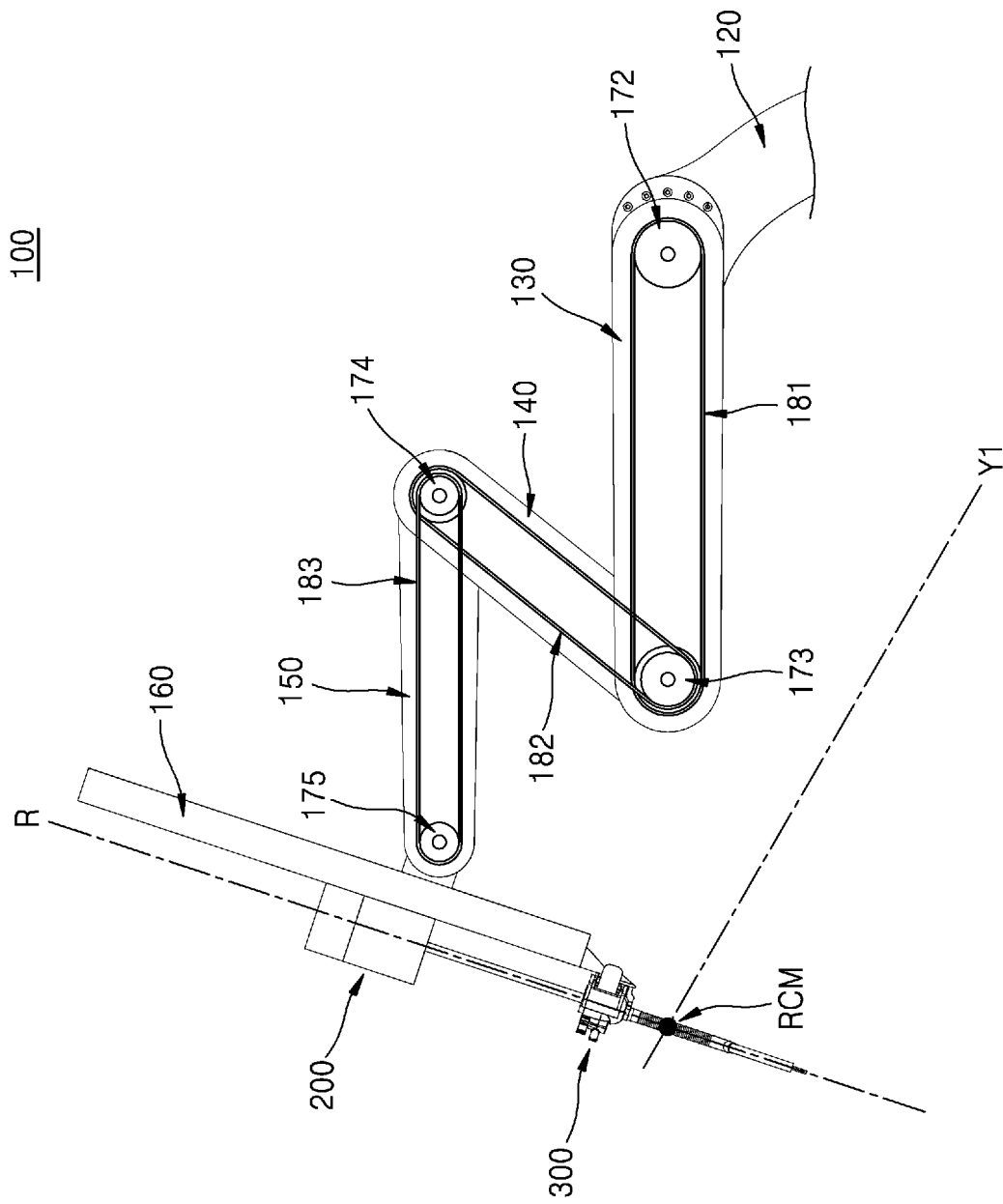
FIG. 7 is a view illustrating an example in which an RCM mechanism of a belt structure is applied to the surgical robot arm of FIG. 2.
Figure 8:
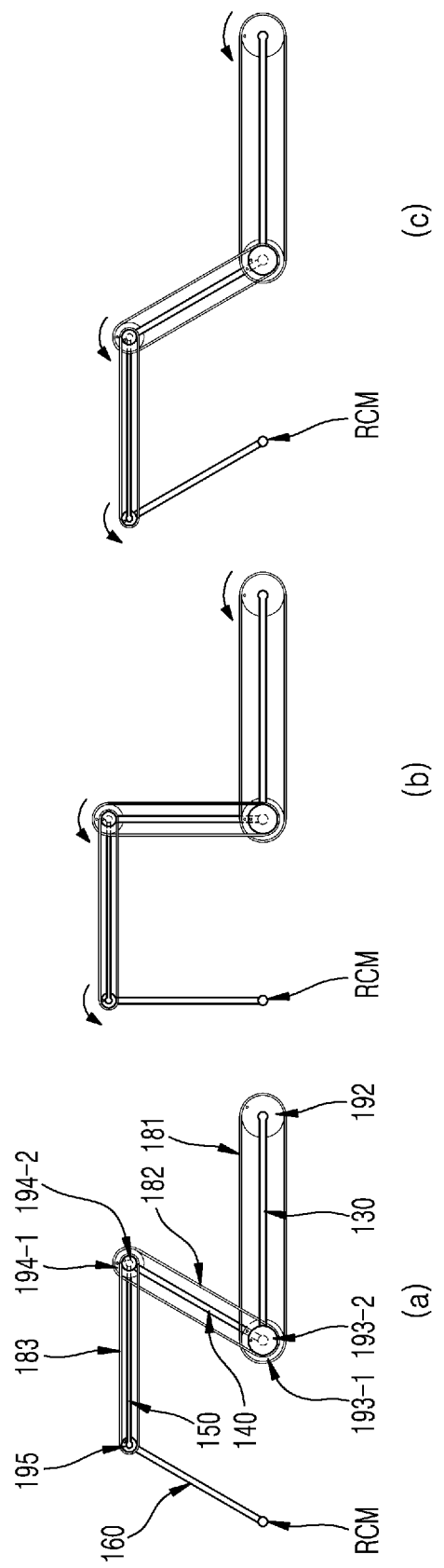
FIG. 8 is a view illustrating motion states of the RCM mechanism of a belt structure.
Figure 9:
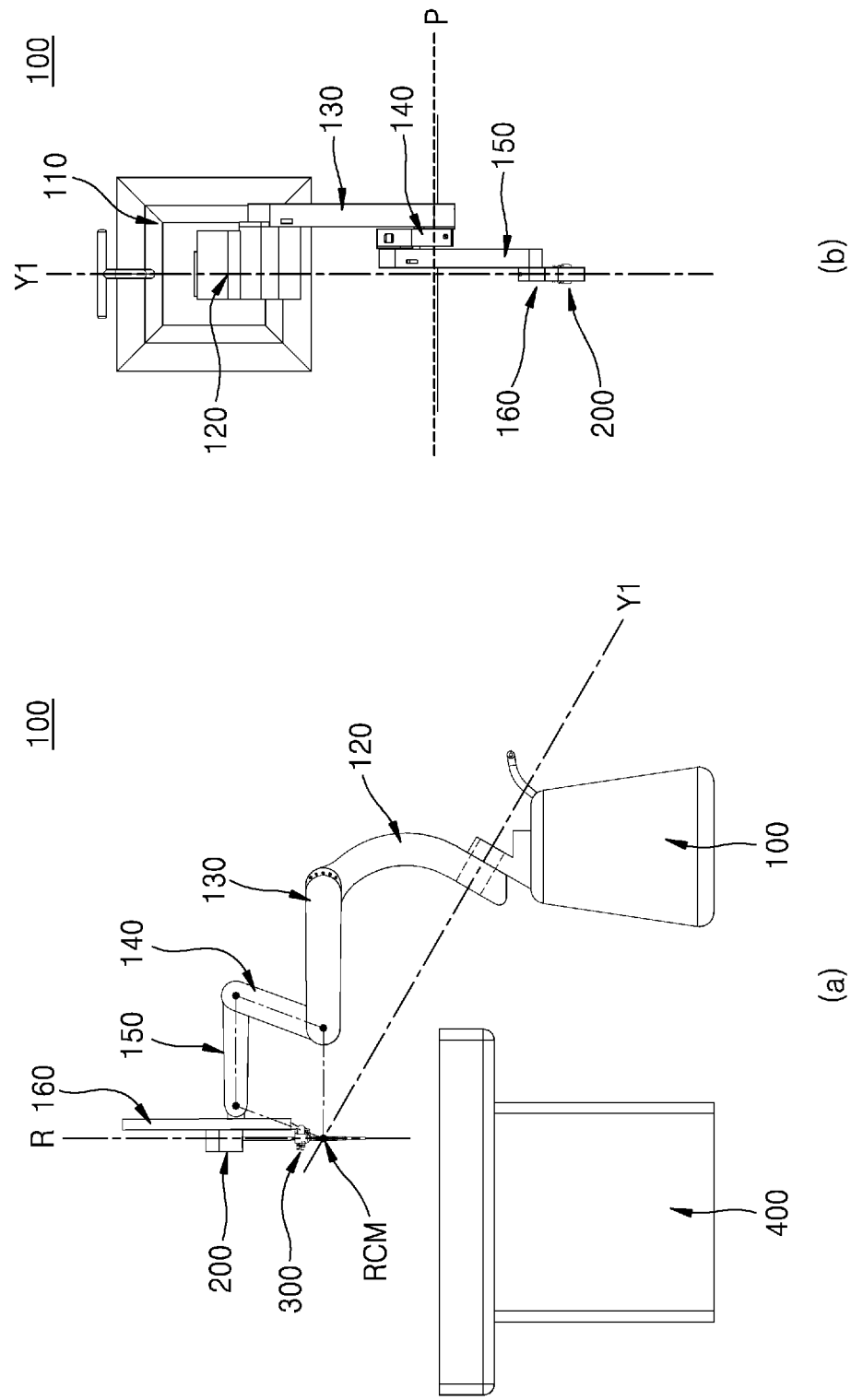
FIGS. 9 to 11 are views illustrating an RCM motion (a pitch motion) of the surgical robot arm of FIG. 3 around a pitch axis P, each view including both a side view and a plan view.
Figure 10:
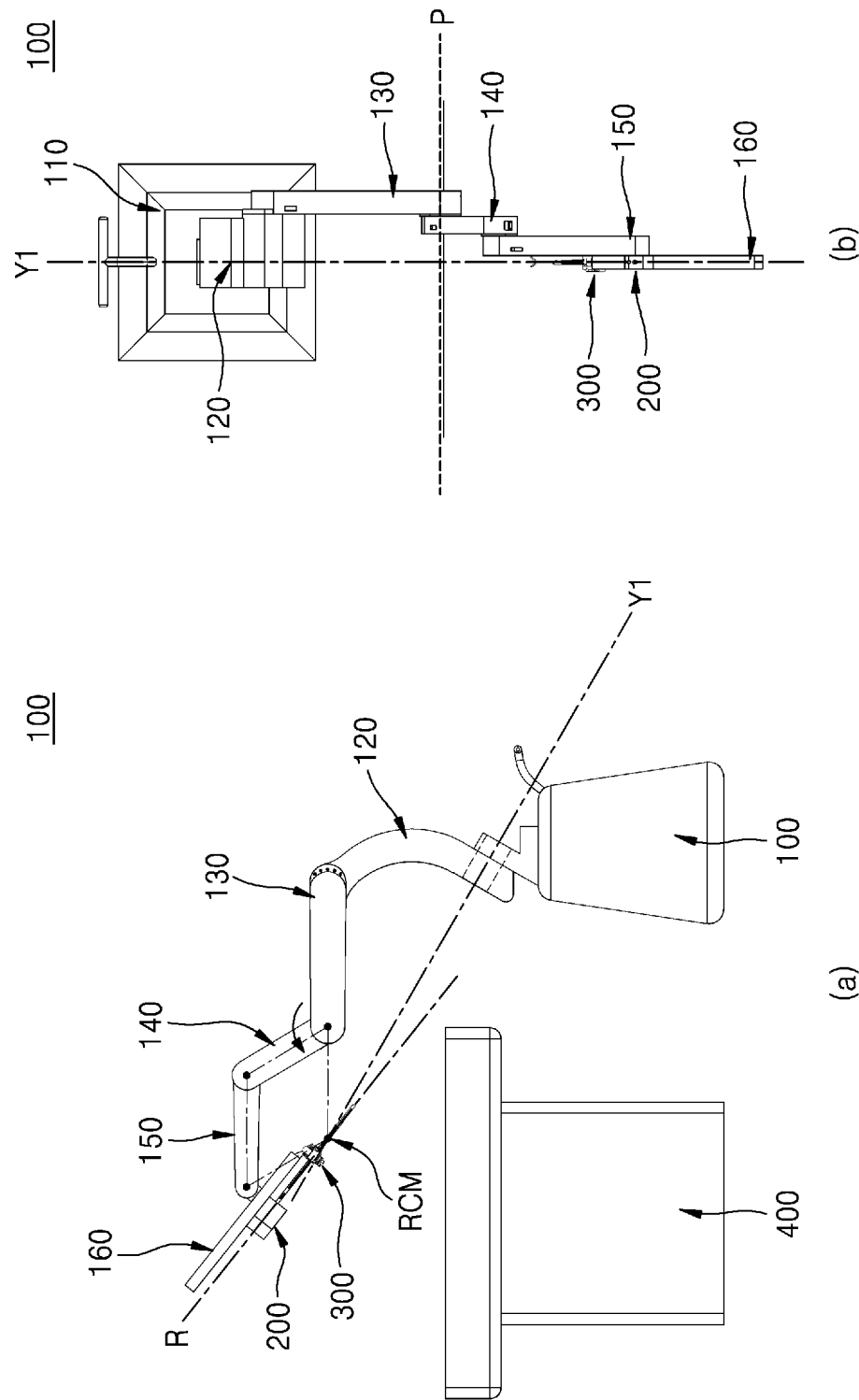
Figure 11:
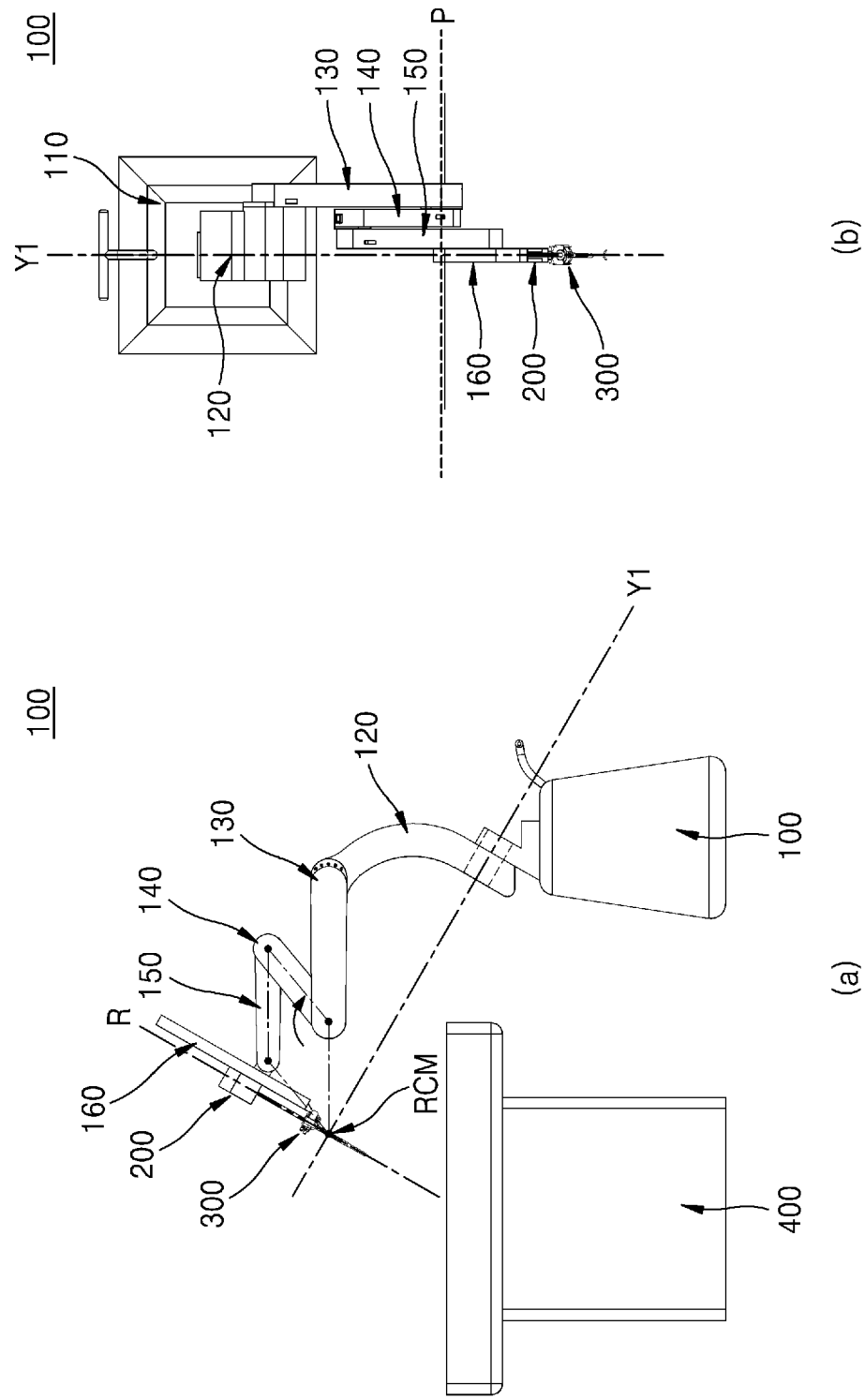
Figure 12:
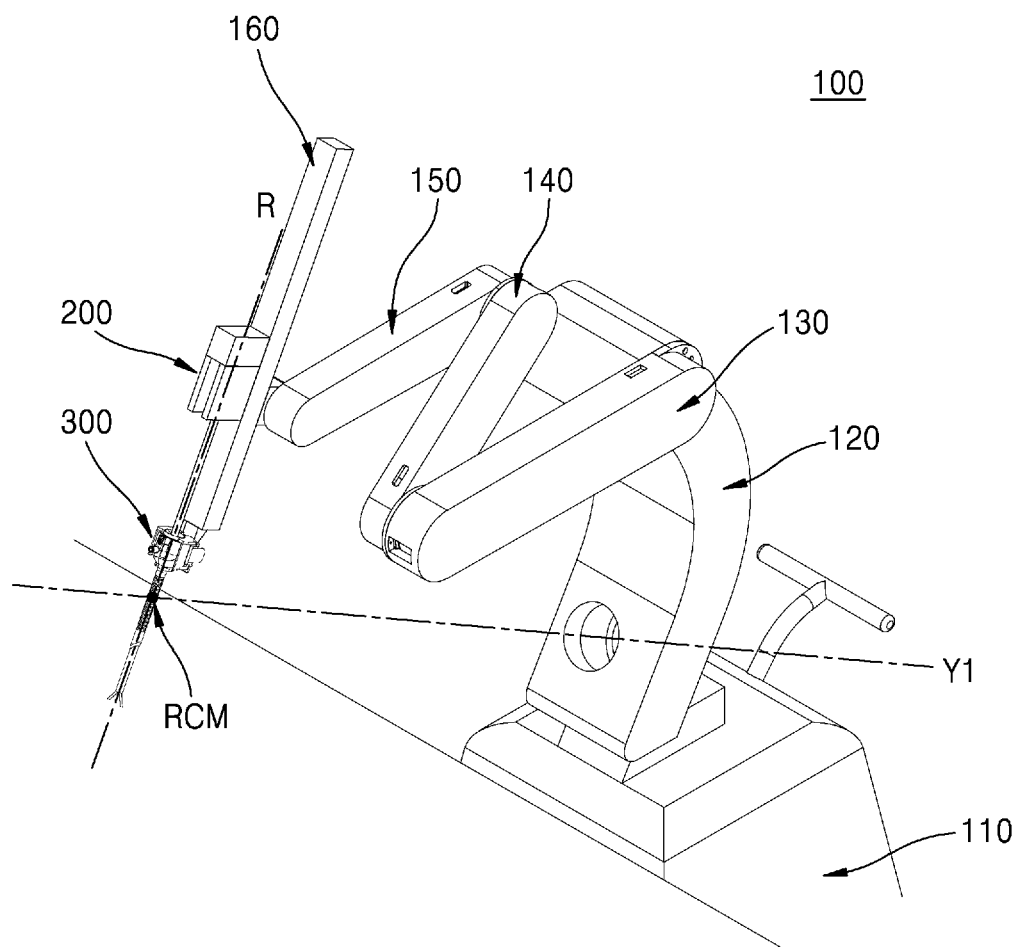
FIGS. 12 to 14 are perspective views illustrating an RCM motion (a yaw motion) of the surgical robot arm of FIG. 3 around a first yaw axis Y1.
Figure 13:
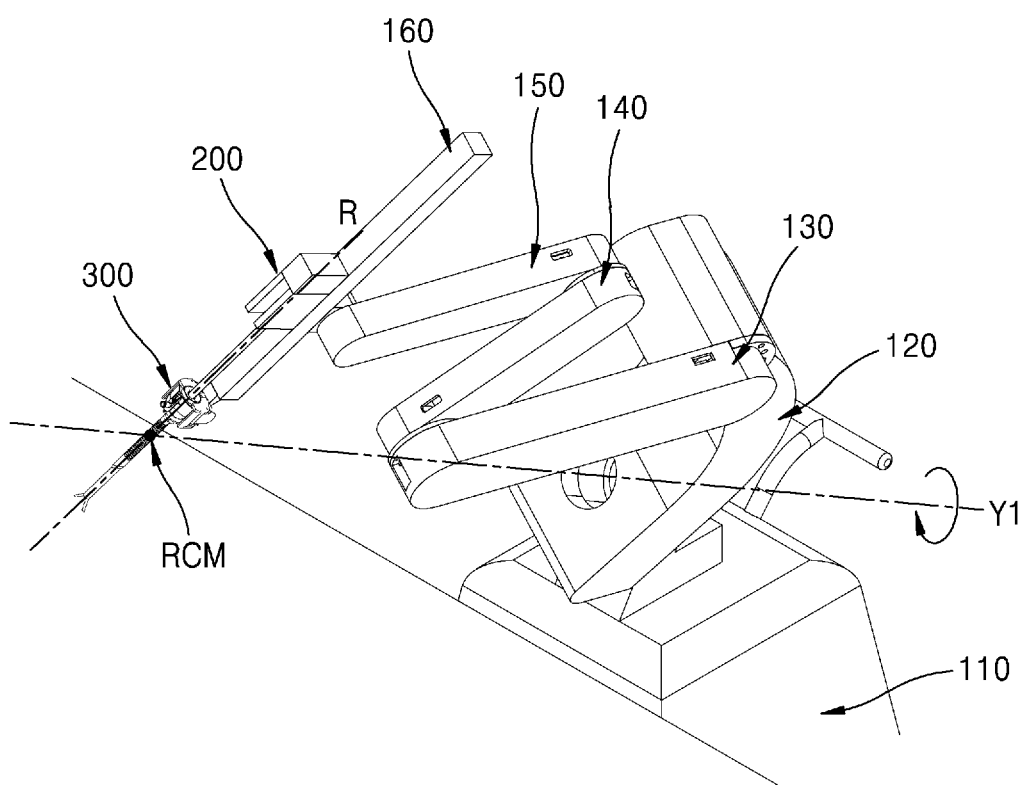
Figure 14:
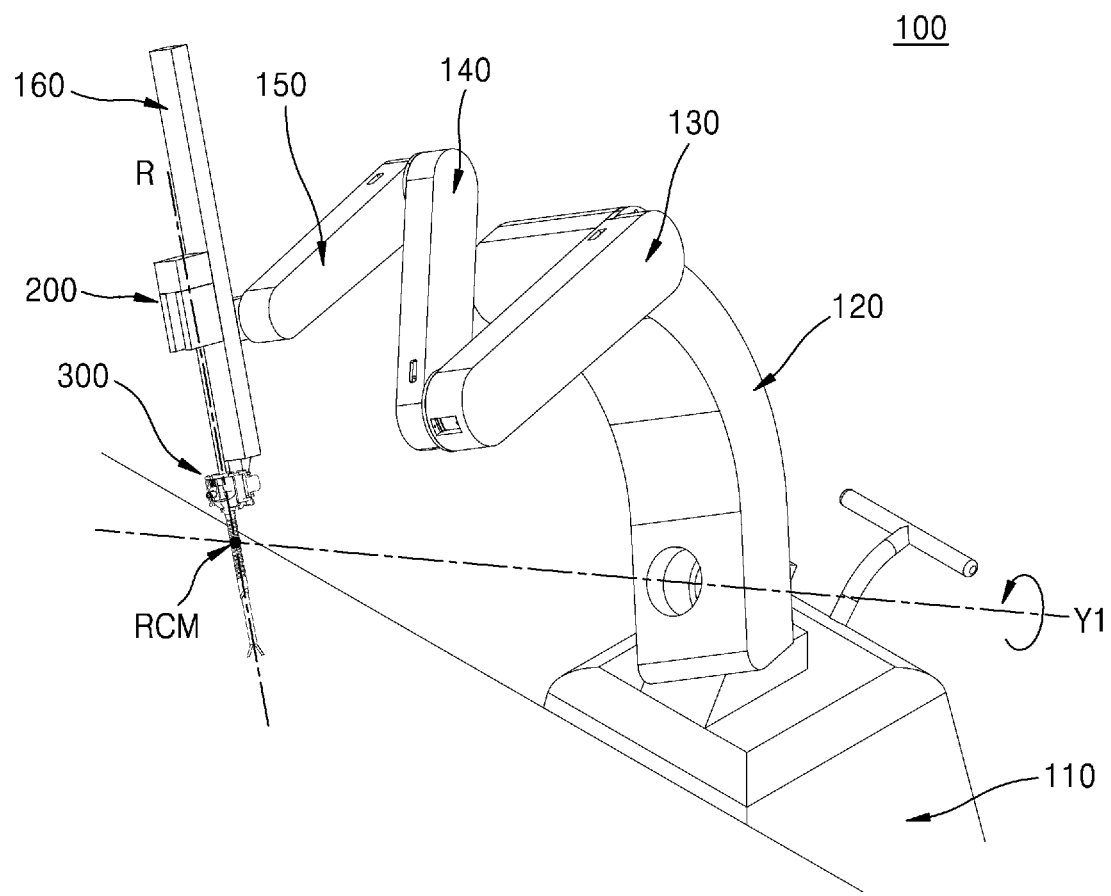
Figure 15:
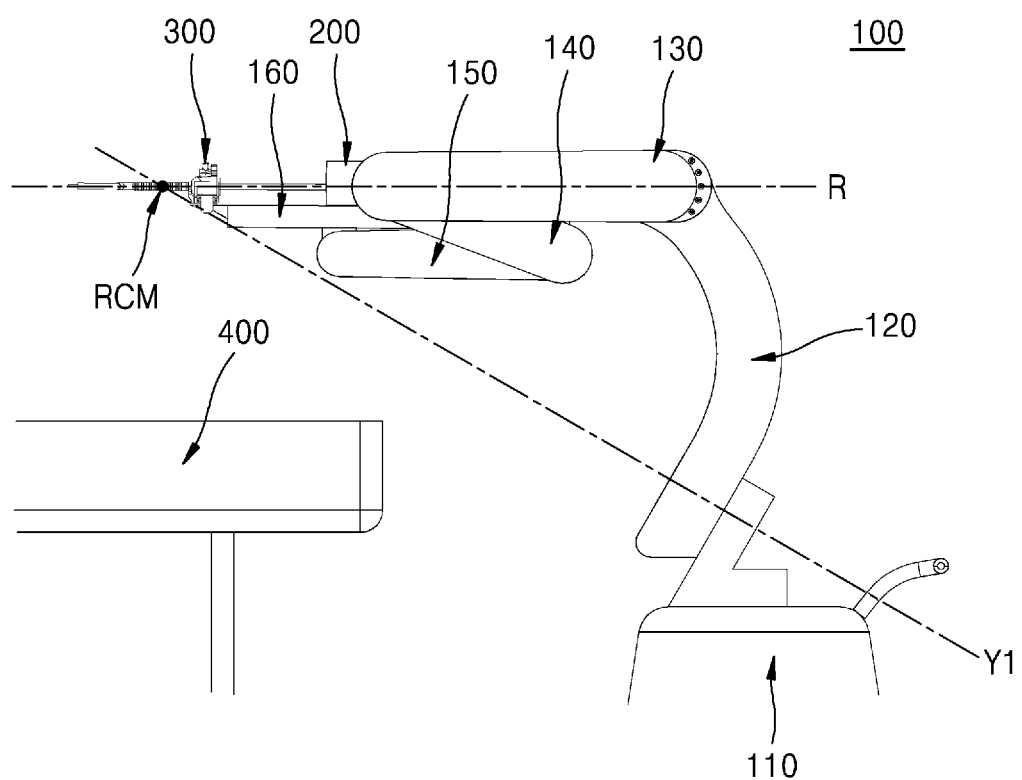
FIG. 15 is a view illustrating a state in which a fifth link of the surgical robot arm of FIG. 3 and a surgical instrument coupled thereto are disposed parallel to each other.
Figure 16:
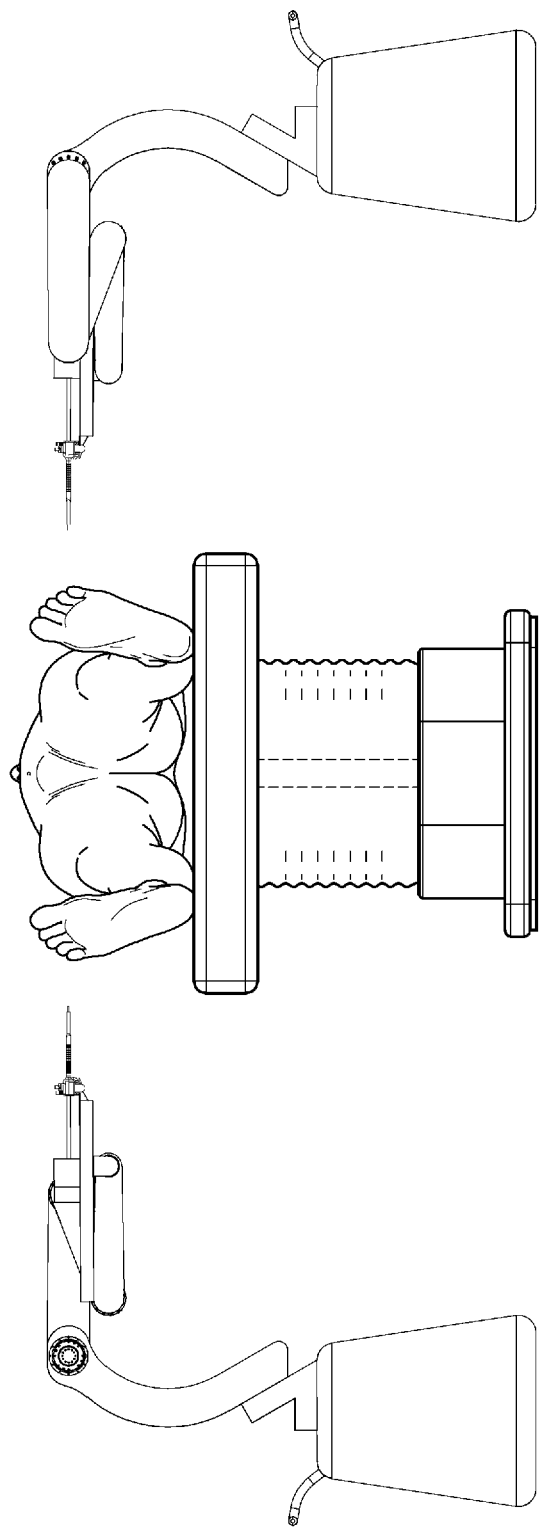
FIG. 16 is a view illustrating a state in which the surgical robot arm illustrated in FIG. 15 is disposed near a patient's surgical site and the surgical instrument is disposed directly facing a patient.

FIG. 3 is a perspective view illustrating a surgical robot arm according to the first embodiment of the present disclosure, and FIG. 4 is a plan view of the surgical robot arm of FIG. 3. FIG. 5 is a view illustrating an example in which a remote center of motion (RCM) mechanism of a link structure is applied to the surgical robot arm of FIG. 2, and FIG. 6 is a view illustrating motion states of the RCM mechanism of a link structure. FIG. 7 is a view illustrating an example in which an RCM mechanism of a belt structure is applied to the surgical robot arm of FIG. 2, and FIG. 8 is a view illustrating motion states of the RCM mechanism of a belt structure. FIGS. 9 to 11 are views illustrating an RCM motion (a pitch motion) of the surgical robot arm of FIG. 3 around a pitch axis P, each view including both a side view and a plan view. FIGS. 12 to 14 are perspective views illustrating an RCM motion (a yaw motion) of the surgical robot arm of FIG. 3 around the first yaw axis Y1. FIG. 15 is a view illustrating a state in which a fifth link of the surgical robot arm of FIG. 3 and a surgical instrument coupled thereto are disposed parallel to each other, and FIG. 16 is a view illustrating a state in which the surgical robot arm illustrated in FIG. 15 is disposed near a patient's surgical site and the surgical instrument is disposed directly facing a patient. FIG. 17 is a view illustrating a state in which an end tool of the surgical instrument coupled to the fifth link of the surgical robot arm of FIG. 3 is disposed facing upward from below.

First, referring to FIGS. 3 and 4, a surgical robot arm 100 according to the first embodiment of the present disclosure includes a body 110, a base link 115, a yaw drive assembly 105, a third link 140, a fourth link 150, and a fifth link 160. Here, the yaw drive assembly 105 may include a first link 120 and a second link 130. In addition, the surgical robot arm 100 may include a first joint 171, a second joint 172, a third joint 173, a fourth joint 174, and a fifth joint 175. In addition, a trocar 300 and a surgical instrument 200 are coupled to the fifth link 160 of the surgical robot arm 100 described above.

Here, the third link 140, the fourth link 150, and the fifth link 160 form a parallelogram, and configure a kind of RCM mechanism.

In detail, a surgical robot may include one or more surgical robot arms for surgical manipulation, and a surgical instrument is mounted on a front-end portion of the surgical robot arm.

In general, a robot arm refers to a device having a function similar to that of the arm and/or the wrist of a human being and having a wrist portion to which a certain tool may be attached. In the present specification, the robot arm may be defined as a concept that encompasses all of components, such as an upper arm, a lower arm, a wrist, and an elbow, and a surgical instrument coupled to the wrist portion. The above-described surgical robot arm may be implemented to have multiple degrees of freedom.

When a surgery is performed by mounting the surgical instrument to the front end of the surgical robot arm as described above, the surgical instrument moves along with the movement of the surgical robot arm, which may cause unnecessary damage to the human skin in the process of performing a surgery, making a small puncture in a patient's skin and inserting a surgical instrument into the puncture. In addition, when a surgical site is large, there is a concern that the advantages of robotic surgery may be halved due to the need to cut the skin by as much as a moving path of the surgical instrument or the need to puncture the skin at each surgical site.

Accordingly, a virtual rotation center point is set at a certain position (mainly a pivot point through which the trocar penetrates the patient's skin) with respect to the surgical instrument mounted at the front end of the surgical robot arm, and the robot arm is controlled so that the instrument rotates around the certain position, which is referred to as a "remote center" or "remote center of motion" (RCM). The RCM mechanism of the present disclosure will be described in more detail later.

Hereinafter, each component of the surgical robot arm 100 according to the first embodiment of the present disclosure will be described in more detail.

In the present embodiment, for convenience, a width direction of a bed on which a patient lies is defined as an X-axis, a length direction of the bed is defined as a Y-axis, and a direction perpendicular to the ground is defined as a Z-axis.

The body 110 serves as a base of the entire surgical robot arm 100. Here, a moving device (not shown) such as a wheel is formed on a lower surface of the body 110, and thus the body 110 may also serve as a kind of moving member. In addition, a position-fixing device (not shown) may be further formed on the body 110, so that the position of the body 110 may be fixed during surgery. However, the concept of the present disclosure is not limited thereto, and the body 110 may be formed in such a shape that is detachable from the bed or such a shape that is detachable from a wall surface.

The base link 115 may be formed on one surface of the body 110, for example, an upper surface thereof. The base link 115 may be formed to be inclined by a certain degree to have a predetermined angle with respect to a horizontal plane.

In detail, the base link 115 may be formed in the form of a bent flat plate or wedge, with one region coupled to the upper surface of the body 110 and another one bent region disposed to be inclined with respect to the upper surface of the body 110. Here, the base link 115 may be formed to be inclined by a certain degree (e.g., 30°) with respect to the horizontal plane rather than a right angle, so that the first yaw axis Y1 passing through the base link 115 may be formed not to be parallel to the horizontal direction (i.e., an X-axis direction). This will be described in more detail later.

Meanwhile, the yaw drive assembly 105 is rotatably coupled to the base link 115.

In detail, the yaw drive assembly 105 may include the first link 120 and the second link 130. The yaw drive assembly 105 is coupled to the base link 115 by the first joint 171, and formed to be yaw rotatable around the first yaw axis Y1 with respect to the base link 115. Here, the first link 120 is coupled to the base link 115 by the first joint 171, and formed to be yaw rotatable around the first yaw axis Y1 with respect to the base link 115. In addition, one end portion of the second link 130 is fixedly coupled to the first link 120, and another end portion thereof is coupled to the third link 140 to be described later.

The first joint 171 rotatably couples the first link 120 to the base link 115. In detail, the first joint 171 is formed so that the first link 120 yaw-rotates around the first yaw axis Y1 formed to pass through the RCM. Here, although not shown in the drawings, the first joint 171 may include a motor for rotating the first link 120.

Here, the first yaw axis Y1 may be formed in an oblique direction that is not parallel to the X-axis/Y-axis/Z-axis. Specifically, the first yaw axis Y1 and an extension line connecting the third joint 173 to the RCM, which will be described later, may be formed to be different from each other, and the first yaw axis Y1 and the extension line connecting the third joint 173 to the RCM may be formed to intersect each other at the RCM. In this case, the RCM to be described later may be positioned on an extension line of the first yaw axis Y1. In other words, the first yaw axis Y1 and the extension line connecting the third joint 173 to the RCM may be formed to form a predetermined angle rather than being parallel to each other. By forming the RCM to be positioned on the extension line of the first yaw axis Y1 as described above, the position and orientation of the RCM with respect to the base link 115 remains constant regardless of how much yaw rotation the first link 120 has made relative to the base link 115.

Here, as described above, as the base link 115 is formed to be inclined by a certain degree (e.g., 30°) rather than a right angle, the first yaw axis Y1 passing through the base link 115 may be formed not to be parallel to the horizontal direction (i.e., the X-axis direction). In addition, the first yaw axis Y1 and the extension line connecting the third joint 173 to the RCM may be formed to be different from each other.

In other words, it may be said that a height of the RCM in a Z-axis direction is formed to be greater than a height of a point (i.e., the first joint 171) of the base link 115, through which the first yaw axis Y1 passes through, in the Z-axis direction.

In other words, it may be said that a height of the first yaw axis Y1 in the Z-axis direction at a distal end 102 of the surgical robot arm 100 is formed to be greater than a height of the first yaw axis Y1 in the Z-axis direction at a proximal end 101 of the surgical robot arm 100. Here, in the surgical robot arm 100, the body 110 or a region adjacent to the body 110 is defined as the proximal end 101, and a region farthest from the body 110, for example, an end portion of the surgical instrument 200 at an end tool 210 side in the fifth link 160, may be defined as the distal end 102.

In other words, it may be described that the base link 115 is formed to be inclined at a predetermined angle with respect to the horizontal plane, so that a central axis of the base link 115 is formed to coincide with the first yaw axis Y1.

By forming the first yaw axis Y1 and the extension line connecting the third joint 173 to the RCM to be different from each other as described above, the fifth link 160 and the surgical instrument 200 coupled thereto can be disposed in the horizontal direction without inducing a gimbal lock phenomenon.

Here, when the first link 120 rotates around the first yaw axis Y1 with respect to the base link 115, the second link 140, the third link 140, the fourth link 150, the fifth link 160, and the surgical instrument 200 that are connected to the first link 120 rotate around the first yaw axis Y1 together with the first link 120. Accordingly, a coordinate system of the surgical instrument 200 and each of the links is not fixed but is relatively continuously changed according to the rotation of the first link 120. That is, in FIG. 3 or the like, the second link 130 is illustrated as being parallel to the X-axis. However, when the first link 120 rotates, the coordinate system of the second link 130 and each link connected to the second link 130 also rotates together with the first link 120. However, for convenience of description, in the present specification, unless described otherwise, the description will be provided based on the state in which the second link 130 is positioned parallel to the X-axis as shown in FIG. 3.

Meanwhile, the second joint 172 connects the second link 130 to the first link 120. In this case, since the second link 130 is fixedly coupled the first link 120, a relative position of the second link 130 with respect to the first link 120 may be formed to be constant. That is, the second link 130 and the first link 120 may operate together as one body. Here, the second link 130 and the first link 120 are illustrated as being formed as separate members and fixedly coupled to each other, but the concept of the present disclosure is not limited thereto, and it would also be possible that the second link 130 and the first link 120 are integrally formed and function as the yaw drive assembly 105.

Here, the second link 130 of the first embodiment of the present disclosure may be formed parallel to the horizontal plane. Alternatively, the second link 130 may be formed substantially parallel to the fourth link 150 to be described later. Alternatively, the second link 130 may be disposed on or parallel to the extension line of the third joint 173 and the RCM.

Here, the second joint 172 may include a motor, and may be connected to the third joint 173 by a belt, a wire, or the like. Accordingly, a driving force of the second joint 172 may be transmitted to the third joint 173. Alternatively, the second joint 172 may not include a motor, and the third joint 173 may be formed to include a motor.

The third link 140 is axially coupled to the second link 130 so as to be rotatable around the third joint 173 with respect to the second link 130. Here, the third joint 173 may include one or more pulleys.

The fourth link 150 is axially coupled to the third link 140 so as to be rotatable around the fourth joint 174 with respect to the third link 140. Here, the fourth joint 174 may include one or more pulleys.

The fifth link 160 is axially coupled to the fourth link 150 so as to be rotatable around the fifth joint 175 with respect to the fourth link 150. Here, the fifth joint 175 may include one or more pulleys.

The surgical instrument 200 is coupled to the fifth link 160. In this case, at least a portion of the surgical instrument 200 is formed to be rotatable around the roll axis (i.e., a shaft axis), and is formed to be linearly reciprocally movable along a roll axis R with respect to the fifth link 160. Here, the roll axis R of the surgical instrument 200 is formed to pass through the RCM.

Meanwhile, although not shown in the drawings, an instrument mounting part (not shown) and a guide rail (not shown) are formed in the fifth link 160, which is an instrument mounting link, and the instrument mounting part (not shown) may linearly move along the guide rail (not shown), which is formed in a direction of the roll axis R, in a state in which the surgical instrument 200 is mounted on the instrument mounting part (not shown). In order to implement such a linear movement, a linear actuator (not shown) may be provided in the instrument mounting part (not shown).

In addition, the surgical instrument 200 may be mounted on the above-described instrument mounting part (not shown) of the fifth link 160 of the surgical robot arm 100.

Meanwhile, an interface part (not shown) coupled to the surgical instrument 200 and configured to control the movement of the surgical instrument 200 may be further formed in the instrument mounting part (not shown). In the interface part (not shown), a component for coupling with a driving part of the surgical instrument 200 and a motor for transmitting a driving force from the surgical robot arm 100 to the surgical instrument 200 may be provided. Due to the interface part (not shown), the end tool of the surgical instrument 200 may perform pitch, yaw, and actuation motions. Furthermore, due to the interface part (not shown), the shaft and end tool of the surgical instrument 200 may perform a roll motion around the roll axis R.

Meanwhile, the trocar 300 serving as an insertion path, through which the surgical instrument 200 inserted into a patient's body, may be coupled to the fifth link 160, which is an instrument mounting link, and the surgical instrument 200 may be inserted into the patient's body through the trocar 300 while the trocar 300 is inserted into the body. In addition, the above-described RCM may be formed at a predetermined position on the trocar 300. In addition, as described above, the first yaw axis Y1 of the base link 115 may be formed to pass through the RCM.

In addition, the surgical instrument 200 may further include a driving part (not shown). In the driving part (not shown), a component for coupling with the interface part (not shown), a driving wheel operated by being engaged with the motor, and the like may be formed. In addition, a coupling member and a drive transmission member may be correspondingly formed on the interface part (not shown) and the driving part (not shown), respectively, which allows the surgical instrument 200 to operate by receiving a driving force from the surgical robot arm 100 while mounted on the fifth link 160.

Here, the third joint 173, the fourth joint 174, the fifth joint 175, and the RCM may be four vertices of a parallelogram. That is, the third joint 173, the fourth joint 174, the fifth joint 175, and the RCM may form a single parallelogram.

In detail, when three vertices, which are the third joint 173, the fourth joint 174, and the fifth joint 175, are established, the position of the RCM in the parallelogram including these three vertices is automatically defined.

In addition, when the third link 140 rotates around the third joint 173 in a state in which the position of the third joint 173 is fixed, due to the RCM mechanism of a link/belt to be described later, the third link 140 and the fifth link 160 rotate while maintaining a parallel state, and the fourth link 150 and the extension line connecting the third joint 173 to the RCM also rotate while maintaining a parallel state. Accordingly, the RCM may remain constant in position regardless of the rotation angle of the third link 140.

In this structure, once the surgical robot arm is set up, the RCM always maintains its position. In addition, whenever each of the links rotates around the RCM, regardless of its position, the links maintain the parallelogram. That is, in a state in which the body 110 and the base link 115 are fixed, the position of the RCM will not change no matter where the third link 140 or the fifth link 160 is positioned, and the third joint 173, the fourth joint 174, the fifth joint 175, and the RCM maintain the parallelogram.

In order to maintain the RCM as described above, the fourth joint 174 and the fifth joint 175 are connected to each other to be rotatable around the third joint 173. Various power transmission devices, such as belts, wires, and links, may be used to connect the third joint 173, the fourth joint 174, and the fifth joint 175 to each other.

For example, a rotation of the third joint 173 and a rotation of the fourth joint 174 may be interlocked by a belt, so that a rotation of the third joint 173 with respect to the second link 130 may cause a rotation of the fourth link 150 with respect to the third link 140. At the same time, the rotation of the fourth joint 174 and a rotation of the fifth joint 175 may be interlocked by a belt, so that the rotation of the fourth link 150 with respect to the third link 140 may cause a rotation of the fifth link 160 with respect to the fourth link 150. As a result, with this configuration, a line segment connecting the third joint 173 to the fourth joint 174 and a line segment connecting the fifth joint 175 to the RCM may always remain parallel. In addition, a line segment connecting the third joint 173 to the RCM, and a line segment connecting the fourth joint 174 to the fifth joint 175 may also always remain parallel.

(Meanwhile, although not shown in the drawings, it is also possible to have a configuration in which the first link 120 and the third link 140 are connected directly by the second joint 172, without having the second link 130 and the third joint 173.)

Meanwhile, in the first embodiment of the present disclosure, each of the links, in particular, the second link 130, the third link 140, the fourth link 150, and the fifth link 160 are arranged side by side without overlapping each other, so that no collision occurs when one link rotates with respect to another link. In addition, the links are formed in such a manner that no one link interferes with the rotation of another link, so that a driving range of each link is increased.

In detail, referring to FIG. 9B, which is a plan view of the surgical robot arm 100 according to an embodiment of the present disclosure, or the like, when viewed from the XY plane, each of the second link 130, the third link 140, the fourth link 150, and the fifth link 160 is formed to be offset by a certain degree in a direction of the rotation axes thereof (i.e., a Y-axis direction). In other words, based on the Y-axis direction, the third link 140 is disposed on one side of the second link 130, the fourth link 150 is disposed on one side of the third link 140, and the fifth link 160 is disposed on one side of the fourth link 150. In other words, it may be expressed that the second link 130, the third link 140, the fourth link 150, and the fifth link 160 are sequentially arranged in the Y-axis direction.

In particular, by disposing the fifth link 160, on which the surgical instrument 200 is mounted, to be offset by a certain degree with respect to the fourth link 150, a restriction on the rotation angle of the fifth link 160 (and the surgical instrument 200 coupled thereto) with respect to the fourth link 150 is eliminated, thereby achieving an effect of allowing the fifth link 160 (and the surgical instrument 200 coupled thereto) to rotate freely.

Meanwhile, from another perspective, it may be said that since the links are formed in such a manner that no one link interferes with the rotation of another link, at least a portion of each of the links may overlap each other in the direction of the first yaw axis Y1. That is, as shown in FIG. 11, in a state in which the surgical robot arm 100 is folded to a certain degree, based on the direction of the first yaw axis Y1, the second link 130 and the third link 140 are arranged to overlap each other by a certain degree, the third link 140 and the fourth link 150 are arranged to overlap each other by a certain degree, and the fourth link 150 and the fifth link 160 are arranged to overlap each other by a certain degree.

Meanwhile, in the first embodiment of the present disclosure, the surgical instrument 200 coupled to the fifth link 160 is disposed to face outwardly of the surgical robot arm 100.

In detail, in the fifth link 160, a surface on which the instrument mounting part is formed, or, in other words, a surface to which the surgical instrument 200 is coupled is assumed to be a first surface, and a surface opposite to the surface is assumed to be a second surface.

At this time, in a state in which the end tool 210 of the surgical instrument 200 coupled to the fifth link 160 faces vertically downward, the first surface is disposed to face a direction away from the body 110. In other words, the surgical instrument 200 coupled to the first surface of the fifth link 160 is disposed farther from the body 110 than the fifth link 160.

Meanwhile, in a state in which the surgical instrument 200 coupled to the fifth link 160 is horizontally disposed and the end tool 210 is disposed in a direction away from the body 110, the first surface is disposed to face upward. In other words, the surgical instrument 200 coupled to the first surface of the fifth link 160 is disposed above the fifth link 160.

(Conceptual View of RCM-Link Structure)

As an example of the RCM mechanism of the present disclosure, a link structure may be applied.

FIG. 5 is a view illustrating an example in which an RCM mechanism of a link structure is applied to the surgical robot arm of FIG. 2, and FIG. 6 is a view illustrating motion states of the RCM mechanism of a link structure.

In the case of such a link structure, the surgical robot arm 100 according to the first embodiment of the present disclosure includes the first link 120, the second link 130, the third link 140, the fourth link 150, and the fifth link 160. In addition, the surgical robot arm 100 further includes a third-first link 140-1 and a fourth-first link 150-1. In addition, the surgical robot arm 100 may include the first joint 171, the second joint 172, the third joint 173, the fourth joint 174, and the fifth joint 175.

First, when the third link 140 rotates around the third joint 173 with respect to the second link 130, the fourth link 150 and the third-first link 140-1 forming a parallelogram together therewith rotate together. At this time, even when the links rotate, the parallelogram is maintained, and thus the third link 140 and the third-first link 140-1 remain parallel in any rotation state.

Meanwhile, when the fourth link 150 rotates around the fourth joint 174 with respect to the third link 140, the third link 140, the fifth link 160, and the fourth-first link 150-1 forming a parallelogram together therewith rotates together. At this time, even when the links rotate, the parallelogram is maintained, and thus the fourth link 150 and the fourth-first link 150-1 remain parallel in any rotation state.

As described above, in conjunction with the rotation of the third link 140 around the third joint 173, the fourth link 150 also rotates with respect to the third link 140, so that the fourth link 150 and the extension line connecting the third joint 173 to the RCM maintain a parallel state.

Similarly, in conjunction with the rotation of the fourth link 150 with respect to the third link 140, the fifth link 160 also rotates with respect to the fourth link 150, so that the third link 140 and the fifth link 160 maintain a parallel state.

As a result, the RCM remains constant regardless of the motion state.

(Conceptual View of RCM-Belt Structure)

As an example of the RCM mechanism of the present disclosure, a belt structure may be applied.

FIG. 7 is a view illustrating an example in which an RCM mechanism of a belt structure is applied to the surgical robot arm of FIG. 2, and FIG. 8 is a view illustrating motion states of the RCM mechanism of a belt structure.

In the case of such a belt structure, the surgical robot arm 100 according to the first embodiment of the present disclosure includes the first link 120, the second link 130, the third link 140, the fourth link 150, and the fifth link 160.

In addition, the surgical robot arm 100 may include the first joint 171, the second joint 172, the third joint 173, the fourth joint 174, and the fifth joint 175. Here, the second joint 172 may include a pulley 192, the third joint 173 may include a pulley 193-1 and a pulley 193-2, the fourth joint 174 may include a pulley 194-1 and a pulley 194-2, and the fifth joint 175 may include a pulley 195.

Here, each of the pulley 192, the pulley 193-1, the pulley 194-1, and the pulley 195 may be a rotation pulley that rotates around a central axis thereof. Meanwhile, the pulley 193-2 and the pulley 194-2 may be fixed pulleys that do not rotate.

Further, the surgical robot arm 100 may include a first belt 181, a second belt 182, and a third belt 183.

Here, the first belt 181 may connect the pulley 192 to the pulley 193-1. The second belt 182 may connect the pulley 193-2 to the pulley 194-1. The third belt 183 may connect the pulley 194-2 to the pulley 195.

Here, the pulley 192, which is a rotation pulley, may be connected to a motor (not shown) and may be formed to be rotatable with respect to the second link 130. In addition, it may be assumed that each pulley and each belt are fixedly coupled at one or more points so that no slippage occurs.

First, the pulley 193-1, which is a rotation pulley, is formed to be rotatable with respect to the second link 130, and is integrally formed with the third link 140. Thus, when the pulley 193-1 rotates with respect to the second link 130, the third link 140, which is integrally formed with the pulley 193-1, rotates with respect to the second link 130.

Meanwhile, the pulley 193-2, which is a fixed pulley, is integrally formed with the second link 130.

Meanwhile, the pulley 194-1, which is a rotation pulley, is formed to be rotatable with respect to the third link 140, and is integrally formed with the fourth link 150. Thus, when the pulley 194-1 rotates with respect to the third link 140, the fourth link 150, which is integrally formed with the pulley 194-1, rotates with respect to the third link 140.

Meanwhile, the fixed pulley 194-2 is integrally formed with the third link 140.

Meanwhile, the pulley 195, which is a rotation pulley, is formed to be rotatable with respect to the fourth link 150, and is integrally formed with the fifth link 160. Thus, when the pulley 195 rotates with respect to the fourth link 150, the fifth link 160, which is integrally formed with the pulley 195, rotates with respect to the fourth link 150.

In this case, the two pulleys belted together must have diameters equal to each other so that the RCM is maintained. That is, {diameter of pulley 192=diameter of pulley 193-1}, {diameter of pulley 193-2=diameter of pulley 194-1}, and {diameter of pulley 194-2=diameter of pulley 195} should be satisfied.

Operations of the above-described belt-structured RCM mechanism will be described.

First, when the pulley 192 connected to the motor (not shown) rotates, the pulley 193-1 connected to the pulley 192 through the belt 181 also rotates.

In addition, when the pulley 193-1 rotates, the third link 140 integrally formed with the pulley 193-1 rotates with respect to the second link 130.

In this case, since the third link 140 rotates with respect to the second link 130 in a state in which the pulley 193-2 is fixed to the second link 130, the belt 182 rotates relative to the pulley 193-2.

In addition, when the belt 182 rotates, the pulley 194-1 rotates with respect to the third link 140, and when the pulley 194-1 rotates, the fourth link 150 integrally formed with the pulley 194-1 rotates with respect to the third link 140.

As described above, in conjunction with the rotation of the third link 140 around the second link 130, the fourth link 150 also rotates with respect to the third link 140, so that the fourth link 150 and the extension line connecting the third joint 173 to the RCM maintain a parallel state.

In addition, since the fourth link 150 rotates with respect to the third link 140 in a state in which the pulley 194-2 is fixed to the third link 140, the belt 183 rotates relative to the pulley 194-2.

In addition, when the belt 183 rotates, the pulley 195 rotates with respect to the fourth link 150, and when the pulley 195 rotates, the fifth link 160 integrally formed with the pulley 195 rotates with respect to the fourth link 150.

As described above, in conjunction with the rotation of the fourth link 150 with respect to the third link 140, the fifth link 160 also rotates with respect to the fourth link 150, so that the third link 140 and the fifth link 160 maintain a parallel state.

As a result, the RCM remains constant regardless of the motion state.

Operations of Surgical Robot Arm

FIGS. 9 to 11 are views illustrating an RCM motion (pitch motion) of the surgical robot arm of FIG. 3 around a pitch axis P, each view including both a side view and a plan view.

As shown in FIGS. 9 to 11, when a motor (not shown) is driven, the third link 140 rotates around the third joint (see 173 in FIG. 4) with respect to the second link 130. In addition, in conjunction therewith, the fourth link 150 rotates with respect to the third link 140, and the fifth link 160 rotates with respect to the fourth link 150. At this time, due to the above-described belt or link structure, the fourth link 150 and the extension line connecting the third joint 173 to the RCM maintain a parallel state, and the third link 140 and the fifth link 160 maintain a parallel state. In other words, the RCM remains constant even in any state of motion of the surgical robot arm 100 around the pitch axis P.

Meanwhile, as shown in the plan view of each drawing, the second link 130, the third link 140, the fourth link 150, and the fifth link 160 may be disposed to be adjacent to each other without overlapping each other in the Y-axis direction.

FIGS. 12 to 14 are perspective views illustrating an RCM motion (a yaw motion) of the surgical robot arm of FIG. 3 around the first yaw axis Y1.

As shown in FIGS. 12 to 14, when a motor (not shown) is driven, the first link 120 of the yaw drive assembly 105 rotates around the first yaw axis Y1 with respect to the base link 115. At this time, since the first yaw axis Y1 passes through the RCM, the RCM remains constant no matter what angle the first link 120 rotates with respect to the base link 115.

FIG. 15 is a view illustrating a state in which the fifth link 160 of the surgical robot arm 100 of FIG. 3 and the surgical instrument 200 coupled thereto are disposed parallel to each other.

As described above, the surgical robot arm 100 according to the first embodiment of the present disclosure is formed such that the first yaw axis Y1 and the extension line connecting the third joint 173 to the RCM are different from each other, so that the fifth link 160 and the surgical instrument 200 coupled thereto can be disposed in the horizontal direction without inducing a gimbal lock phenomenon.

FIG. 16 is a view illustrating a state in which the surgical robot arm 100 illustrated in FIG. 15 is disposed near the patient's surgical site, and the surgical instrument 200 is disposed directly facing the patient.

As described above, in the surgical robot arm 100 according to the first embodiment of the present disclosure, each robot arm is formed in a modular manner, and the fifth link 160 and the surgical instrument 200 coupled thereto may be disposed parallel to each other. Accordingly, each modular surgical robot arm 100 may be disposed near the patient's surgical site, and the surgical instrument 200 may be disposed directly facing the patient.

FIG. 17 is a view illustrating a state in which the end tool 210 of the surgical instrument 200 coupled to the fifth link 160 of the surgical robot arm 100 of FIG. 3 is disposed facing upward from below.

As described above, the surgical robot arm 100 according to the first embodiment of the present disclosure is formed such that the first yaw axis Y1 and the extension line connecting the third joint 173 to the RCM intersect each other at the RCM, so that the surgical instrument 200 can be disposed facing upward from below, beyond the horizontal direction.

According to the first embodiment of the present disclosure described above, by forming the first yaw axis Y1 and the extension line connecting the third joint 173 to the RCM to be different from each other, the fifth link 160 and the surgical instrument 200 coupled thereto can be disposed in the horizontal direction without inducing a gimbal lock phenomenon. Furthermore, the surgical instrument 200 can be disposed facing upward from below, beyond the horizontal direction.

Further, by disposing each of the links to be offset by a certain degree, the rotational motion of each link is not constrained by another link, so that the range of motion of the instrument is increased, such as the moving direction of the instrument is directed upward beyond the horizontal direction. Accordingly, even in the frequent case of surgery, in which the instrument is disposed in the horizontal direction, an effect of preventing the gimbal lock and allowing the instrument to move with a sufficient range of motion may be obtained.

<Second Embodiment of Surgical Robot Arm>

Hereinafter, a surgical robot arm 500 according to a second embodiment of the present disclosure will be described. Here, the surgical robot arm 500 according to the second embodiment of the present disclosure is different from the surgical robot arm (see 100 in FIG. 3 or the like) according to the first embodiment of the present disclosure described above in that the number of yaw axes is changed and the configuration of a yaw drive assembly 505 is changed accordingly. Such a configuration that is changed from that of the first embodiment will be described in detail below.

Figure 18:
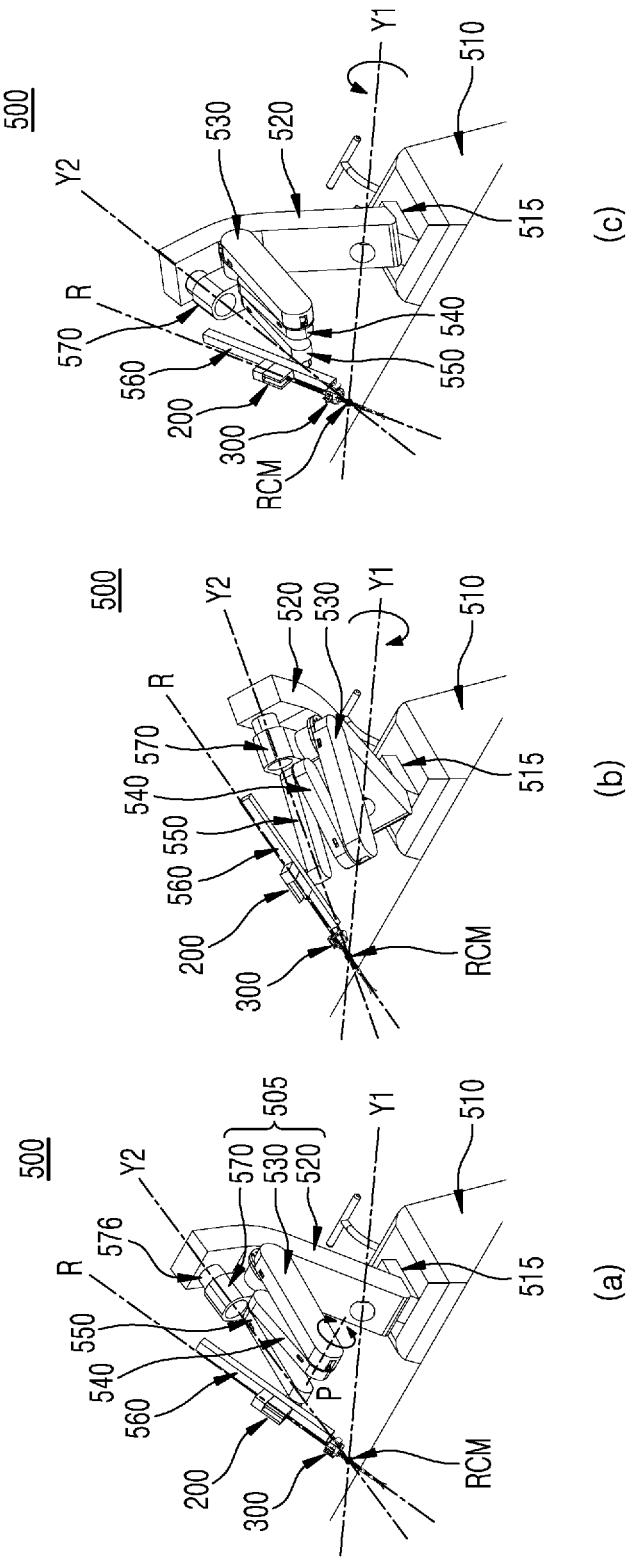
FIG. 18 is a perspective view illustrating the surgical robot arm according to the second embodiment of the present disclosure, and is a view illustrating an RCM motion (yaw motion) of the surgical robot arm around a first yaw axis Y1.

FIG. 18 is a perspective view illustrating the surgical robot arm according to the second embodiment of the present disclosure, and is a view illustrating an RCM motion (yaw motion) of the surgical robot arm around a first yaw axis Y1.

Referring to FIG. 18, the surgical robot arm 500 according to the second embodiment of the present disclosure includes a body 510, a base link 515, a yaw drive assembly 505, a third link 540, a fourth link 550, and a fifth link 560. Here, the yaw drive assembly 505 may include a first link 520, a second link 530, and a sixth link 570. In addition, as in the first embodiment illustrated with reference to FIG. 3, the surgical robot arm 500 of the present embodiment may include a first joint (see 171 in FIG. 4), a second joint (see 172 in FIG. 4), a third joint (see 173 in FIG. 4), a fourth joint (see 174 in FIG. 4), and a fifth joint (see 175 in FIG. 4). In addition, the surgical robot arm 500 of the present embodiment may further include a sixth joint 576. In addition, a trocar 300 and a surgical instrument 200 are coupled to the fifth link 560 of the surgical robot arm 500 described above.

Here, the body 510 serves as a base of the entire surgical robot arm 500.

Meanwhile, the base link 515 may be formed on one surface of the body 510, for example, an upper surface thereof. The base link 515 may be formed to be inclined by a certain degree to have a predetermined angle with respect to a horizontal plane.

Meanwhile, the yaw drive assembly 505 is rotatably coupled to the base link 515. The yaw drive assembly 505 is coupled to the base link 515 by the first joint (see 171 in FIG. 4), and formed to be yaw rotatable around the first yaw axis Y1 with respect to the base link 515.

Here, the yaw drive assembly 505 may include the first link 520 and the second link 530. Furthermore, the yaw drive assembly 505 of the surgical robot arm 500 according to the second embodiment of the present disclosure may further include the sixth link 570 connecting the first link 520 to the second link 530. This will be described in more detail later.

The third link 540 is axially coupled to the second link 530 so as to be rotatable around the third joint (see 173 in FIG. 4) with respect to the second link 530. Here, the third joint (sec 173 in FIG. 4) may include one or more pulleys.

The fourth link 550 is axially coupled to the third link 540 so as to be rotatable around the fourth joint (see 174 in FIG. 4) with respect to the third link 540. Here, the fourth joint (see 174 in FIG. 4) may include one or more pulleys.

The fifth link 560 is axially coupled to the fourth link 550 so as to be rotatable around the fifth joint (see 175 in FIG. 4) with respect to the fourth link 550. Here, the fifth joint (see 175 in FIG. 4) may include one or more pulleys.

The surgical instrument 200 is coupled to the fifth link 560.

Here, the third link 540, the fourth link 550, and the fifth link 560 form a parallelogram, and configure a kind of RCM mechanism. That is, when the third link 540 rotates around the third joint (see 173 in FIG. 4) in a state in which the position of the third joint (sec 173 in FIG. 4) is fixed, due to the RCM mechanism of a link/belt described above, the third link 540 and the fifth link 560 rotate while maintaining a parallel state, and the fourth link 550 and an extension line connecting the third joint (see 173 in FIG. 4) to an RCM also rotate while maintaining a parallel state. Accordingly, the RCM may remain constant in position regardless of the rotation angle of the third link 540.

Here, the surgical robot arm 500 according to the second embodiment of the present disclosure includes two yaw axes, i.e., the first yaw axis Y1 and a second yaw axis Y2. That is, by having the first yaw axis Y1 and the second yaw axis Y2 that are rotatable independently of each other, a yaw motion may be performed around the second yaw axis Y2 when a roll axis R and the first yaw axis Y1 coincide with each other, and a yaw motion may be performed around the first yaw axis Y1 when the roll axis R and the second yaw axis Y2 coincide with each other. This will be described in more detail below.

The yaw drive assembly 505 of the surgical robot arm 500 according to the second embodiment of the present disclosure may include the first link 520 and the second link 530. In addition, the yaw drive assembly 505 of the surgical robot arm 500 according to the second embodiment of the present disclosure may further include the sixth link 570 connecting the first link 520 to the second link 530.

The yaw drive assembly 505 is coupled to the base link 515 by the first joint (see 171 in FIG. 4), and formed to be yaw rotatable around the first yaw axis Y1 with respect to the base link 515.

Here, the first link 520 is coupled to the base link 515 by the first joint (see 171 in FIG. 4), and formed to be yaw rotatable around the first yaw axis Y1 with respect to the base link 515. Here, the RCM may be positioned on an extension line of the first yaw axis Y1.

Meanwhile, the sixth link 570 is coupled to the first link 520 by the sixth joint 576, and formed to be yaw rotatable around the second yaw axis Y2 with respect to the first link 520.

Meanwhile, one end portion of the second link 530 is fixedly coupled to the sixth link 570, and another end portion thereof is coupled to the third link 540.

Here, the RCM may be positioned on an extension line of the second yaw axis Y2. In other words, the extension line of the first yaw axis Y1 and the extension line Y2 of the second yaw axis may meet at the RCM. In this case, the first link 520 formed to be yaw rotatable around the first yaw axis Y1 and the sixth link 570 formed to be yaw rotatable around the second yaw axis Y2 may be formed to be rotatable independently of each other.

With this configuration, the yaw motion of the present embodiment may be performed by the first link 520 that yaw-rotates around the first yaw axis Y1 with respect to the base link 515, or may be performed by the sixth link 570 that yaw-rotates around the second yaw axis Y2 with respect to the first link 520.

That is, by having the first yaw axis Y1 and the second yaw axis Y2 that are rotatable independently of each other, a yaw motion is performed around the second yaw axis Y2 when the roll axis R and the first yaw axis Y1 coincide with each other, and a yaw motion is performed around the first yaw axis Y1 when the roll axis R and the second yaw axis Y2 coincide with each other.

By having two yaw axes as described above, when one of the yaw axes coincides with the roll axis and thus there is a possibility that a gimbal lock phenomenon occurs, the yaw motion may be performed using the other yaw axis. Thus, even when each link of the surgical robot arm 500 is in any motion state, it is possible to obtain an effect of performing a desired motion without inducing a gimbal lock phenomenon.

FIG. 18 is a perspective view illustrating an RCM motion (yaw motion) of the surgical robot arm 500 around the first yaw axis Y1 according to the second embodiment of the present disclosure. Here, FIG. 18 illustrates a state in which both the first yaw axis Y1 and the second yaw axis Y2 do not coincide with the roll axis R. In this case, the yaw motion may be performed by rotating the first link 520 around the first yaw axis Y1 with respect to the base link 515.

Figure 19:
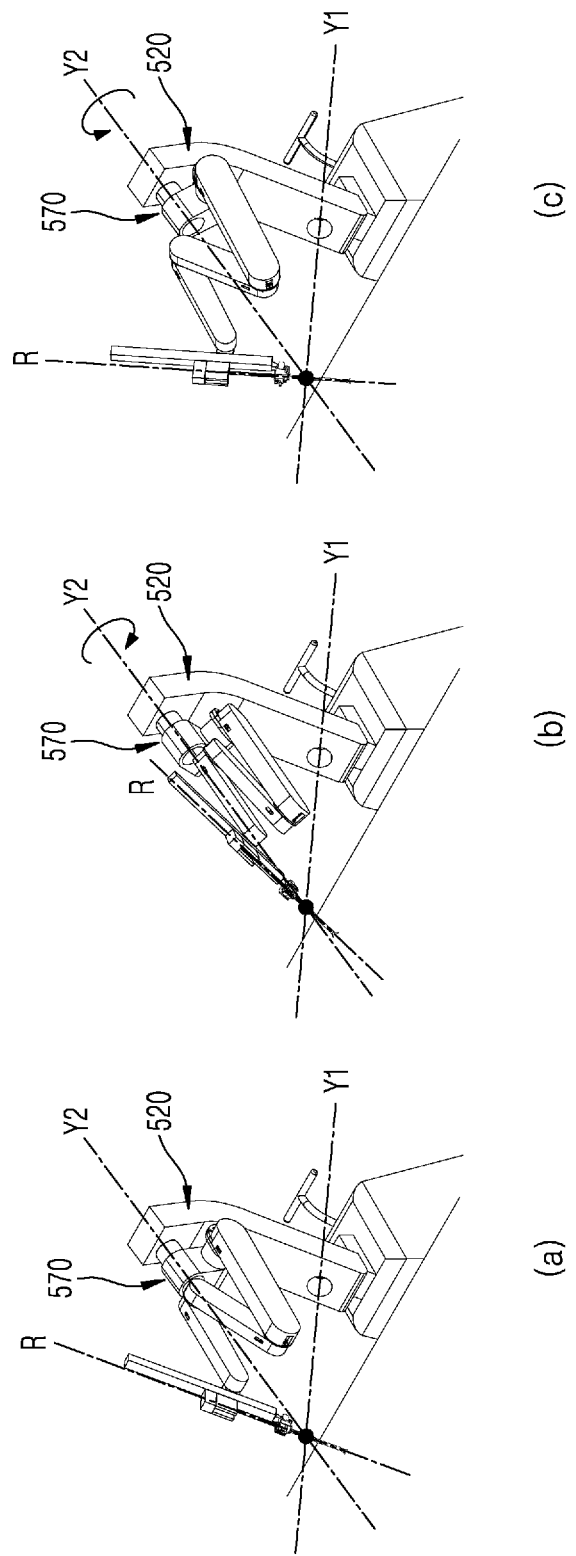
FIGS. 19A to 19C are perspective views illustrating an RCM motion (yaw motion) of the surgical robot arm of FIG. 18 around a second yaw axis Y2.

FIGS. 19A to 19C are perspective views illustrating an RCM motion (yaw motion) of the surgical robot arm of FIG. 18 around the second yaw axis Y2. As in FIG. 18, FIG. 19 also illustrates a state in which both the first yaw axis Y1 and the second yaw axis Y2 do not coincide with the roll axis R. In this case, the yaw motion may be performed by rotating the sixth link 570 around the second yaw axis Y2 with respect to the first link 520.

FIG. 20 is a set of a plan view and a side view illustrating a state in which the surgical robot arm in FIG. 19B rotates further around the second yaw axis Y2 by approximately 90°. Since the surgical robot arm 500 according to the second embodiment of the present disclosure has two yaw axes as described above, in the surgical robot arm 500, a greater variety of motion states are possible.

Figure 21:
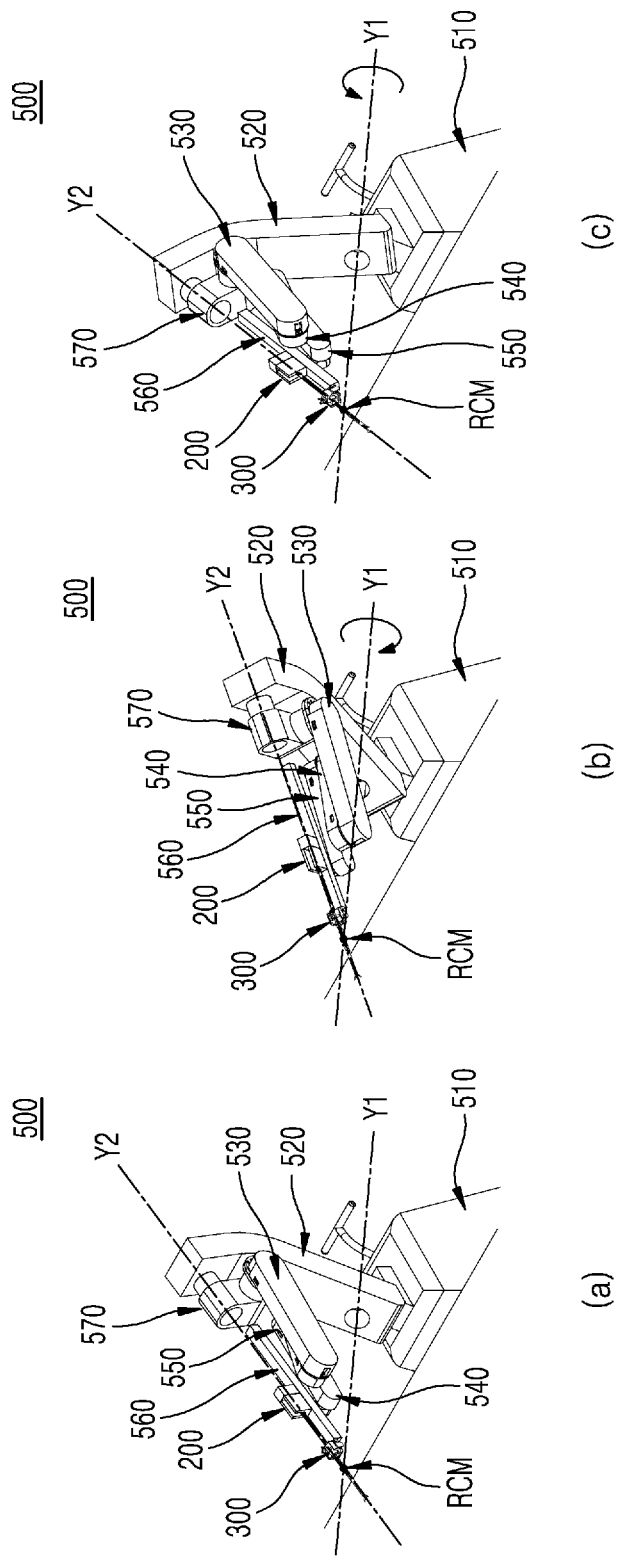
FIG. 21 is a perspective view illustrating an RCM motion (yaw motion) of the surgical robot arm of FIG. 18 around the second yaw axis Y2.

FIG. 21 is a perspective view illustrating an RCM motion (yaw motion) of the surgical robot arm of FIG. 18 around the second yaw axis Y2. Here, FIG. 21 illustrates a state in which the second yaw axis Y2 coincides with the roll axis R. In this case, the yaw motion may be performed by rotating the first link 520 around the first yaw axis Y1 with respect to the base link 515.

Figure 22:
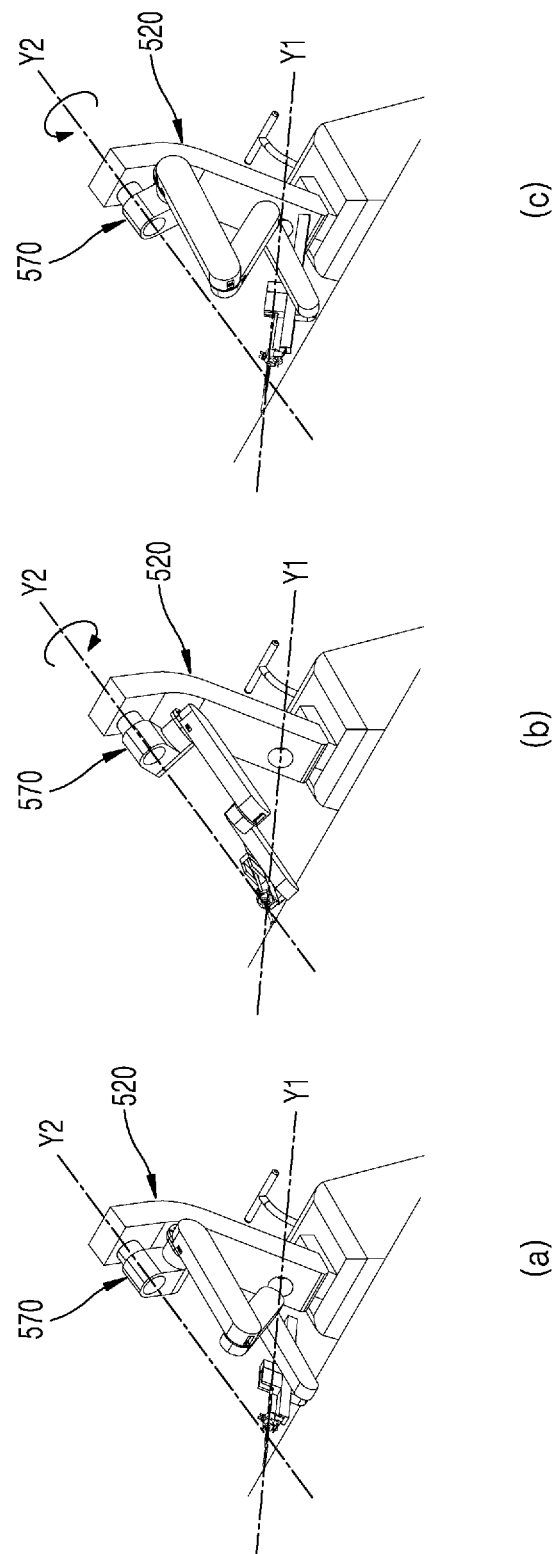
FIG. 22 is a perspective view illustrating an RCM motion (yaw motion) of the surgical robot arm of FIG. 18 around the first yaw axis Y1.

FIG. 22 is a perspective view illustrating an RCM motion (yaw motion) of the surgical robot arm of FIG. 18 around the first yaw axis Y1. Here, FIG. 22 illustrates a state in which the first yaw axis Y1 coincides with the roll axis R. In this case, the yaw motion may be performed by rotating the sixth link 570 around the second yaw axis Y2 with respect to the first link 520.

Figure 23:
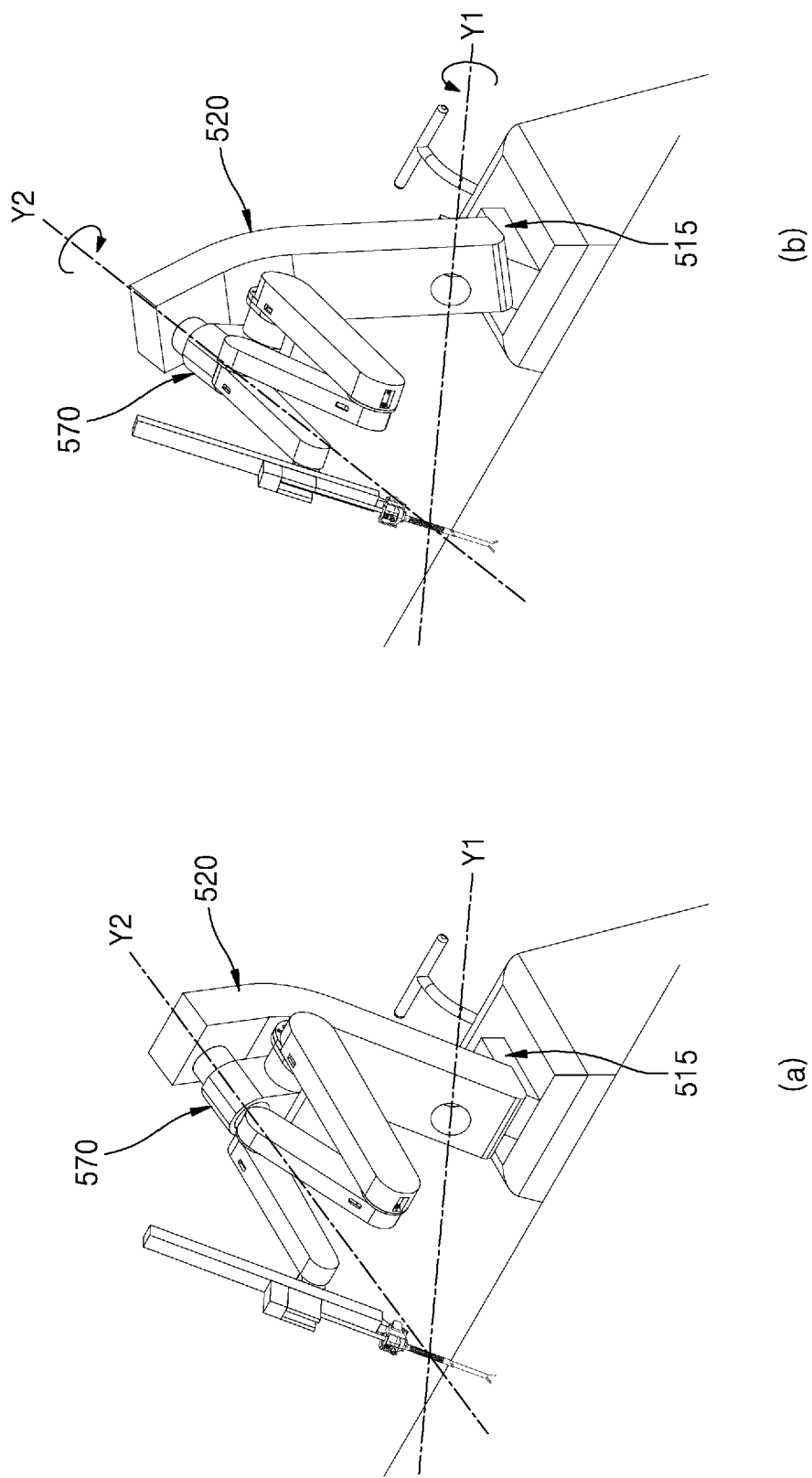
FIG. 23 is a perspective view illustrating an RCM motion (yaw motion) of the surgical robot arm of FIG. 18 around the first yaw axis Y1 and the second yaw axis Y2.

FIG. 23 is a perspective view illustrating an RCM motion (yaw motion) of the surgical robot arm of FIG. 18 around the first yaw axis Y1 and the second yaw axis Y2. Here, FIG. 23 illustrates a state in which both the first yaw axis Y1 and the second yaw axis Y2 do not coincide with the roll axis R. In this case, the yaw motion may be performed by combining two motions. That is, a yaw motion may also be performed by combining the motion of rotation of the first link 520 around the first yaw axis Y1 with respect to the base link 515 with the motion of rotation of the sixth link 570 around the second yaw axis Y2 with respect to the first link 520.

According to the present disclosure described above, even when each link of the surgical robot arm 500 is in any motion state, it is possible to obtain an effect of performing a desired motion without inducing a gimbal lock phenomenon.

<Third Embodiment of Surgical Robot Arm>

Hereinafter, a surgical robot arm 600 according to a third embodiment of the present disclosure will be described. Here, the surgical robot arm 600 according to the third embodiment of the present disclosure is different from the surgical robot arm (see 100 in FIG. 3 or the like) according to the first embodiment of the present disclosure described above in that a setup link assembly 690 is further included. Such a configuration that is changed from that of the first embodiment will be described in detail below.

Figure 24:
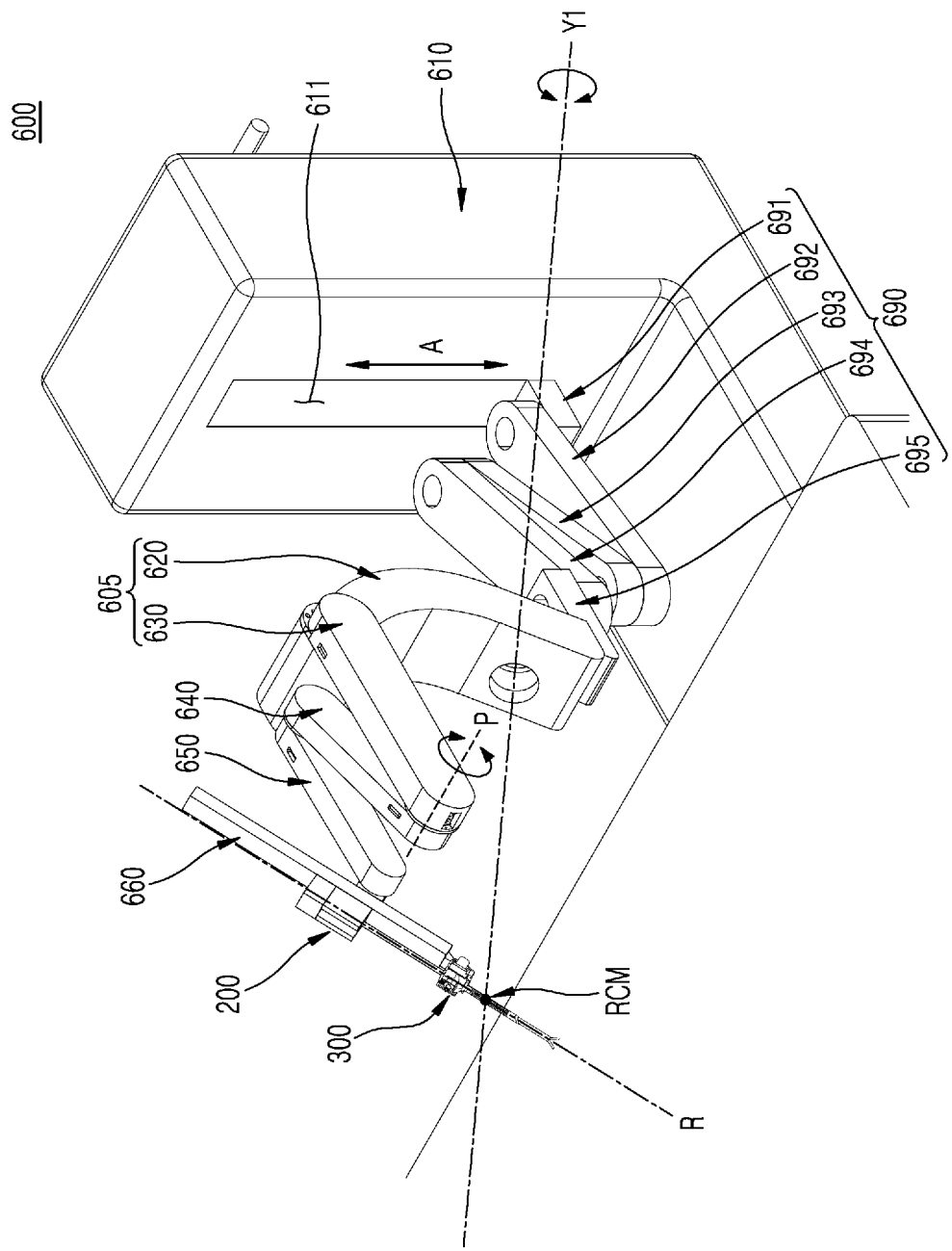
FIG. 24 is a perspective view illustrating a surgical robot arm according to a third embodiment of the present disclosure.
Figure 25:
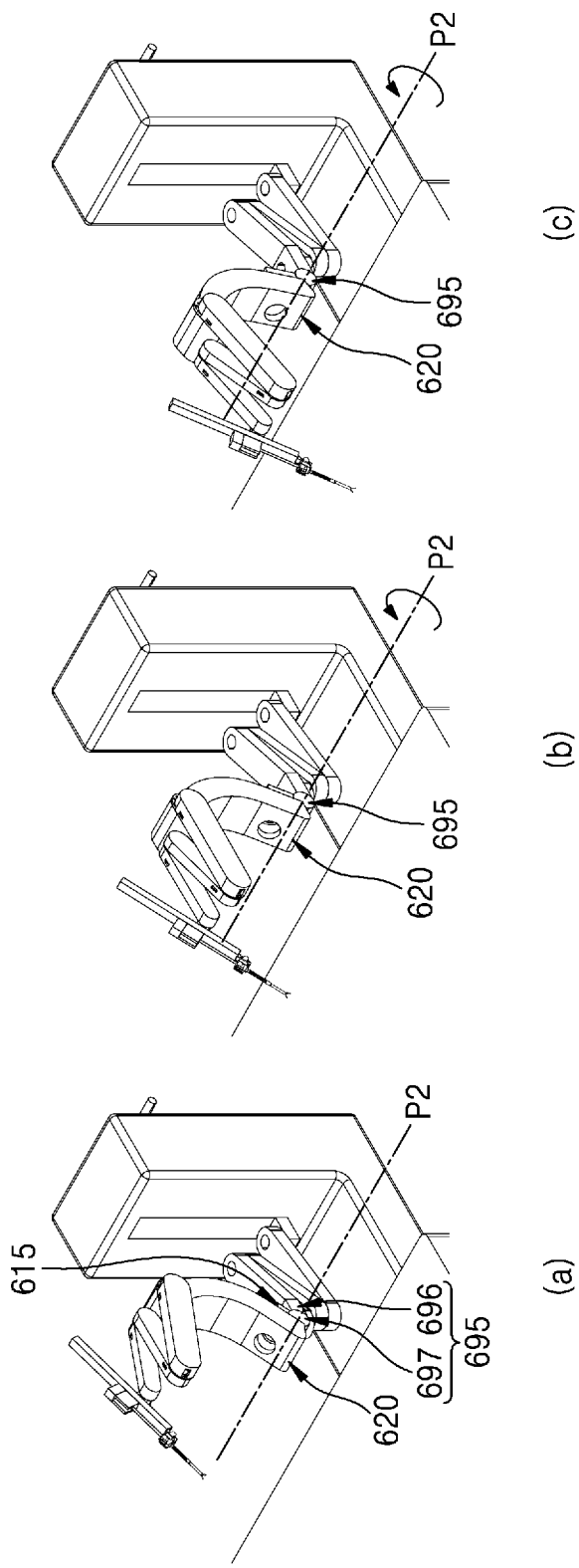
FIG. 25 is a perspective view illustrating operations of a pitch positioning joint of the surgical robot arm of FIG. 24.
Figure 26:
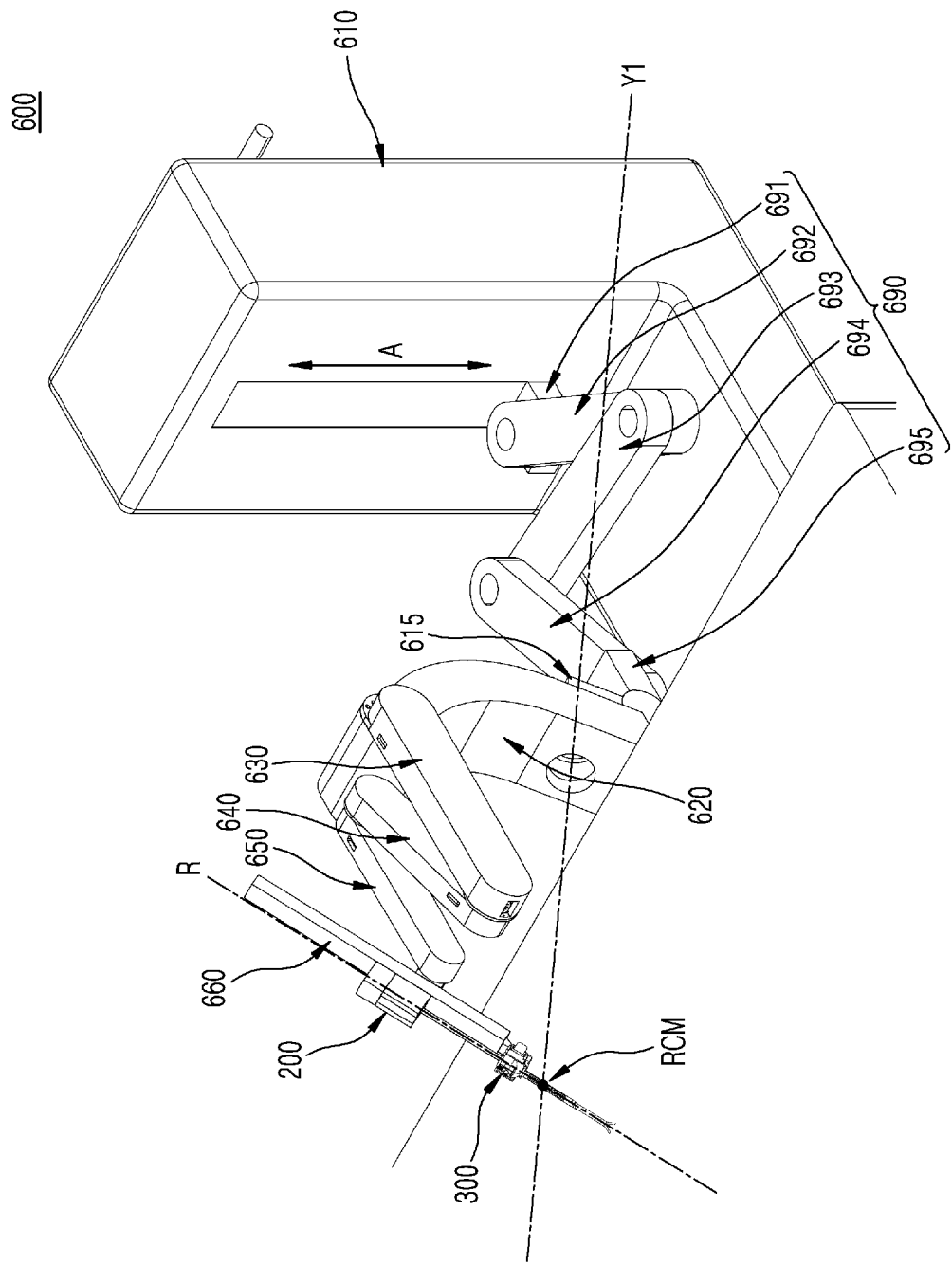
FIG. 26 is a perspective view illustrating operations of a setup link assembly of the surgical robot arm of FIG. 24.

FIG. 24 is a perspective view illustrating the surgical robot arm according to the third embodiment of the present disclosure, FIG. 25 is a perspective view illustrating operations of a pitch positioning joint of the surgical robot arm of FIG. 24, and FIG. 26 is a perspective view illustrating operations of a setup link assembly of the surgical robot arm of FIG. 24.

Referring to FIGS. 24 to 26, the surgical robot arm 600 according to the third embodiment of the present disclosure includes a body 610, a base link 615, a yaw drive assembly 605, a third link 640, a fourth link 650, and a fifth link 660. Here, the yaw drive assembly 605 may include a first link 620 and a second link 630. In addition, the surgical robot arm 600 according to the third embodiment of the present disclosure further includes the setup link assembly 690. In addition, as in the first embodiment illustrated with reference to FIG. 3, the surgical robot arm 600 of the present embodiment may include a first joint (sec 171 in FIG. 4), a second joint (see 172 in FIG. 4), a third joint (see 173 in FIG. 4), a fourth joint (sec 174 in FIG. 4), and a fifth joint (see 175 in FIG. 4). In addition, a trocar 300 and a surgical instrument 200 are coupled to the fifth link 660 of the surgical robot arm 600 described above.

Here, the body 610 serves as a base of the entire surgical robot arm 600.

Meanwhile, the base link 615 may be formed on one surface of the body 610, for example, an upper surface thereof. The base link 615 may be formed to be inclined by a certain degree to have a predetermined angle with respect to a horizontal plane.

Meanwhile, the yaw drive assembly 605 is rotatably coupled to the base link 615. The yaw drive assembly 605 is coupled to the base link 615 by the first joint (see 171 in FIG. 4), and formed to be yaw rotatable around the first yaw axis Y1 with respect to the base link 615.

Here, the yaw drive assembly 605 may include the first link 620 and the second link 630. The yaw drive assembly 605 is coupled to the base link 615 by the first joint (see 171 in FIG. 4), and formed to be yaw rotatable around the first yaw axis Y1 with respect to the base link 615. Here, the first link 620 is coupled to the base link 615 by the first joint (see 171 in FIG. 4), and formed to be yaw rotatable around the first yaw axis Y1 with respect to the base link 615. In addition, one end portion of the second link 630 is fixedly coupled to the first link 620, and another end portion thereof is coupled to the third link 640 to be described later.

The third link 640 is axially coupled to the second link 630 so as to be rotatable around the third joint (see 173 in FIG. 4) with respect to the second link 630. Here, the third joint (see 173 in FIG. 4) may include one or more pulleys.

The fourth link 650 is axially coupled to the third link 640 so as to be rotatable around the fourth joint (see 174 in FIG. 4) with respect to the third link 640. Here, the fourth joint (sec 174 in FIG. 4) may include one or more pulleys.

The fifth link 660 is axially coupled to the fourth link 650 so as to be rotatable around the fifth joint (see 175 in FIG. 4) with respect to the fourth link 650. Here, the fifth joint (sec 175 in FIG. 4) may include one or more pulleys.

The surgical instrument 200 is coupled to the fifth link 660.

Here, the third link 640, the fourth link 650, and the fifth link 660 form a parallelogram, and configure a kind of RCM mechanism. That is, when the third link 640 rotates around the third joint (see 173 in FIG. 4) in a state in which the position of the third joint (sec 173 in FIG. 4) is fixed, due to the RCM mechanism of a link/belt described above, the third link 640 and the fifth link 660 rotate while maintaining a parallel state, and the fourth link 650 and an extension line connecting the third joint (see 173 in FIG. 4) to an RCM also rotate while maintaining a parallel state. Accordingly, the RCM may remain constant in position regardless of the rotation angle of the third link 640.

Here, the surgical robot arm 600 according to the third embodiment of the present disclosure further includes the setup link assembly 690. That is, the setup and positioning of the surgical robot arm 600 can be more easily performed by further including the setup link assembly 690, which is formed between the body 610 and the base link 615, connects the body 610 to the base link 615, and allows the base link 615 (and the links connected thereto) to move vertically or horizontally with respect to the body 610. This will be described in more detail below.

In detail, the setup link assembly 690 may include a vertical setup link 691 and one or more horizontal setup links 692, 693, and 694.

The vertical setup link 691 is connected to the body 610, and formed to be movable in the Z-axis direction with respect to the body 610.

Here, a guide groove 611 is vertically formed in the body 610, and the vertical setup link 691 is linearly movable up and down along the guide groove 611 in the direction of an arrow A.

Meanwhile, the setup link assembly 690 may include a first horizontal setup link 692, a second horizontal setup link 693, and a third horizontal setup link 694. The first horizontal setup link 692 is axially coupled to the vertical setup link 691 so as to be rotatable with respect thereto. The second horizontal setup link 693 is axially coupled to the first horizontal setup link 692 so as to be rotatable with respect thereto. One end portion of the third horizontal setup link 693 is rotatably axially coupled to the second horizontal setup link 692. In addition, a pitch positioning joint 695, which will be described later, and the base link 615 connected thereto are formed at another end portion of the third horizontal setup link 693. Here, a rotation axis of each of the one or more horizontal setup links 692, 693, and 694 may be parallel to the Z-axis. That is, the one or more horizontal setup links 692, 693, and 694 may rotate on the XY plane.

As described above, since the setup link assembly 690 includes one or more horizontal setup links 692, 693, and 694, the base link 615 connected to the setup link assembly 690 may be disposed in various setup positions on the XY plane.

Meanwhile, the setup link assembly 690 may further include the pitch positioning joint 695. In addition, the pitch positioning joint 695 may further include a pitch positioning base 696 and a pitch positioning shaft 697. The pitch positioning base 696 is coupled to one end portion of the third horizontal setup link 694. In addition, the pitch positioning base 696 and base link 615 may be coupled by the pitch positioning shaft 697 so as to be rotatable around a second pitch axis P2. Here, the pitch positioning shaft 697 or the second pitch axis P2 may be substantially parallel to a pitch axis P or a rotation axis of the third joint (see 173 in FIG. 4).

That is, as shown in FIG. 25, as the base link 615 rotates around the pitch positioning shaft 697 with respect to the pitch positioning base 696, additional setup adjustments along the direction of the second pitch axis P2 could also be made.

Meanwhile, in the drawing, it is illustrated that the vertical setup link 691 is connected to the body 610 and the horizontal setup links 692, 693, and 694 are connected to the vertical setup link 691, but the concept of the present disclosure is not limited thereto. That is, a configuration in which the horizontal setup links are connected to the body 610 and the vertical setup link is connected to the horizontal setup links is also possible. Alternatively, a configuration in which only one of the vertical setup link and the horizontal setup link is provided is also possible. Alternatively, various configurations and arrangements of the horizontal setup links and vertical link are possible, such as a configuration in which the vertical setup link is disposed in the middle of a plurality of horizontal setup links.

Here, the setup link assembly 690 may be formed to be operative only during a setup period in which the surgical robot arm 600 is deployed at an appropriate position on one side of a patient before the surgical robot arm 600 actually begins to perform a surgery, and to remain in a fixed state without moving during a period in which the surgical robot arm 600 is completely deployed and actually performs a surgery. To this end, although not shown in the drawings, the setup link assembly 690 may further include a brake module (not shown) capable of maintaining a stationary state, and the brake module may further include a manipulation member (not shown) capable of selecting an activated/deactivated state.

By further including the setup link assembly 690 as described above, the setup and positioning of the surgical robot arm 600 can be more easily performed.

<Fourth Embodiment of Surgical Robot Arm>

Hereinafter, a surgical robot arm 700 according to a fourth embodiment of the present disclosure will be described. Here, the surgical robot arm 700 according to the fourth embodiment of the present disclosure is different from the surgical robot arm (see 100 in FIG. 3 or the like) according to the first embodiment of the present disclosure described above in that a setup link assembly 790 is further included. Such a configuration that is changed from that of the first embodiment will be described in detail below.

Figure 27:
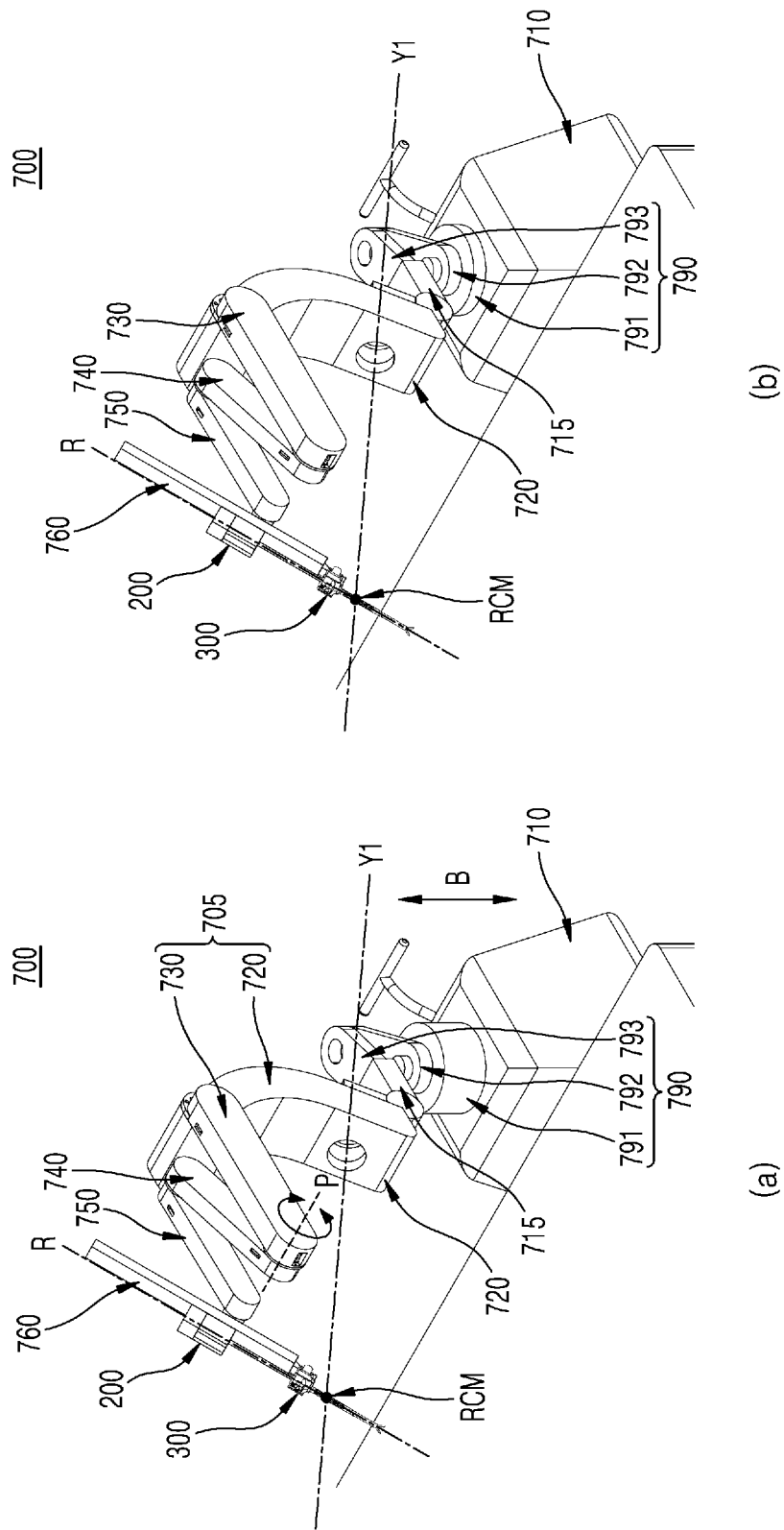
FIG. 27 is a perspective view illustrating a surgical robot arm according to a fourth embodiment of the present disclosure.
Figure 28:
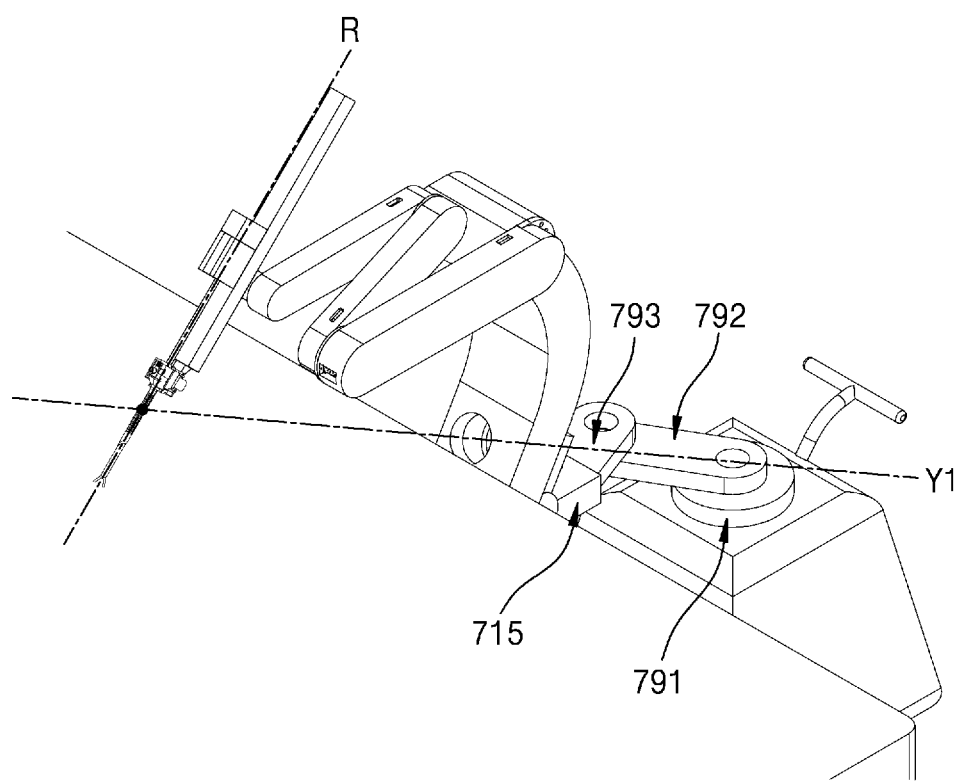
FIG. 28 is a perspective view illustrating operations of a setup link assembly of the surgical robot arm of FIG. 27.

FIG. 27 is a perspective view illustrating the surgical robot arm according to the fourth embodiment of the present disclosure, and FIG. 28 is a perspective view illustrating operations of the setup link assembly of the surgical robot arm of FIG. 27.

Referring to FIGS. 27 and 28, the surgical robot arm 700 according to the fourth embodiment of the present disclosure includes a body 710, a base link 715, a yaw drive assembly 705, a third link 740, a fourth link 750, and a fifth link 760. Here, the yaw drive assembly 705 may include a first link 720 and a second link 730. In addition, the surgical robot arm 700 according to the fourth embodiment of the present disclosure further includes the setup link assembly 790. In addition, as in the first embodiment illustrated with reference to FIG. 3, the surgical robot arm 700 of the present embodiment may include a first joint (sec 171 in FIG. 4), a second joint (see 172 in FIG. 4), a third joint (see 173 in FIG. 4), a fourth joint (sec 174 in FIG. 4), and a fifth joint (sec 175 in FIG. 4). In addition, a trocar 300 and a surgical instrument 200 are coupled to the fifth link 760 of the surgical robot arm 700 described above.

Here, the body 710 serves as a base of the entire surgical robot arm 700.

Meanwhile, the base link 715 may be formed on one surface of the body 710, for example, an upper surface thereof. The base link 715 may be formed to be inclined by a certain degree to have a predetermined angle with respect to a horizontal plane.

Meanwhile, the yaw drive assembly 705 is rotatably coupled to the base link 715. The yaw drive assembly 705 is coupled to the base link 715 by the first joint (see 171 in FIG. 4), and formed to be yaw rotatable around a first yaw axis Y1 with respect to the base link 715.

Here, the yaw drive assembly 705 may include the first link 720 and the second link 730. The yaw drive assembly 705 is coupled to the base link 715 by the first joint (see 171 in FIG. 4), and formed to be yaw rotatable around a first yaw axis Y1 with respect to the base link 715. Here, the first link 720 is coupled to the base link 715 by the first joint (see 171 in FIG. 4), and formed to be yaw rotatable around the first yaw axis Y1 with respect to the base link 715. In addition, one end portion of the second link 730 is fixedly coupled to the first link 720, and another end portion thereof is coupled to the third link 740 to be described later.

The third link 740 is axially coupled to the second link 730 so as to be rotatable around the third joint (see 173 in FIG. 4) with respect to the second link 730. Here, the third joint (see 173 in FIG. 4) may include one or more pulleys.

The fourth link 750 is axially coupled to the third link 740 so as to be rotatable around the fourth joint (see 174 in FIG. 4) with respect to the third link 740. Here, the fourth joint (see 174 in FIG. 4) may include one or more pulleys.

The fifth link 760 is axially coupled to the fourth link 750 so as to be rotatable around the fifth joint (see 175 in FIG.

4) with respect to the fourth link 750. Here, the fifth joint (see 175 in FIG. 4) may include one or more pulleys.

The surgical instrument 200 is coupled to the fifth link 760.

In this case, the third link 740, the fourth link 750, and the fifth link 760 form a parallelogram, and configure a kind of RCM mechanism. That is, when the third link 740 rotates around the third joint (see 173 in FIG. 4) in a state in which the position of the third joint (see 173 in FIG. 4) is fixed, due to the RCM mechanism of a link/belt described above, the third link 740 and the fifth link 760 rotate while maintaining a parallel state, and the fourth link 750 and an extension line connecting the third joint (see 173 in FIG. 4) to an RCM also rotate while maintaining a parallel state. Accordingly, the RCM may remain constant in position regardless of the rotation angle of the third link 740.

Here, the surgical robot arm 700 according to the fourth embodiment of the present disclosure further includes the setup link assembly 790. That is, the setup and positioning of the surgical robot arm 700 can be more easily performed by further including the setup link assembly 790, which is formed between the body 710 and the base link 715, connects the body 710 to the base link 715, and allows the base link 715 (and the links connected thereto) to move vertically or horizontally with respect to the body 710. This will be described in more detail below.

In detail, the setup link assembly 790 may include a vertical setup link 791 and one or more horizontal setup links 792 and 793.

The vertical setup link 791 is connected to the body 710, and formed to be movable in the Z-axis direction with respect to the body 710.

Here, the vertical setup link 791 is formed in a cylindrical shape, and thus, linearly movable up and down while being drawn in or out from the body 710 in the direction of an arrow B.

Meanwhile, the setup link assembly 790 may include a first horizontal setup link 792 and a second horizontal setup link 793. The first horizontal setup link 792 is axially coupled to the vertical setup link 791 so as to be rotatable with respect thereto. The second horizontal setup link 793 is axially coupled to the first horizontal setup link 792 so as to be rotatable with respect thereto. In addition, the base link 715 is formed at another end portion of the second horizontal setup link 792.

As described above, since the setup link assembly 790 includes one or more horizontal setup links 792 and 793, the base link 715 connected to the setup link assembly 790 may be disposed in various setup positions on the XY plane.

Meanwhile, in the drawing, it is illustrated that the vertical setup link 791 is connected to the body 710 and the horizontal setup links 792 and 793 are connected to the vertical setup link 791, but the concept of the present disclosure is not limited thereto. That is, a configuration in which the horizontal setup links are connected to the body 710 and the vertical setup link is connected to the horizontal setup links is also possible. Alternatively, a configuration in which only one of the vertical setup link and the horizontal setup link is provided is also possible. Alternatively, various configurations and arrangements of the horizontal setup links and vertical setup link are possible, such as a configuration in which the vertical setup link is disposed in the middle of a plurality of horizontal setup links.

Here, the setup link assembly 790 may be formed to be operative only during a period in which the surgical robot arm 700 is deployed at an appropriate position on one side of a patient before the surgical robot arm 700 actually begins to perform a surgery, and to remain in a fixed state without moving during a period in which the surgical robot arm 700 is completely deployed and actually performs a surgery. To this end, although not shown in the drawings, the setup link assembly 790 may further include a brake module (not shown) capable of maintaining a stationary state, and the brake module may further include a manipulation member (not shown) capable of selecting an activated/deactivated state.

By further including the setup link assembly 790 as described above, the setup and positioning of the surgical robot arm 700 can be more easily performed.

<Fifth Embodiment of Surgical Robot Arm>

Hereinafter, a surgical robot arm 800 according to a fifth embodiment of the present disclosure will be described. Here, the surgical robot arm 800 according to the fifth embodiment of the present disclosure is different from the surgical robot arm (see 100 in FIG. 3 or the like) according to the first embodiment of the present disclosure described above in that the number of yaw axes is changed and the configuration of a yaw drive assembly 805 is changed accordingly. In addition, the surgical robot arm 800 according to the fifth embodiment of the present disclosure is different from the surgical robot arm (see 100 in FIG. 3 or the like) according to the first embodiment of the present disclosure described above in that a setup link assembly 890 is further included.

In other words, the surgical robot arm 800 according to the fifth embodiment of the present disclosure may be viewed as a component that combines the features of the second embodiment illustrated in FIG. 18 or the like and the features of the third embodiment illustrated in FIG. 24 or the like. Such a configuration that is changed from that of the first embodiment will be described in detail below.

Figure 29:
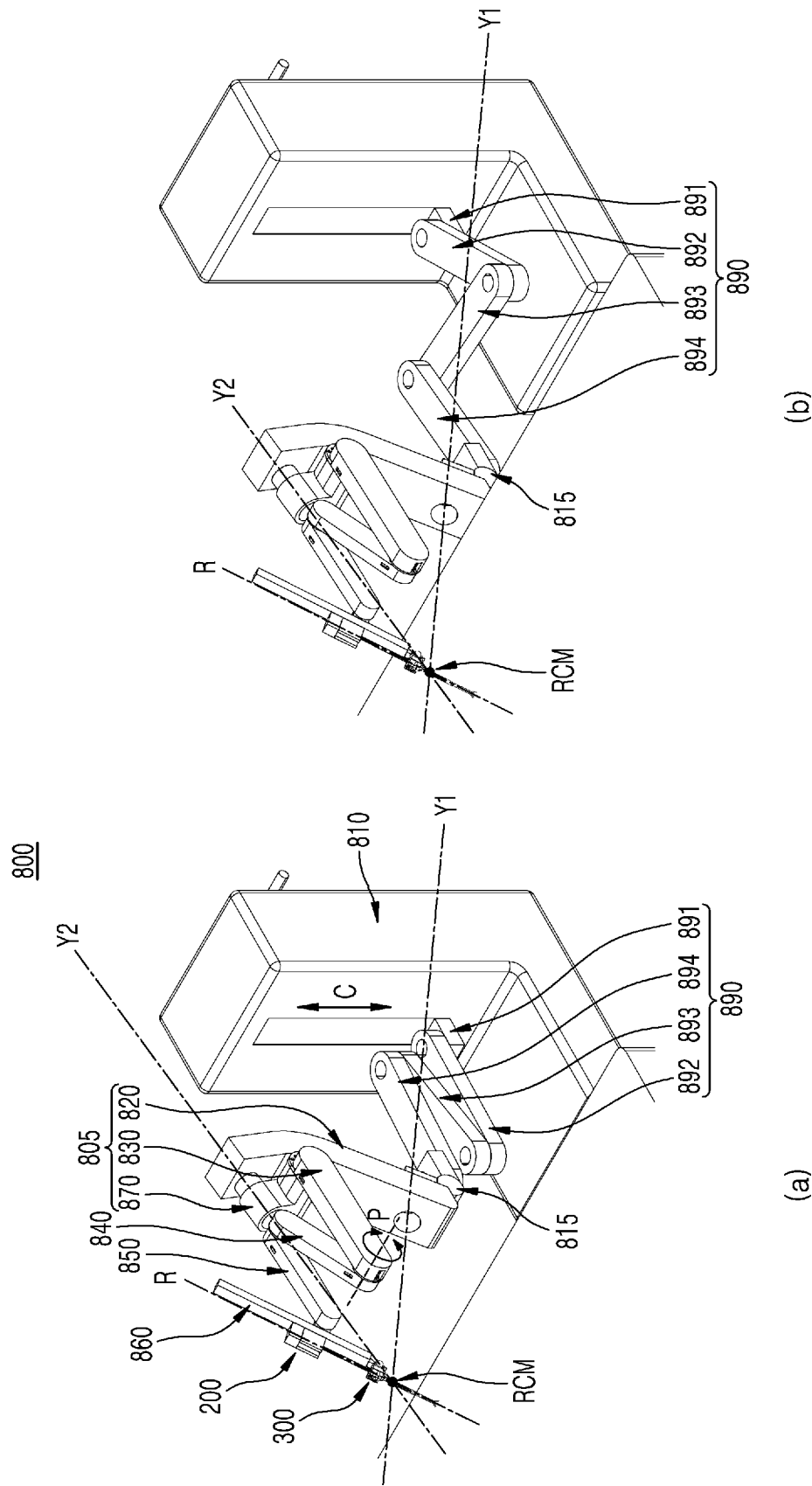
FIG. 29 is a perspective view illustrating a surgical robot arm according to a fifth embodiment of the present disclosure.

FIG. 29 is a perspective view illustrating the surgical robot arm according to the fifth embodiment of the present disclosure.

Referring to FIG. 29, the surgical robot arm 800 according to the fifth embodiment of the present disclosure includes a body 810, a base link 815, the yaw drive assembly 805, a third link 840, a fourth link 850, and a fifth link 860. Here, the yaw drive assembly 805 may include a first link 820, a second link 830, and a sixth link 870. In addition, the surgical robot arm 800 according to the sixth embodiment of the present disclosure further includes the setup link assembly 890. In addition, as in the first embodiment illustrated with reference to FIG. 3, the surgical robot arm 800 of the present embodiment may include a first joint (see 171 in FIG. 4), a second joint (see 172 in FIG. 4), a third joint (see 173 in FIG. 4), a fourth joint (see 174 in FIG. 4), and a fifth joint (see 175 in FIG. 4). In addition, the surgical robot arm 800 of the present embodiment may further include a sixth joint 876. In addition, a trocar 300 and a surgical instrument 200 are coupled to the fifth link 860 of the surgical robot arm 800 described above.

Here, the surgical robot arm 800 according to the fifth embodiment of the present disclosure includes two yaw axes, i.e., a first yaw axis Y1 and a second yaw axis Y2. That is, by having the first yaw axis Y1 and the second yaw axis Y2 that are rotatable independently of each other, a yaw motion may be performed around the second yaw axis Y2 when a roll axis R and the first yaw axis Y1 coincide with each other, and a yaw motion may be performed around the first yaw axis Y1 when the roll axis R and the second yaw axis Y2 coincide with each other.

Here, the yaw drive assembly 805 of the surgical robot arm 800 may include the first link 820 and the second link

830. In addition, the yaw drive assembly 805 of the surgical robot arm 800 according to the second embodiment of the present disclosure may further include the sixth link 870 connecting the first link 820 to the second link 830. Since each component of the yaw drive assembly 805 is substantially the same as the second embodiment described above, detailed descriptions thereof will be omitted herein.

By having two yaw axes as described above, when one of the yaw axes coincides with the roll axis and thus there is a possibility that a gimbal lock phenomenon occurs, the yaw motion may be performed using the other yaw axis. Thus, even when each link of the surgical robot arm 800 is in any motion state, it is possible to obtain an effect of performing a desired motion without inducing a gimbal lock phenomenon.

Meanwhile, the surgical robot arm 800 according to the fifth embodiment of the present disclosure further includes the setup link assembly 890. That is, the setup and positioning of the surgical robot arm 800 can be more easily performed by further including the setup link assembly 890, which is formed between the body 810 and the base link 815, connects the body 810 to the base link 815, and allows the base link 815 (and the links connected thereto) to move vertically or horizontally with respect to the body 810.

Here, the setup link assembly 890 may include a vertical setup link 891 and one or more horizontal setup links 892, 893, and 894. Since each component of the setup link assembly 890 is substantially the same as the above-described third embodiment, detailed descriptions thereof will be omitted herein.

By further including the setup link assembly 890 as described above, the setup and positioning of the surgical robot arm 800 can be more easily performed.

<Sixth Embodiment of Surgical Robot Arm>

Hereinafter, a surgical robot arm 900 according to a sixth embodiment of the present disclosure will be described. Here, the surgical robot arm 900 according to the sixth embodiment of the present disclosure is different from the surgical robot arm (see 100 in FIG. 3 or the like) according to the first embodiment of the present disclosure described above in that the number of yaw axes is changed and the configuration of a yaw drive assembly 905 is changed accordingly. In addition, the surgical robot arm 900 according to the sixth embodiment of the present disclosure is different from the surgical robot arm (see 100 in FIG. 3 or the like) according to the first embodiment of the present disclosure described above in that a setup link assembly 990 is further included.

In other words, the surgical robot arm 900 according to the sixth embodiment of the present disclosure may be viewed as a component that combines the features of the second embodiment illustrated in FIG. 18 or the like and the features of the fourth embodiment illustrated in FIG. 27 or the like. Such a configuration that is changed from that of the first embodiment will be described in detail below.

Figure 30:
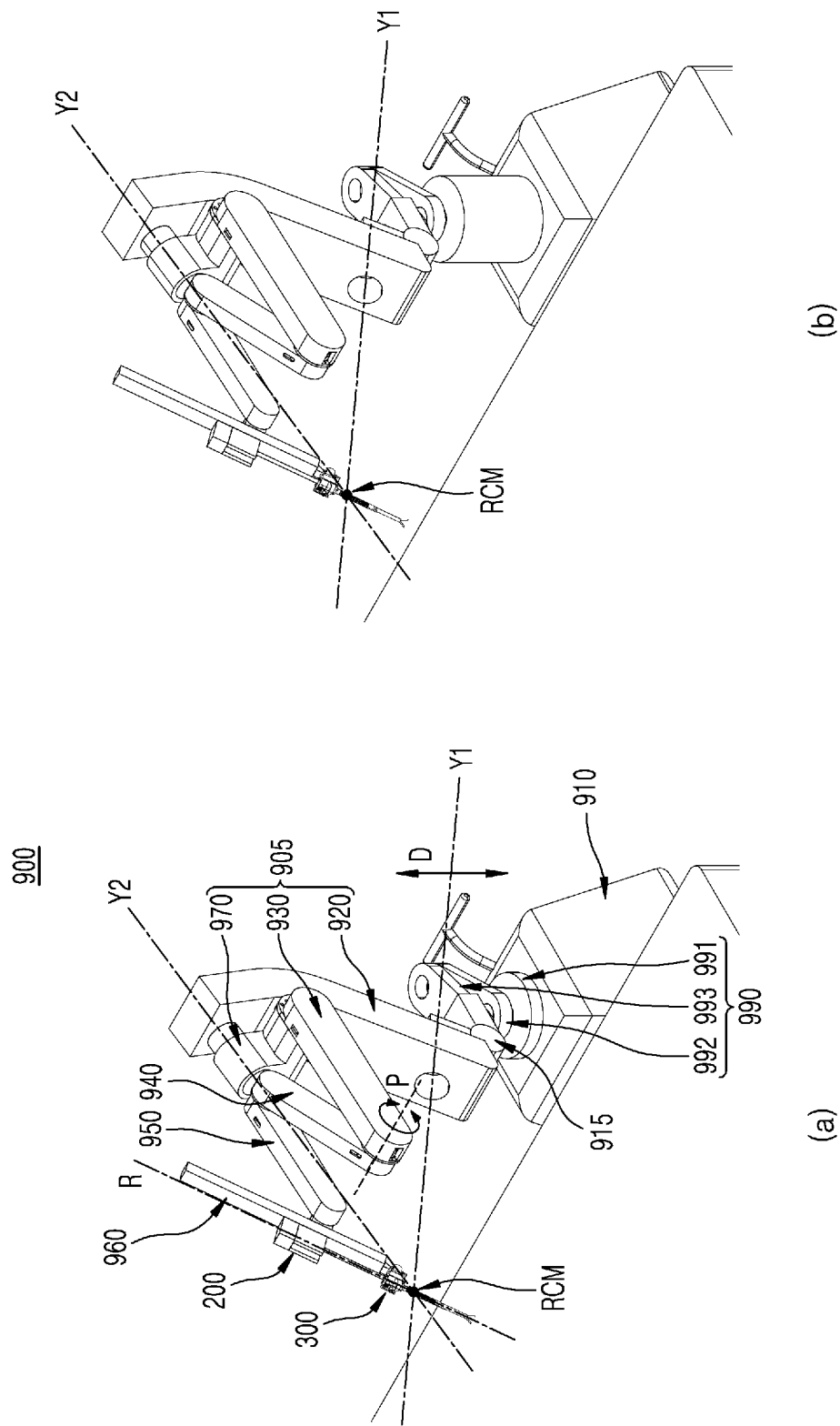
FIG. 30 is a perspective view illustrating a surgical robot arm according to a sixth embodiment of the present disclosure.
Figure 31:
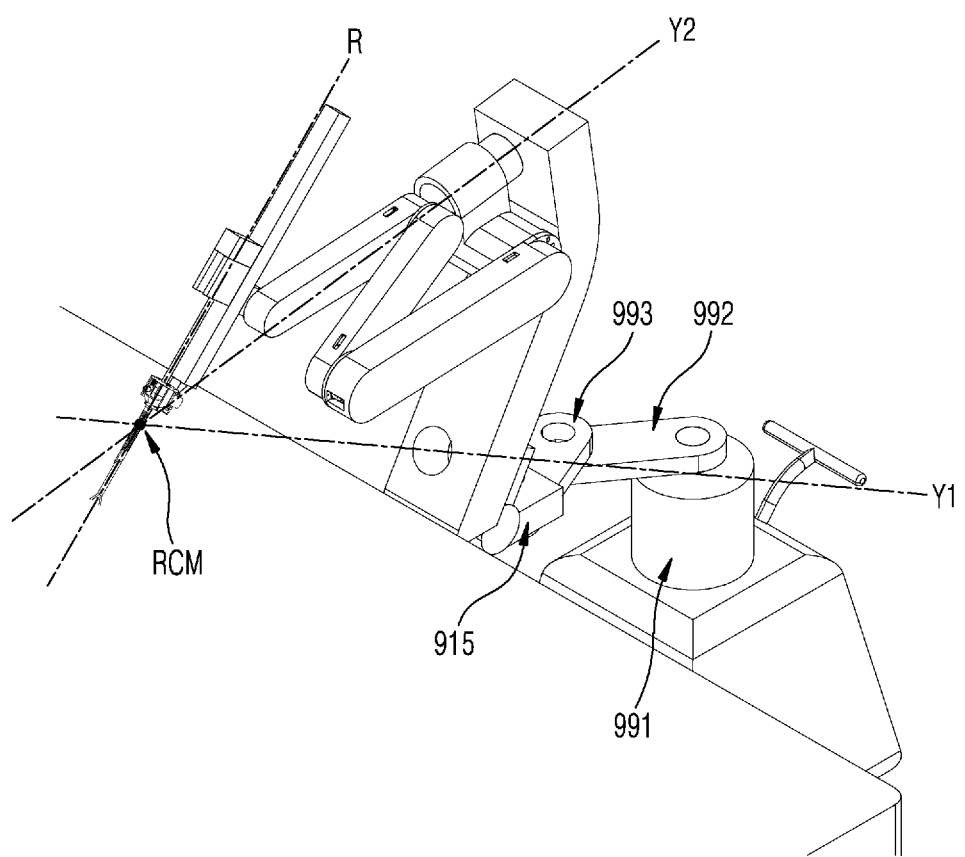
FIG. 31 is a perspective view illustrating operations of a setup link assembly of the surgical robot arm of FIG. 30.

FIG. 30 is a perspective view illustrating the surgical robot arm according to the sixth embodiment of the present disclosure, and FIG. 31 is a perspective view illustrating operations of the setup link assembly of the surgical robot arm of FIG. 30.

Referring to FIGS. 31 and 31, the surgical robot arm 900 according to the sixth embodiment of the present disclosure includes a body 910, a base link 915, a yaw drive assembly 905, a third link 940, a fourth link 950, and a fifth link 960. Here, the yaw drive assembly 905 may include a first link 920, a second link 930, and a sixth link 970. In addition, the surgical robot arm 900 according to the sixth embodiment of the present disclosure further includes the setup link assembly 990. In addition, as in the first embodiment illustrated with reference to FIG. 3, the surgical robot arm 900 of the present embodiment may include a first joint (see 171 in FIG. 4), a second joint (see 172 in FIG. 4), a third joint (see 173 in FIG. 4), a fourth joint (sec 174 in FIG. 4), and a fifth joint (see 175 in FIG. 4). In addition, the surgical robot arm 900 of the present embodiment may further include a sixth joint 976. In addition, a trocar 300 and a surgical instrument 200 are coupled to the fifth link 960 of the surgical robot arm 900 described above.

Here, the surgical robot arm 900 according to the sixth embodiment of the present disclosure includes two yaw axes, i.e., a first yaw axis Y1 and a second yaw axis Y2. That is, by having the first yaw axis Y1 and the second yaw axis Y2 that are rotatable independently of each other, a yaw motion may be performed around the second yaw axis Y2 when a roll axis R and the first yaw axis Y1 coincide with each other, and a yaw motion may be performed around the first yaw axis Y1 when the roll axis R and the second yaw axis Y2 coincide with each other.

Here, the yaw drive assembly 905 of the surgical robot arm 900 may include the first link 920 and the second link 930. In addition, the yaw drive assembly 905 of the surgical robot arm 900 according to the second embodiment of the present disclosure may further include the sixth link 970 connecting the first link 920 to the second link 930. Since each component of the yaw drive assembly 905 is substantially the same as the second embodiment described above, detailed descriptions thereof will be omitted herein.

By having two yaw axes as described above, when one of the yaw axes coincides with the roll axis and thus there is a possibility that a gimbal lock phenomenon occurs, the yaw motion may be performed using the other yaw axis. Thus, even when each link of the surgical robot arm 900 is in any motion state, it is possible to obtain an effect of performing a desired motion without inducing a gimbal lock phenomenon.

Meanwhile, the surgical robot arm 900 according to the sixth embodiment of the present disclosure further includes the setup link assembly 990. That is, the setup and positioning of the surgical robot arm 900 can be more easily performed by further including the setup link assembly 990, which is formed between the body 910 and the base link 915, connects the body 910 to the base link 915, and allows the base link 915 (and the links connected thereto) to move vertically or horizontally with respect to the body 910.

Here, the setup link assembly 990 may include a vertical setup link 991 and one or more horizontal setup links 992 and 993. Since each component of the setup link assembly 990 is substantially the same as the above-described fourth embodiment, detailed descriptions thereof will be omitted herein.

By further including the setup link assembly 990 as described above, the setup and positioning of the surgical robot arm 900 can be more easily performed.

<Seventh Embodiment of Surgical Robot Arm>

Hereinafter, a surgical robot arm 1100 according to a seventh embodiment of the present disclosure will be described. Here, the surgical robot arm 1100 according to the seventh embodiment of the present disclosure is different from the surgical robot arm (see 100 in FIG. 3 or the like) according to the first embodiment of the present disclosure described above in that the configuration and arrangement surface of links are changed. Such a configuration that is changed from that of the first embodiment will be described in detail below.

Figure 32:
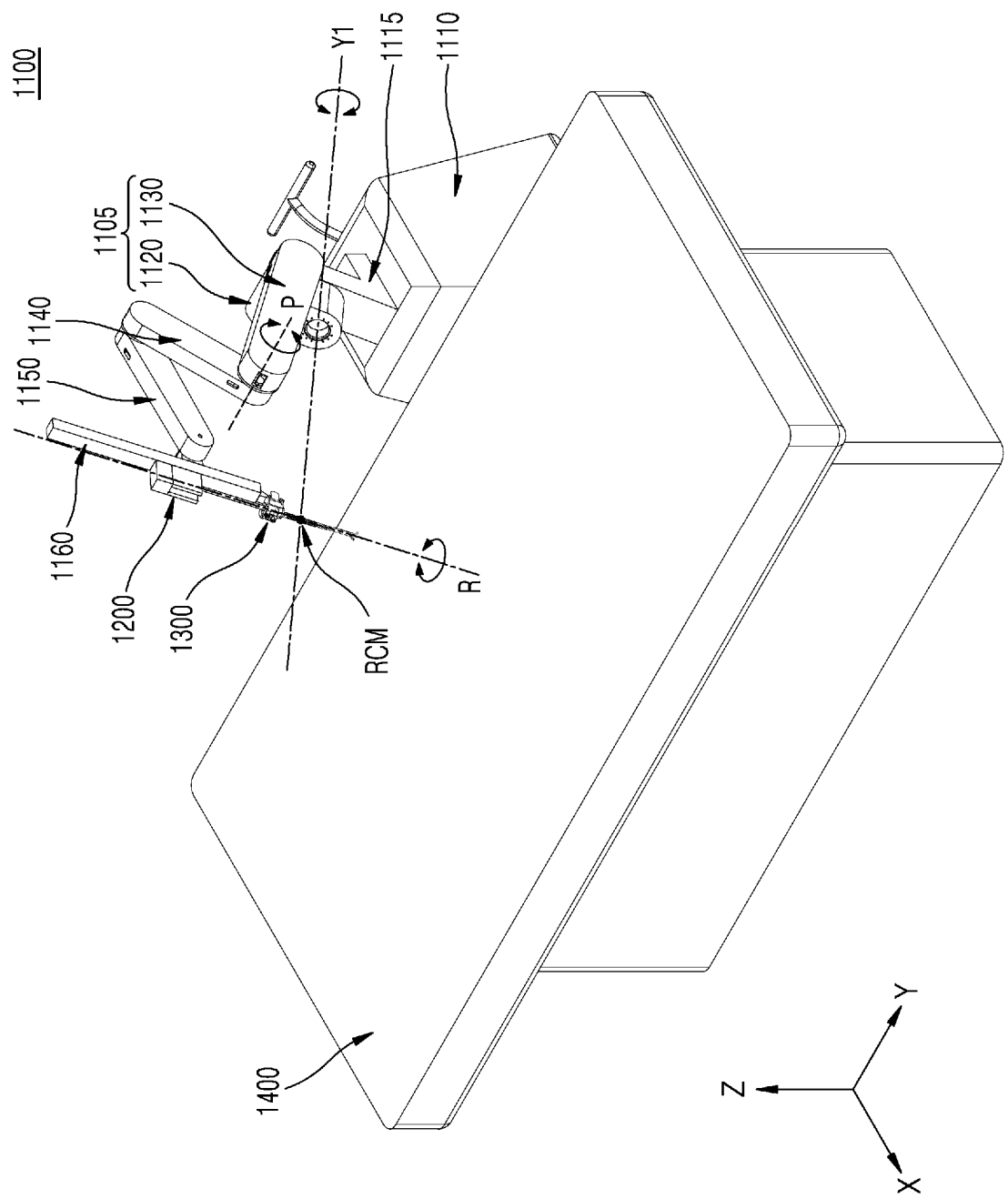
FIG. 32 is a perspective view illustrating a surgical robot arm according to a seventh embodiment of the present disclosure.
Figure 33:
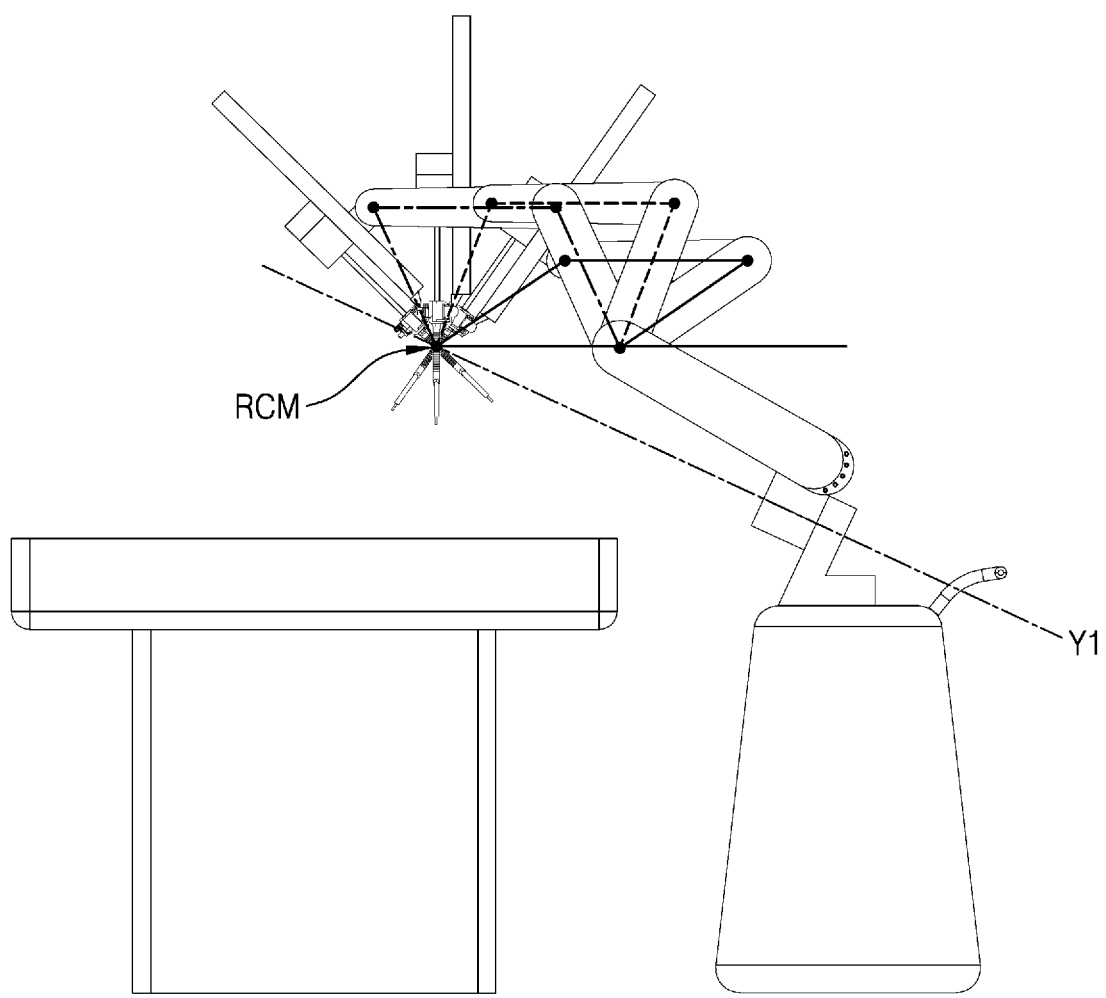
FIG. 33 is a side view of the surgical robot arm of FIG. 32.
Figure 34:
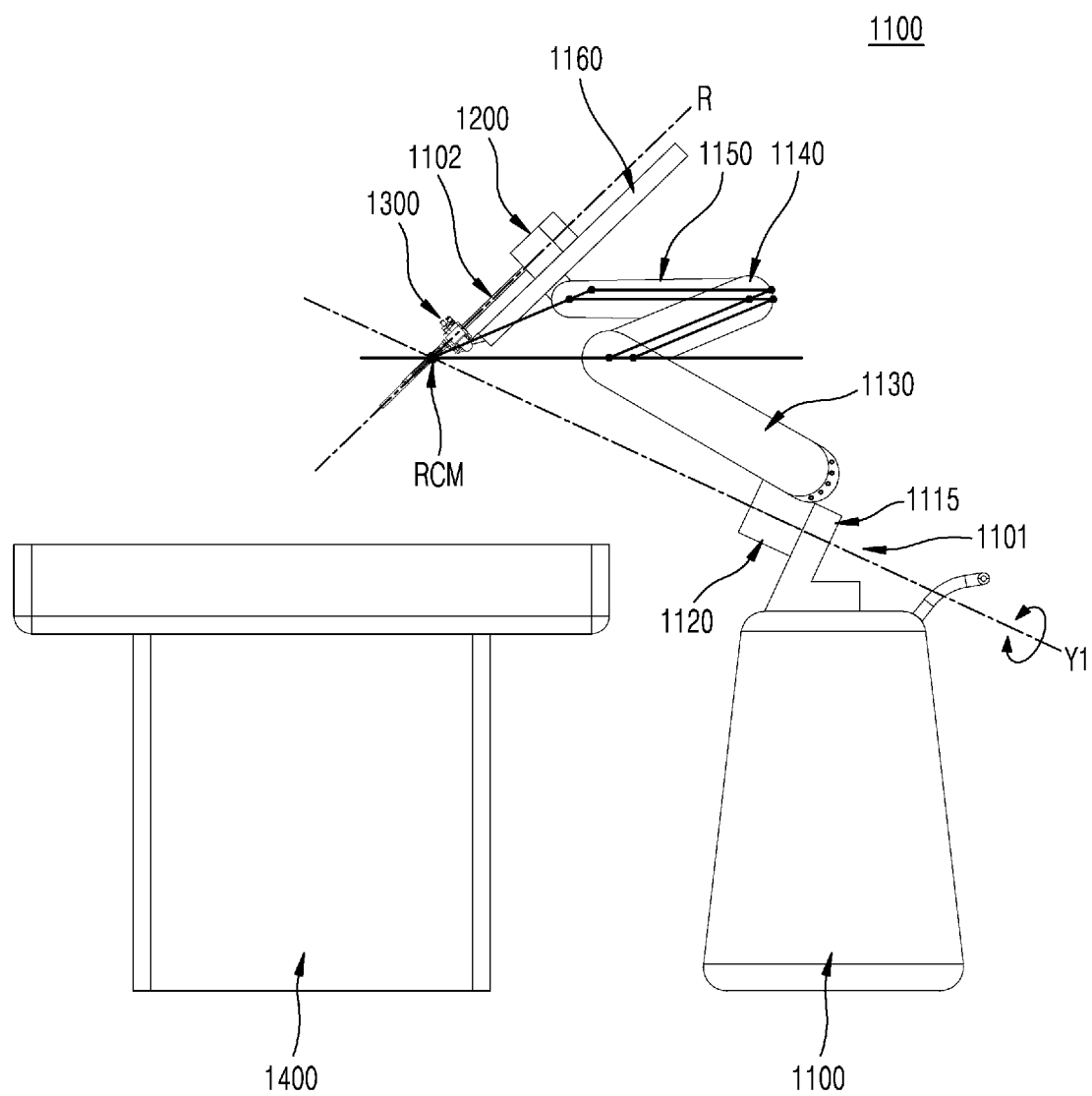
FIG. 34 is a view illustrating an example in which an RCM mechanism of a link structure is applied to the surgical robot arm of FIG. 32.
Figure 35:
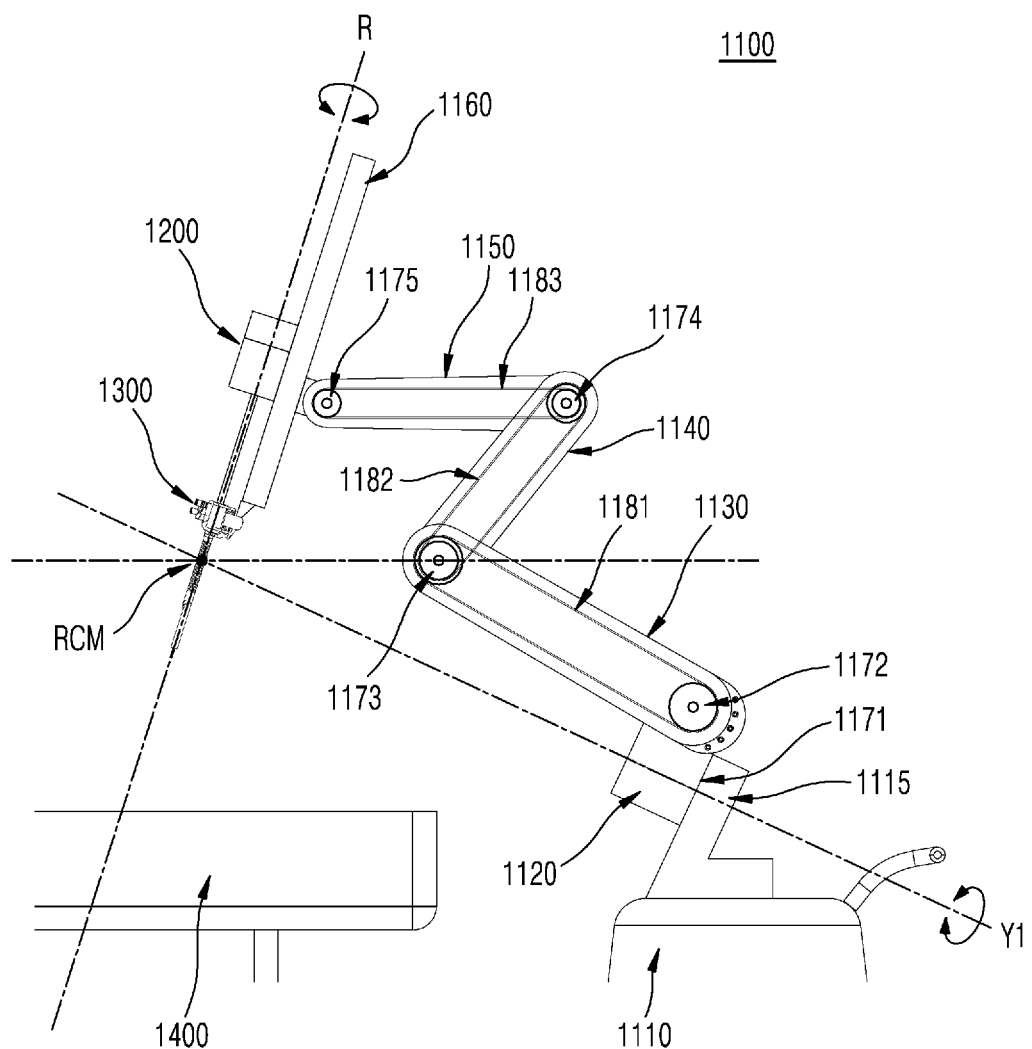
FIG. 35 is a view illustrating an example in which an RCM mechanism of a belt structure is applied to the surgical robot arm of FIG. 32.
Figure 36:
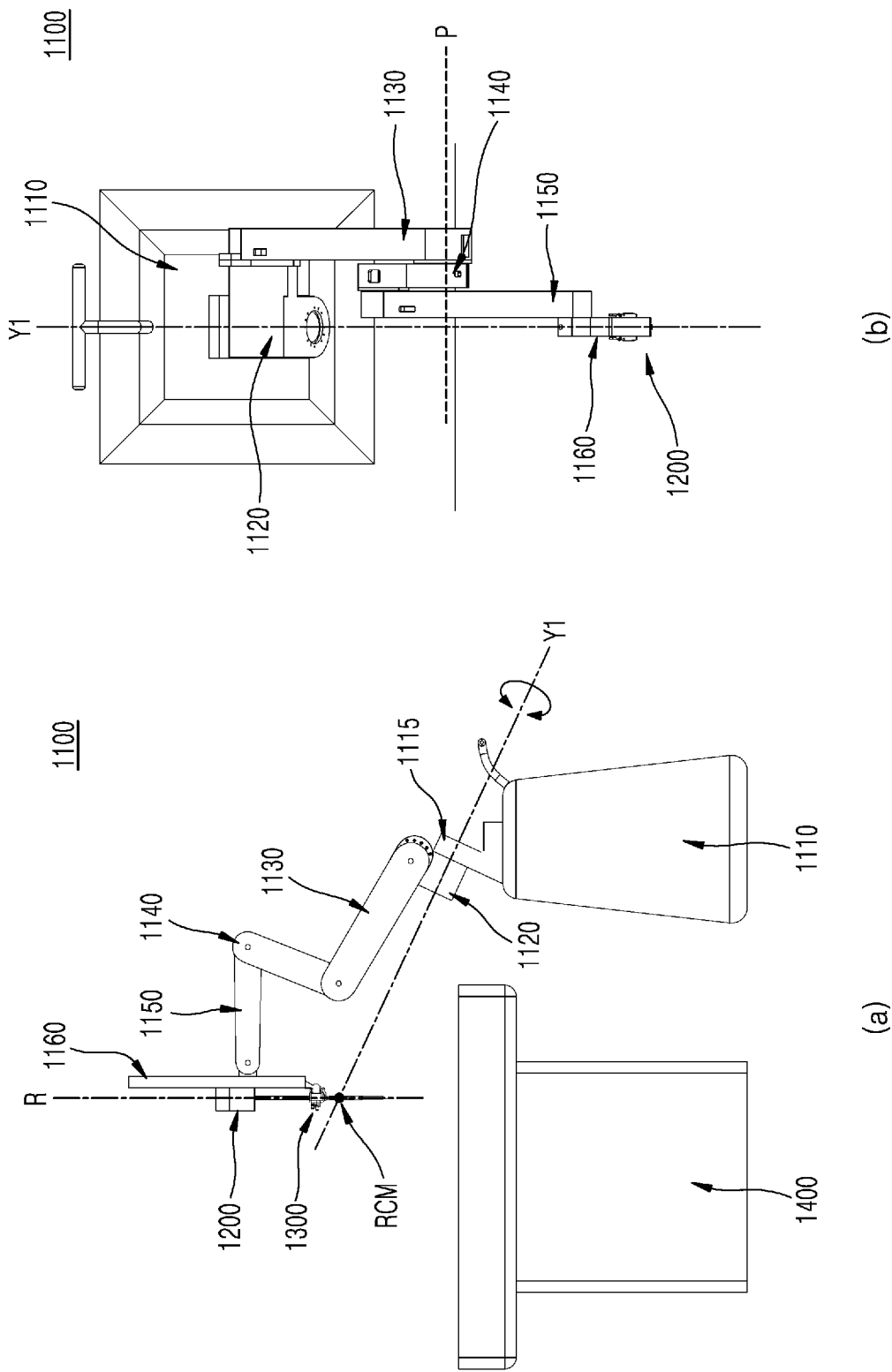
FIGS. 36 to 38 are views illustrating an RCM motion (pitch motion) of the surgical robot arm of FIG. 32 around a pitch axis P, each view including both a side view and a plan view.
Figure 37:
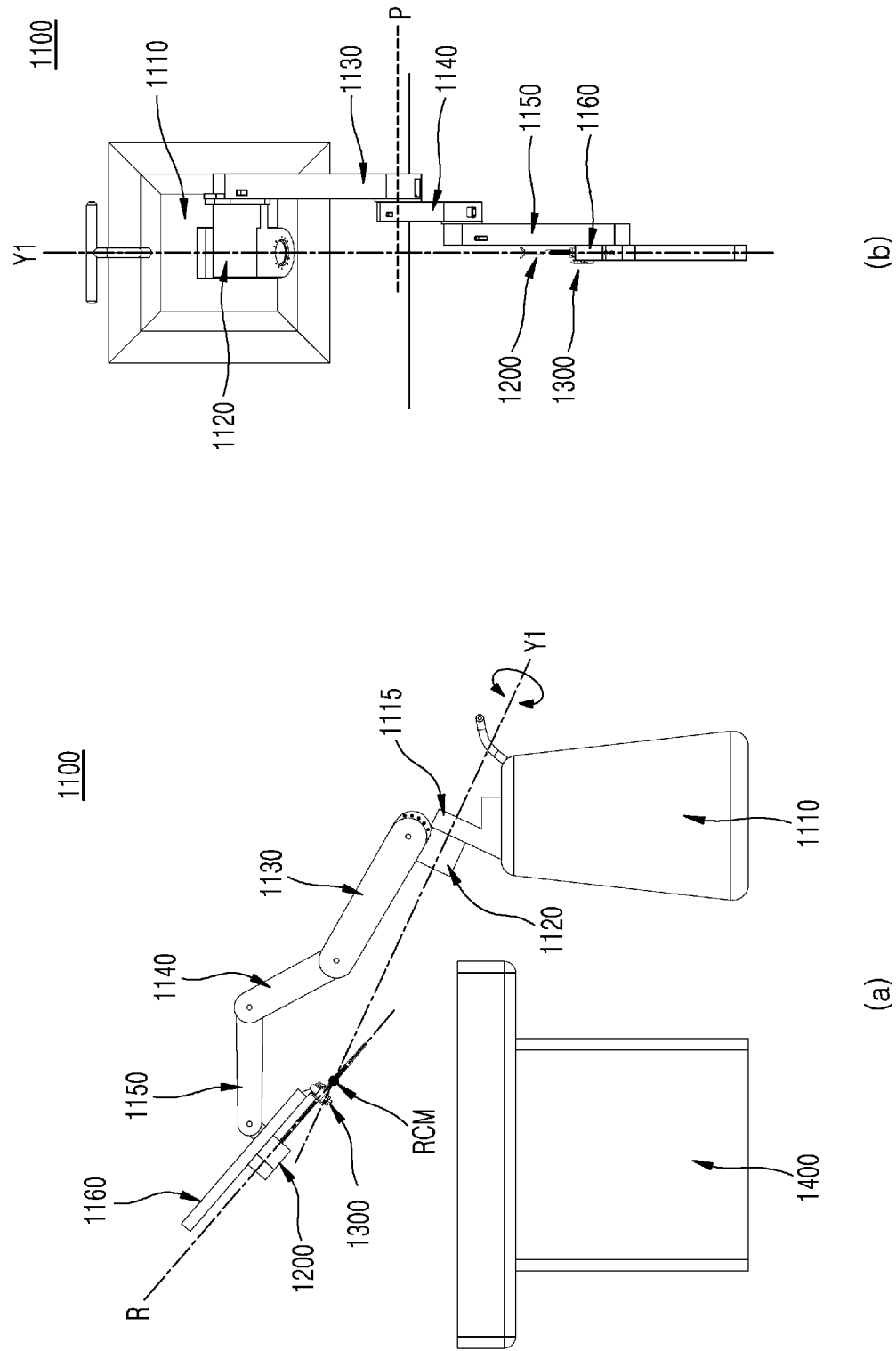
Figure 38:
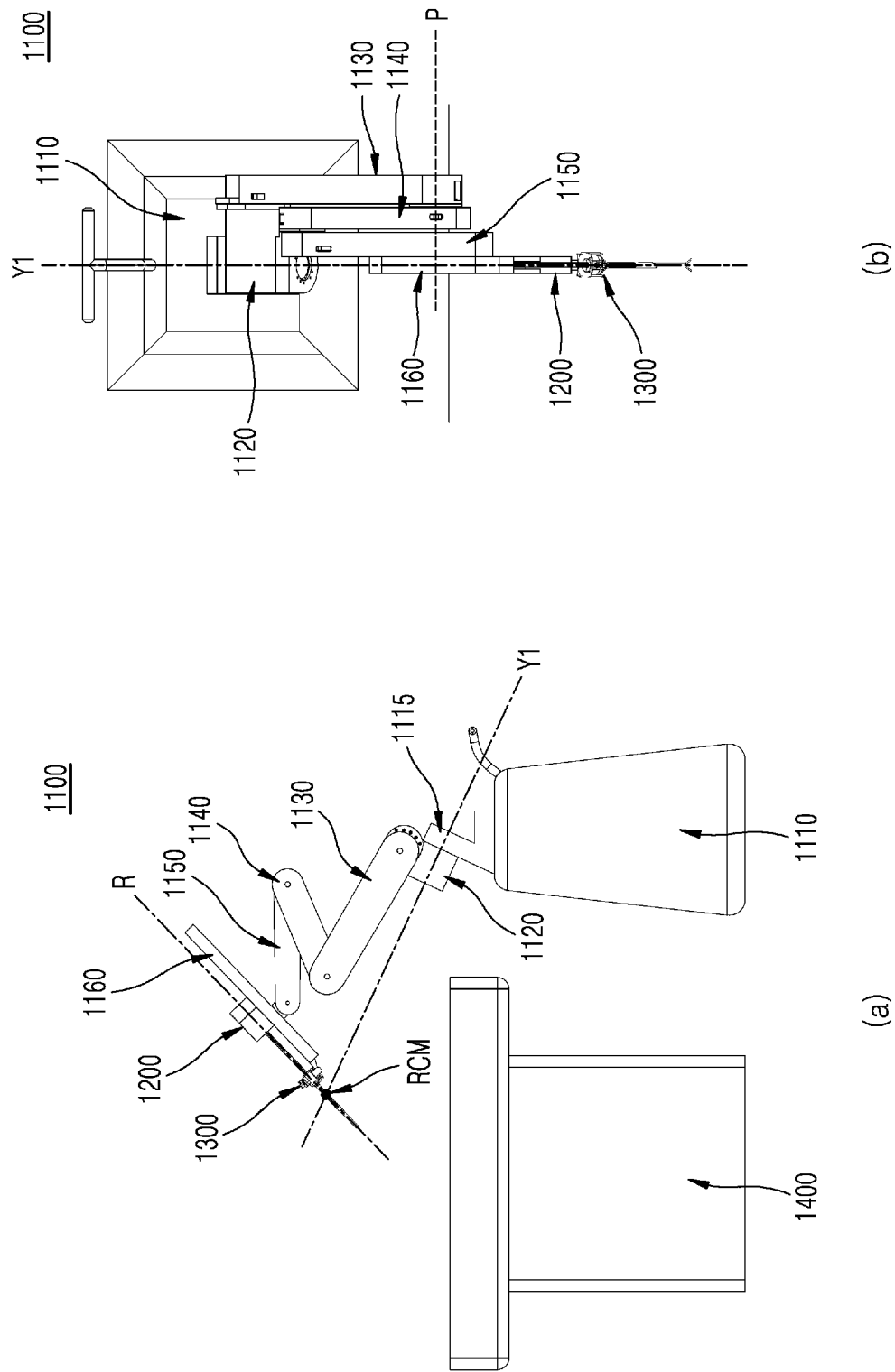
Figure 39:
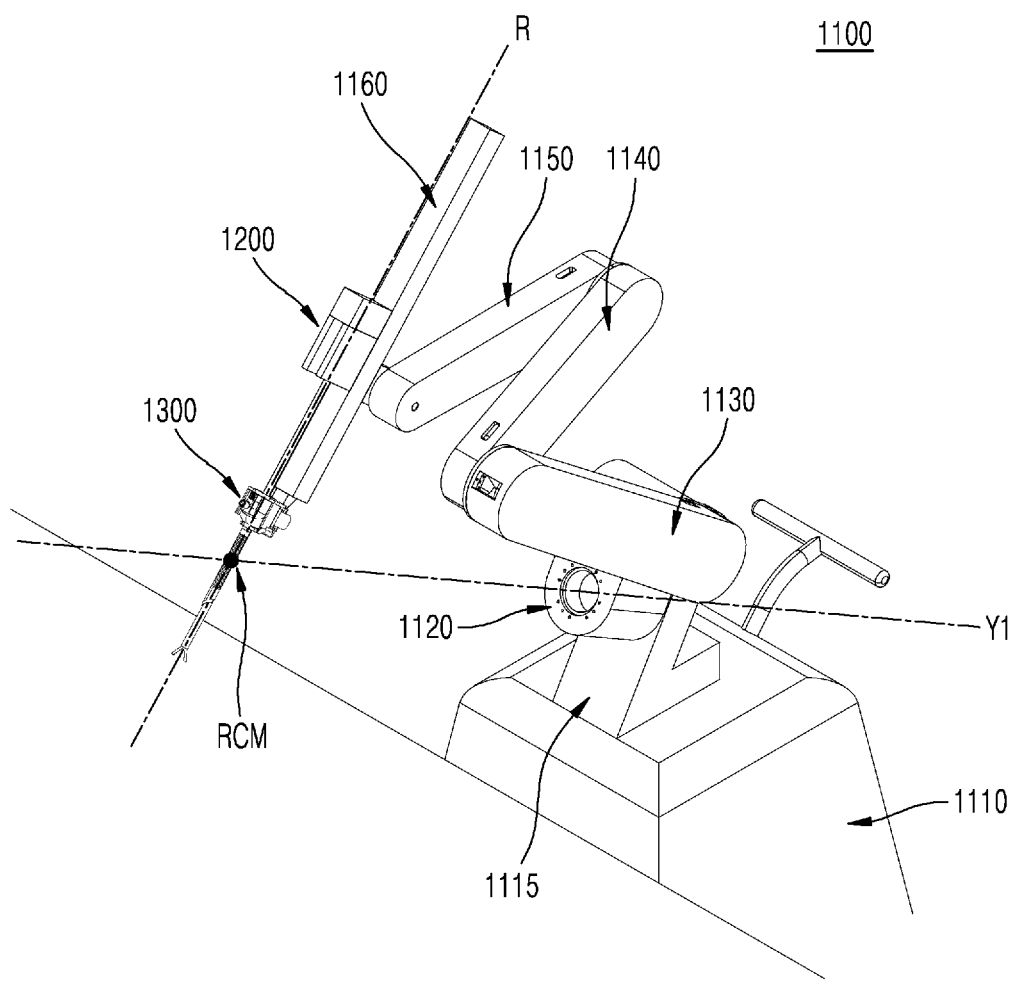
FIGS. 39 to 41 are perspective views illustrating an RCM motion (yaw motion) of the surgical robot arm of FIG. 32 around a first yaw axis Y1.
Figure 40:
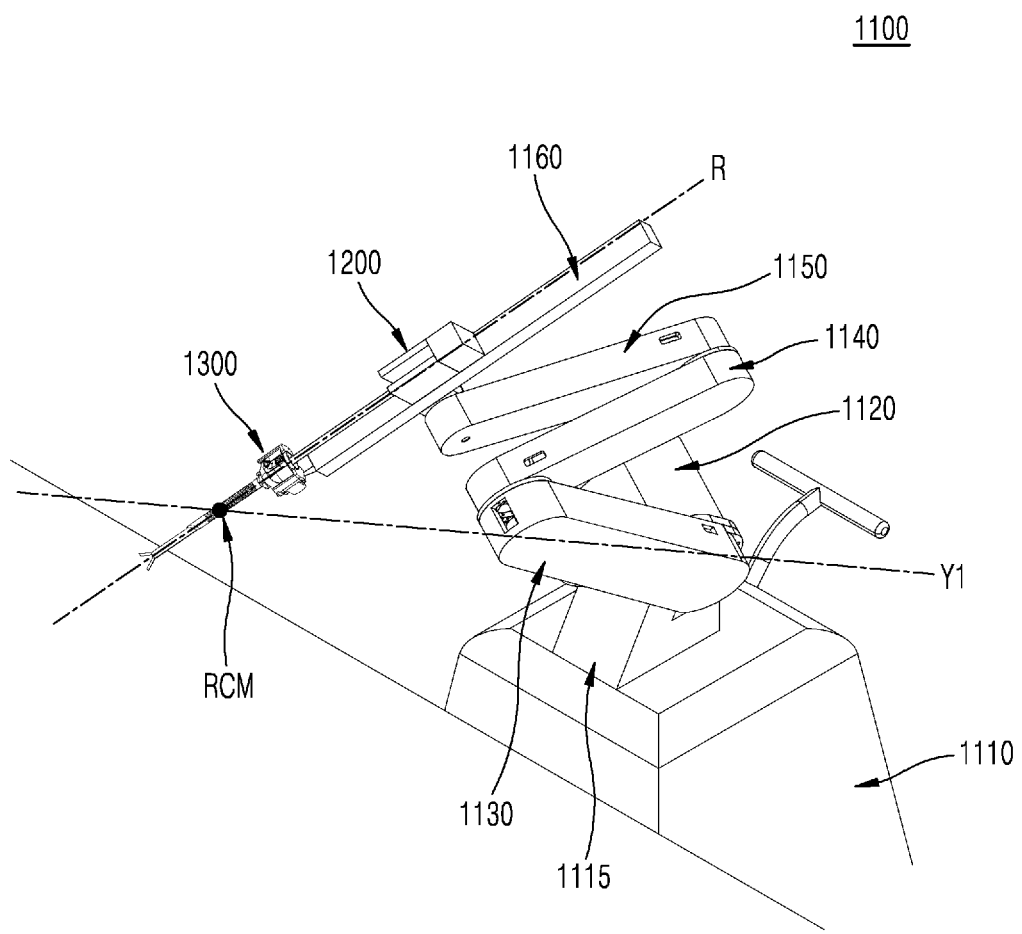
Figure 41:
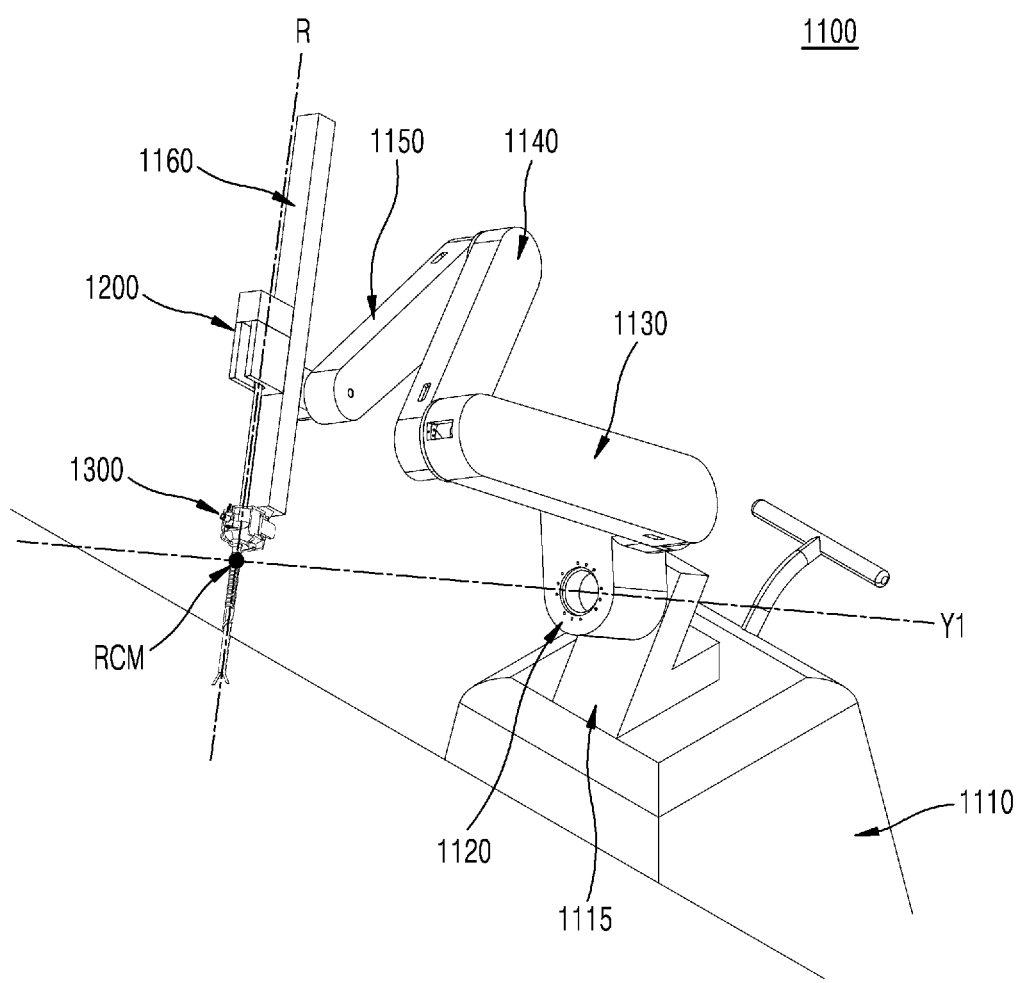
Figure 42:
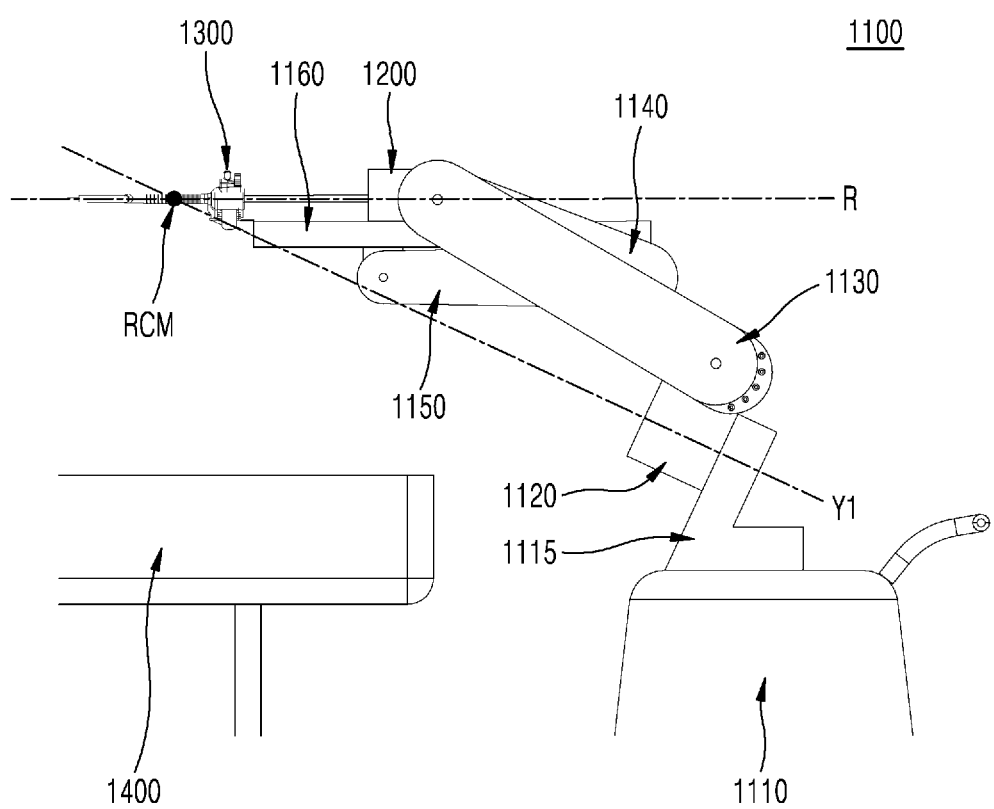
FIG. 42 is a view illustrating a state in which a fifth link of the surgical robot arm of FIG. 32 and a surgical instrument coupled thereto are disposed parallel to each other.
Figure 43:
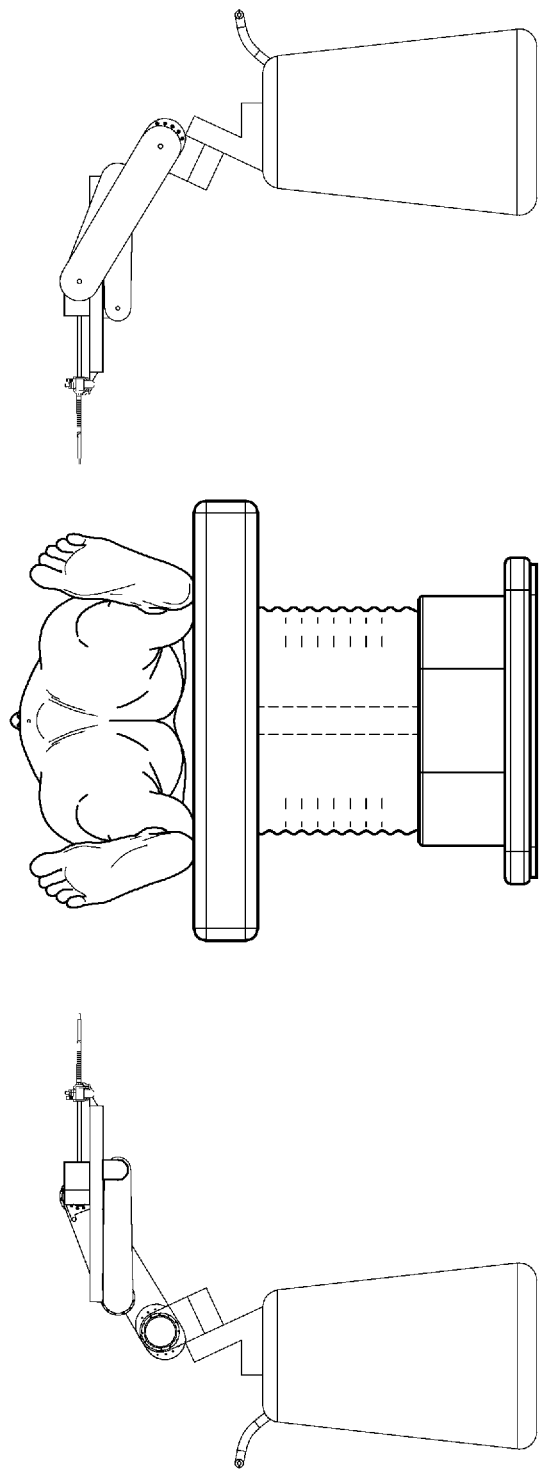
FIG. 43 is a view illustrating a state in which the surgical robot arm illustrated in FIG. 42 is disposed near a patient's surgical site and the surgical instrument is disposed directly facing a patient.
Figure 44:
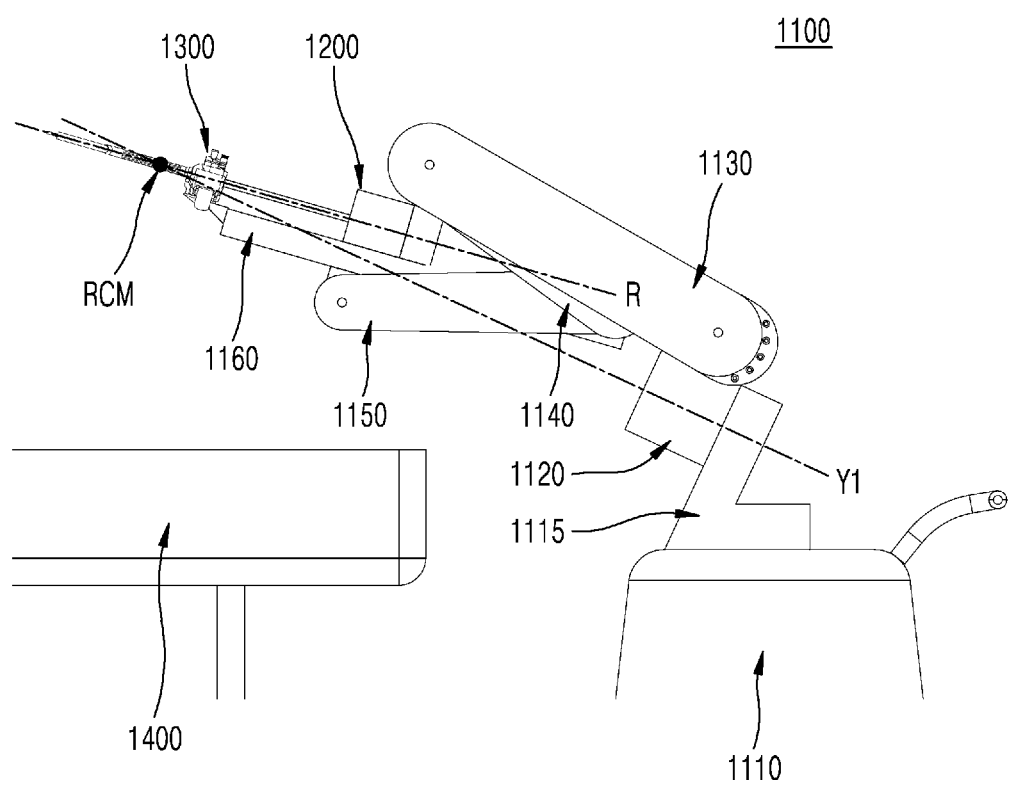
FIG. 44 is a view illustrating a state in which an end tool of the surgical instrument coupled to the fifth link of the surgical robot arm of FIG. 32 is disposed facing upward from below.

FIG. 32 is a perspective view illustrating the surgical robot arm according to the seventh embodiment of the present disclosure, and FIG. 33 is a side view of the surgical robot arm of FIG. 32. FIG. 34 is a view illustrating an example in which an RCM mechanism of a link structure is applied to the surgical robot arm of FIG. 32, and FIG. 35 is a view illustrating an example in which an RCM mechanism of a belt structure is applied to the surgical robot arm of FIG. 32. FIGS. 36 to 38 are views illustrating an RCM motion (pitch motion) of the surgical robot arm of FIG. 32 around a pitch axis P, each view including both a side view and a plan view. FIGS. 39 to 41 are perspective views illustrating an RCM motion (yaw motion) of the surgical robot arm of FIG. 32 around a first yaw axis Y1. FIG. 42 is a view illustrating a state in which a fifth link of the surgical robot arm of FIG. 32 and a surgical instrument coupled thereto are disposed parallel to each other, and FIG. 43 is a view illustrating a state in which the surgical robot arm illustrated in FIG. 42 is disposed near a patient's surgical site and the surgical instrument is disposed directly facing a patient. FIG. 44 is a view illustrating a state in which an end tool of the surgical instrument coupled to the fifth link of the surgical robot arm of FIG. 32 is disposed facing upward from below, and FIG. 45 is a set of a plan view and a side view illustrating a state in which the surgical robot arm in FIG. 32 rotates further around the first yaw axis Y1 by approximately 90°.

Referring to FIGS. 32 to 45, the surgical robot arm 1100 according to the seventh embodiment of the present disclosure includes a body 1110, a base link 1115, a yaw drive assembly 1105, a third link 1140, a fourth link 1150, and a fifth link 1160. Here, the yaw drive assembly 1105 may include a first link 1120 and a second link 1130. In addition, as in the first embodiment illustrated with reference to FIG. 3, the surgical robot arm 1100 of the present embodiment may include a first joint 1171, a second joint 1172, a third joint 1173, a fourth joint 1174, and a fifth joint 1175. In addition, a trocar 1300 and a surgical instrument 1200 are coupled to the fifth link 1160 of the surgical robot arm 1100 described above.

Here, the body 1110 serves as a base of the entire surgical robot arm 1100.

Meanwhile, a base link 1115 may be formed on one surface of the body 1110, for example, an upper surface thereof. The base link 1115 may be formed to be inclined by a certain degree to have a predetermined angle with respect to a horizontal plane.

In detail, the base link 1115 may be formed in the form of a bent flat plate or wedge, with one region coupled to an upper surface of the body 1110 and another one bent region disposed to be inclined with respect to the upper surface of the body 1110. Here, the base link 1115 may be formed to be inclined by a certain degree (e.g., 30°) with respect to the horizontal plane rather than a right angle, so that the first yaw axis Y1 passing through the base link 1115 may be formed not to be parallel to the horizontal direction (i.e., the X-axis direction). This will be described in more detail later.

Meanwhile, the yaw drive assembly 1105 is rotatably coupled to the base link 1115.

In detail, the yaw drive assembly 1105 may include the first link 1120 and the second link 1130. The yaw drive assembly 1105 is coupled to the base link 1115 by the first joint 1171, and formed to be yaw rotatable around the first yaw axis Y1 with respect to the base link 1115.

Here, the first link 1120 is coupled to the base link 1115 by the first joint 1171, and formed to be yaw rotatable around the first yaw axis Y1 with respect to the base link 1115. In addition, one end portion of the second link 1130 is fixedly coupled to the first link 1120, and another end portion thereof is coupled to the third link 1140 to be described later.

In an example, the first link 1120 may be formed in a substantially cylindrical shape, and thus may yaw-rotate around the first yaw axis Y1 with respect to the base link 1115. In addition, the second link 1130 is coupled to one side of the first link 1120 having a cylindrical shape, and thus, may yaw-rotate around the first yaw axis Y1 together with the first link 1120. Here, the second link 1130 may be formed to be approximately parallel to the first yaw axis Y1. This will be described in more detail later.

The first joint 1171 rotatably couples the base link 1115 to the first link 1120. In detail, the first joint 1171 is formed so that the first link 1120 yaw-rotates around the first yaw axis Y1 formed to pass through an RCM. Here, although not shown in the drawings, the first joint 1171 may include a motor for rotating the first link 1120.

Here, the first yaw axis Y1 may be formed in an oblique direction that is not parallel to the X-axis/Y-axis/Z-axis. Specifically, the first yaw axis Y1 and an extension line connecting the third joint 1173 to the RCM may be formed to be different from each other, and the first yaw axis Y1 and the extension line connecting the third joint 1173 to the RCM may be formed to intersect each other at the RCM. That is, the RCM to be described later may be positioned on an extension line of the first yaw axis Y1. By forming the RCM to be positioned on the extension line of the first yaw axis Y1 as described above, the position and orientation of the RCM with respect to the base link 1115 remains constant regardless of how much yaw rotation the first link 1120 has made relative to the base link 1115.

Here, as described above, as the base link 1115 is formed to be inclined by a certain degree (e.g., 30°) rather than a right angle, the first yaw axis Y1 passing through the base link 1115 may be formed not to be parallel to the horizontal direction (i.e., the X-axis direction).

In other words, it may be said that a height of the RCM in the Z-axis direction is formed to be greater than a height of a point (i.e., the first joint 1171) of the base link 1115, through which the first yaw axis Y1 passes through, in the Z-axis direction.

In other words, it may be said that a height of the first yaw axis Y1 in the Z-axis direction at a distal end 1102 of the surgical robot arm 1100 is formed to be greater than a height of the first yaw axis Y1 in the Z-axis direction at a proximal end 1101 of the surgical robot arm 1100.

In other words, it may be described that the base link 1115 is formed to be inclined at a predetermined angle with respect to the horizontal plane, so that a central axis of the base link 1115 is formed to coincide with the first yaw axis Y1.

As described above, by forming the first yaw axis Y1 and the extension line connecting the third joint 1173 to the RCM to be different from each other, and forming the first yaw axis Y1 to be inclined with respect to the horizontal plane, the fifth link 1160 and the surgical instrument 1200 coupled thereto can be disposed in the horizontal direction without inducing a gimbal lock phenomenon.

Here, when the first link 1120 rotates around the first yaw axis Y1 with respect to the base link 1115, the second link 1140, the third link 1140, the fourth link 1150, the fifth link 1160, and the surgical instrument 1200 that are connected to the first link 1120 rotate around the first yaw axis Y1 together with the first link 1120. Accordingly, a coordinate system of the surgical instrument 1200 and each of the links is not fixed but is relatively continuously changed according to the rotation of the first link 1120. However, for convenience of description, in the present specification, unless described otherwise, the description will be provided based on the state in which the second link 1130 is positioned parallel to the X-axis as shown in FIG. 32.

Meanwhile, the second joint 1172 connects the second link 1130 to the first link 1120. In this case, since the second link 1130 is fixedly coupled the first link 1120, a relative position of the second link 1130 with respect to the first link 1120 may be formed to be constant. That is, the second link 1130 and the first link 1120 may operate together as one body. Here, the second link 1130 and the first link 1120 are illustrated as being formed as separate members and fixedly coupled to each other, but the concept of the present disclosure is not limited thereto, and it would also be possible that the second link 1130 and the first link 1120 are integrally formed and function as the yaw drive assembly 1105.

Here, in the surgical robot arm 1100 according to the seventh embodiment of the present disclosure, the second link 1130 is not formed parallel to the horizontal plane but is formed to be inclined by a certain degree. For example, the second link 1130 may be formed to be approximately parallel to the first yaw axis Y1 that is formed to be inclined.

Here, the second joint 1172 may include a motor, and may be connected to the third joint 1173 by a belt, a wire, or the like. Accordingly, a driving force of the second joint 1172 may be transmitted to the third joint 1173. Alternatively, the second joint 1172 may not include a motor, and the third joint 1173 may be formed to include a motor.

The third link 1140 is axially coupled to the second link 1130 so as to be rotatable around the third joint 1173 with respect to the second link 1130. Here, the third joint 1173 may include one or more pulleys.

The fourth link 1150 is axially coupled to the third link 1140 so as to be rotatable around the fourth joint 1174 with respect to the third link 1140. Here, the fourth joint 1174 may include one or more pulleys.

The fifth link 1160 is axially coupled to the fourth link 1150 so as to be rotatable around the fifth joint 1175 with respect to the fourth link 1150. Here, the fifth joint 1175 may include one or more pulleys.

The surgical instrument 1200 is coupled to the fifth link 1160. In this case, at least a portion of the surgical instrument 1200 is formed to be rotatable around a roll axis (i.e., a shaft axis), and is formed to be linearly reciprocally movable along a roll axis R with respect to the fifth link 1160. Here, the roll axis R of the surgical instrument 1200 is formed to pass through the RCM.

Meanwhile, although not shown in the drawings, an instrument mounting part (not shown) and a guide rail (not shown) are formed in the fifth link 1160, which is an instrument mounting link, and the instrument mounting part (not shown) may linearly move along the guide rail (not shown), which is formed in a direction of the roll axis R, in a state in which the surgical instrument 1200 is mounted on the instrument mounting part (not shown). In order to implement such a linear movement, a linear actuator (not shown) may be provided in the instrument mounting part (not shown).

In addition, the surgical instrument 1200 may be mounted on the above-described instrument mounting part (not shown) of the fifth link 1160 of the surgical robot arm 1100.

Meanwhile, the third link 1140, the fourth link 1150, and the fifth link 1160 form a parallelogram, and configure a kind of RCM mechanism.

In detail, the third joint 1173, the fourth joint 1174, the fifth joint 1175, and the RCM may be four vertices of a parallelogram. That is, the third joint 1173, the fourth joint 1174, the fifth joint 1175, and the RCM may form a single parallelogram.

In detail, when three vertices, which are the third joint 1173, the fourth joint 1174, and the fifth joint 1175, are established, the position of the RCM in the parallelogram including these three vertices is automatically defined.

In addition, when the third link 1140 rotates around the third joint 1173 in a state in which the position of the third joint 1173 is fixed, due to the RCM mechanism of a link/belt described above, the third link 1140 and the fifth link 1160 rotate while maintaining a parallel state, and the fourth link 1150 and the extension line connecting the third joint 1173 to the RCM also rotate while maintaining a parallel state. Accordingly, the RCM may remain constant in position regardless of the rotation angle of the third link 1140.

In this structure, once the surgical robot arm is set up, the RCM always maintains its position. In addition, whenever each of the links rotates around the RCM, regardless of its position, the links maintain the parallelogram. That is, in a state in which the body 1110 and the base link 1115 are fixed, the position of the RCM will not change no matter where the third link 1140 or the fifth link 1160 is positioned, and the third joint 1173, the fourth joint 1174, the fifth joint 1175, and the RCM maintain the parallelogram.

Meanwhile, in the seventh embodiment of the present disclosure, each of the links, in particular, the second link 1130, the third link 1140, the fourth link 1150, and the fifth link 1160 are arranged side by side without overlapping each other, so that no collision occurs when one link rotates with respect to another link. In addition, the links are formed in such a manner that no one link interferes with the rotation of another link, so that a driving range of each link is increased.

In detail, referring to FIG. 36B, which is a plan view of the surgical robot arm 1100 according to an embodiment of the present disclosure, or the like, when viewed from the XY plane, each of the second link 1130, the third link 1140, the fourth link 1150, and the fifth link 1160 is formed to be offset by a certain degree in a direction of the rotation axes thereof (i.e., the Y-axis direction). In other words, based on the Y-axis direction, the third link 1140 is disposed on one side of the second link 1130, the fourth link 1150 is disposed on one side of the third link 1140, and the fifth link 1160 is disposed on one side of the fourth link 1150. In other words, it may be expressed that the second link 1130, the third link 1140, the fourth link 1150, and the fifth link 1160 are sequentially arranged in the Y-axis direction.

In particular, by disposing the fifth link 1160, on which the surgical instrument 1200 is mounted, to be offset by a certain degree with respect to the fourth link 1150, a restriction on the rotation angle of the fifth link 1160 (and the surgical instrument 1200 coupled thereto) with respect to the fourth link 1150 is eliminated, thereby achieving an effect of allowing the fifth link 1160 (and the surgical instrument 1200 coupled thereto) to rotate freely.

Meanwhile, in the seventh embodiment of the present disclosure, the surgical instrument 1200 coupled to the fifth link 1160 is disposed to face outwardly of the surgical robot arm 1100.

In detail, in the fifth link 1160, a surface on which the instrument mounting part is formed, or, in other words, a surface to which the surgical instrument 1200 is coupled is assumed to be a first surface, and a surface opposite to the surface is assumed to be a second surface.

At this time, in a state in which an end tool 1210 of the surgical instrument 1200 coupled to the fifth link 1160 faces vertically downward, the first surface is disposed to face a direction away from the body 1110. In other words, the surgical instrument 2200 coupled to the first surface of the fifth link 1160 is disposed farther from the body 1110 than the fifth link 1160.

Meanwhile, in a state in which the surgical instrument 1200 coupled to the fifth link 1160 is horizontally disposed and the end tool 1210 is disposed in a direction away from the body 1110, the first surface is disposed to face upward. In other words, the surgical instrument 1200 coupled to the first surface of the fifth link 1160 is disposed above the fifth link 1160.

Operations of Surgical Robot Arm

FIGS. 36 to 38 are views illustrating an RCM motion (pitch motion) of the surgical robot arm of FIG. 32 around the pitch axis P, each view including both a side view and a plan view.

As shown in FIGS. 36 to 38, when a motor (not shown) is driven, the third link 1140 rotates around the third joint 1173 with respect to the second link 1130. In addition, in conjunction therewith, the fourth link 1150 rotates with respect to the third link 1140, and the fifth link 1160 rotates with respect to the fourth link 1150. At this time, due to the above-described belt or link structure, the fourth link 1150 and the extension line connecting the third joint 1173 to the RCM maintain a parallel state, and the third link 1140 and the fifth link 1160 maintain a parallel state. In other words, the RCM remains constant even in any state of motion of the surgical robot arm 1100 around the pitch axis P.

Meanwhile, as shown in the plan view of each drawing, the second link 1130, the third link 1140, the fourth link 1150, and the fifth link 1160 may be disposed to be adjacent to each other without overlapping each other in the Y-axis direction.

FIGS. 39 to 41 are perspective views illustrating an RCM motion (yaw motion) of the surgical robot arm of FIG. 32 around the first yaw axis Y1.

As shown in FIGS. 39 to 41, when a motor (not shown) is driven, the first link 1120 of the yaw drive assembly 1105 rotates around the first yaw axis Y1 with respect to the base link 1115. At this time, since the first yaw axis Y1 passes through the RCM, the RCM remains constant no matter what angle the first link 1120 rotates with respect to the base link 1115.

FIG. 42 is a view illustrating a state in which the fifth link 1160 of the surgical robot arm 1100 of FIG. 32 and the surgical instrument 1200 coupled thereto are disposed parallel to each other.

As described above, the surgical robot arm 1100 according to the seventh embodiment of the present disclosure is formed such that the first yaw axis Y1 and the extension line connecting the third joint 1173 to the RCM are different from each other, so that the fifth link 1160 and the surgical instrument 1200 coupled thereto can be disposed in the horizontal direction without inducing a gimbal lock phenomenon.

FIG. 43 is a view illustrating a state in which the surgical robot arm 1100 illustrated in FIG. 42 is disposed near the patient's surgical site, and the surgical instrument 1200 is disposed directly facing the patient.

As described above, in the surgical robot arm 1100 according to the seventh embodiment of the present disclosure, each robot arm is formed in a modular manner, and the fifth link 1160 and the surgical instrument 1200 coupled thereto may be disposed parallel to each other. Accordingly, each modular surgical robot arm 1100 may be disposed near the patient's surgical site, and the surgical instrument 1200 may be disposed directly facing the patient.

FIG. 44 is a view illustrating a state in which the end tool 1210 of the surgical instrument 1200 coupled to the fifth link 1160 of the surgical robot arm 1100 of FIG. 32 is disposed facing upward from below.

As described above, the surgical robot arm 1100 according to the seventh embodiment of the present disclosure is formed such that the first yaw axis Y1 and the extension line connecting the third joint 1173 to the RCM intersect each other at the RCM, so that the surgical instrument 1200 can be disposed facing upward from below, beyond the horizontal direction.

According to the seventh embodiment of the present disclosure described above, by forming the first yaw axis Y1 and the extension line connecting the third joint 1173 to the RCM to be different from each other, the fifth link 1160 and the surgical instrument 1200 coupled thereto can be disposed in the horizontal direction without inducing a gimbal lock phenomenon. Furthermore, the surgical instrument 1200 can be disposed facing upward from below, beyond the horizontal direction.

Further, by disposing each of the links to be offset by a certain degree, the rotational motion of each link is not constrained by another link, so that the range of motion of the instrument is increased, such as the moving direction of the instrument is directed upward beyond the horizontal direction. Accordingly, even in the frequent case of surgery, in which the instrument is disposed in the horizontal direction, an effect of preventing the gimbal lock and allowing the instrument to move with a sufficient range of motion may be obtained.

<Eighth Embodiment of Surgical Robot Arm>

Hereinafter, a surgical robot arm 1600 according to an eighth embodiment of the present disclosure will be described. Here, the surgical robot arm 1600 according to the eighth embodiment of the present disclosure is different from the surgical robot arm (see 1100 in FIG. 32 or the like) according to the seventh embodiment of the present disclosure described above in that a setup link assembly 1690 is further included. Such a configuration that is changed from that of the seventh embodiment will be described in detail below.

Figure 46:
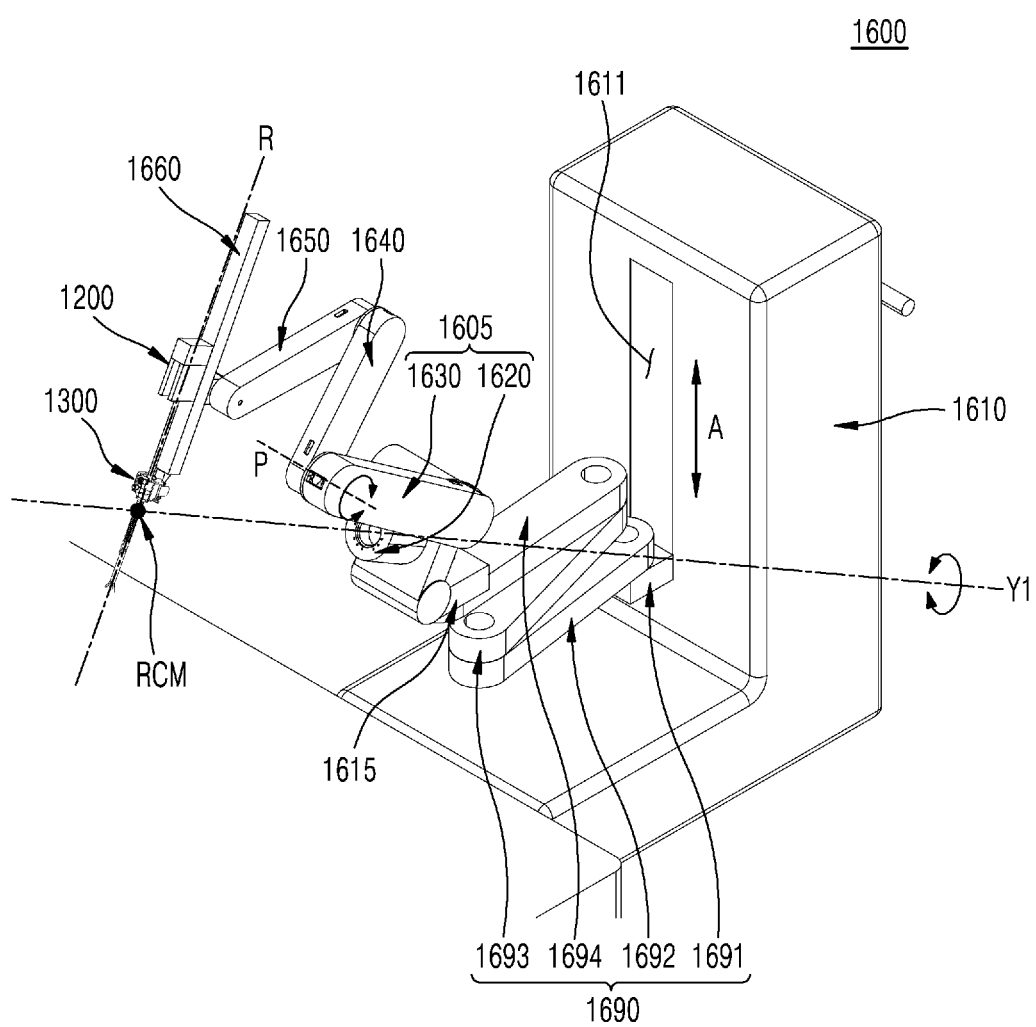
FIG. 46 is a perspective view illustrating a surgical robot arm according to an eighth embodiment of the present disclosure.

FIG. 46 is a perspective view illustrating the surgical robot arm according to the eighth embodiment of the present disclosure.

Referring to FIG. 46, the surgical robot arm 1600 according to the eighth embodiment of the present disclosure includes a body 1610, a base link 1615, a yaw drive assembly 1605, a third link 1640, a fourth link 1650, and a fifth link 1660. Here, the yaw drive assembly 1605 may include a first link 1620 and a second link 1630. Further, the surgical robot arm 1600 according to the eighth embodiment of the present disclosure further includes the setup link assembly 1690. In addition, as in the seventh embodiment illustrated with reference to FIG. 32, the surgical robot arm 1600 of the present embodiment may include a first joint (see 1171 in FIG. 35), a second joint (sec 1172 in FIG. 35) a third joint (see 1173 in FIG. 35), a fourth joint (see 1174 in FIG. 35), and a fifth joint (sec 1175 in FIG. 35). In addition, a trocar 1300 and a surgical instrument 1200 are coupled to the fifth link 1660 of the surgical robot arm 1600 described above.

Here, the body 1610 serves as a base of the entire surgical robot arm 1600.

Meanwhile, the base link 1615 may be formed on one surface of the body 1610, for example, an upper surface thereof. The base link 1615 may be formed to be inclined by a certain degree to have a predetermined angle with respect to a horizontal plane.

Meanwhile, the yaw drive assembly 1605 is rotatably coupled to the base link 1615. The yaw drive assembly 1605 is coupled to the base link 1615 by the first joint (see 1171 in FIG. 35), and may be formed to be yaw rotatable around a first yaw axis Y1 with respect to the base link 1615.

Here, the yaw drive assembly 1605 may include the first link 1620 and the second link 1630. The yaw drive assembly 1605 is coupled to the base link 1615 by the first joint (sec 1171 in FIG. 35), and may be formed to be yaw rotatable around the first yaw axis Y1 with respect to the base link 1615. Here, the first link 1620 is coupled to the base link 1615 by the first joint (sec 1171 in FIG. 35), and is formed to be yaw rotatable around the first yaw axis Y1 with respect to the base link 1615. In addition, one end portion of the second link 1630 is fixedly coupled to the first link 1620, and another end portion thereof is coupled to the third link 1640 to be described later.

The third link 1640 is axially coupled to the second link 1630 so as to be rotatable around the third joint (see 1173 in FIG. 35) with respect to the second link 1630. Here, the third joint (see 1173 in FIG. 35) may include one or more pulleys.

The fourth link 1650 is axially coupled to the third link 1640 so as to be rotatable around the fourth joint (see 1174 in FIG. 35) with respect to the third link 1640. Here, the fourth joint (see 1174 in FIG. 35) may include one or more pulleys.

The fifth link 1660 is axially coupled to the fourth link 1650 so as to be rotatable around the fifth joint (see 1175 in FIG. 35) with respect to the fourth link 1650. Here, the fifth joint (see 1175 in FIG. 35) may include one or more pulleys.

The surgical instrument 1200 is coupled to the fifth link 1660.

Here, the third link 1640, the fourth link 1650, and the fifth link 1660 form a parallelogram, and configure a kind of RCM mechanism. That is, when the third link 1640 rotates around the third joint (see 1173 in FIG. 35) in a state in which the position of the third joint (see 1173 in FIG. 35) is fixed, due to the RCM mechanism of a link/belt described above, the third link 1640 and the fifth link 1660 rotate while maintaining a parallel state, and the fourth link 1650 and the extension line connecting the third joint (see 1173 in FIG. 35) to the RCM also rotate while maintaining a parallel state. Accordingly, the RCM may remain constant in position regardless of the rotation angle of the third link 1640.

Here, the surgical robot arm 1600 according to the eighth embodiment of the present disclosure further includes the setup link assembly 1690. That is, the setup and positioning of the surgical robot arm 1600 can be more easily performed by further including the setup link assembly 1690, which is formed between the body 1610 and the base link 1615, connects the body 1610 to the base link 1615, and allows the base link 1615 (and the links connected thereto) to move vertically or horizontally with respect to the body 1610. This will be described in more detail below.

In detail, the setup link assembly 1690 may include a vertical setup link 1691 and one or more horizontal setup links 1692, 1693, and 1694.

The vertical setup link 1691 is connected to the body 1610, and formed to be movable in the Z-axis direction with respect to the body 1610.

Here, a guide groove 1611 is vertically formed in the body 1610, and the vertical setup link 1691 is linearly movable up and down along the guide groove 1611 in the direction of an arrow A.

Meanwhile, the setup link assembly 1690 may include a first horizontal setup link 1692, a second horizontal setup link 1693, and a third horizontal setup link 1694. The first horizontal setup link 1692 is axially coupled to the vertical setup link 1691 so as to be rotatable with respect thereto. The second horizontal setup link 1693 is axially coupled to the first horizontal setup link 1692 so as to be rotatable with respect thereto. One end portion of the third horizontal setup link 1693 is rotatably axially coupled to the second horizontal setup link 1692. In addition, the base link 1615 is formed at another end portion of the second horizontal setup link 1693.

As described above, since the setup link assembly 1690 includes one or more horizontal setup links 1692, 1693, and 1694, the base link 1615 connected to the setup link assembly 1690 may be disposed in various setup positions on the XY plane.

Meanwhile, in the drawing, it is illustrated that the vertical setup link 1691 is connected to the body 1610 and the horizontal setup links 1692, 1693, and 1694 are connected to the vertical setup link 1691, but the concept of the present disclosure is not limited thereto. That is, a configuration in which the horizontal setup links are connected to the body 1610 and the vertical setup link is connected to the horizontal setup links is also possible. Alternatively, a configuration in which only one of the vertical setup link and the horizontal setup link is provided is also possible. Alternatively, various configurations and arrangements of the horizontal setup links and vertical setup link are possible, such as a configuration in which the vertical link is disposed in the middle of a plurality of horizontal setup links.

Here, the setup link assembly 1690 may be formed to be operative only during a period in which the surgical robot arm 1600 is deployed at an appropriate position on one side of a patient before the surgical robot arm 1600 actually begins to perform a surgery, and to remain in a fixed state without moving during a period in which the surgical robot arm 1600 is completely deployed and actually performs a surgery. To this end, although not shown in the drawings, the setup link assembly 1690 may further include a brake module (not shown) capable of maintaining a stationary state, and the brake module may further include a manipulation member (not shown) capable of selecting an activated/deactivated state.

By further including the setup link assembly 1690 as described above, the setup and positioning of the surgical robot arm 1600 can be more easily performed.

<Ninth Embodiment of Surgical Robot Arm>

Hereinafter, a surgical robot arm 1700 according to a ninth embodiment of the present disclosure will be described. Here, the surgical robot arm 1700 according to the ninth embodiment of the present disclosure is different from the surgical robot arm (see 1100 in FIG. 32 or the like) according to the seventh embodiment of the present disclosure described above in that a setup link assembly 1790 is further included. Such a configuration that is changed from that of the seventh embodiment will be described in detail below.

Figure 47:
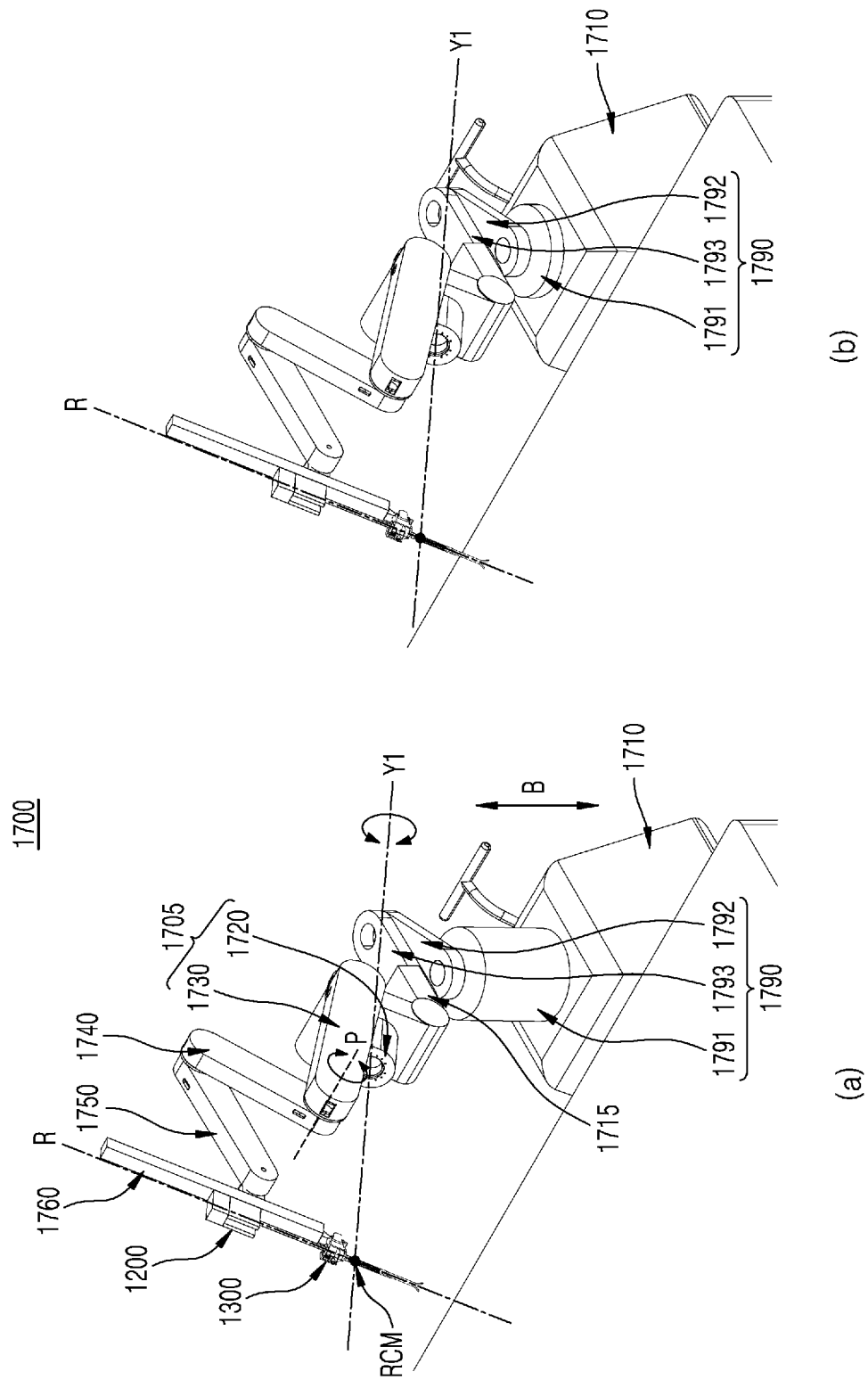
FIG. 47 is a perspective view illustrating a surgical robot arm according to a ninth embodiment of the present disclosure.

FIG. 47 is a perspective view illustrating the surgical robot arm according to the ninth embodiment of the present disclosure.

Referring to FIG. 47, the surgical robot arm 1700 according to the ninth embodiment of the present disclosure includes a body 1710, a base link 1715, a yaw drive assembly 1705, a third link 1740, a fourth link 1750, and a fifth link 1760. Here, the yaw drive assembly 1705 may include a first link 1720 and a second link 1730. In addition, the surgical robot arm 1700 according to the ninth embodiment of the present disclosure further includes a setup link assembly 1790. In addition, as in the seventh embodiment illustrated with reference to FIG. 32, the surgical robot arm 1700 of the present embodiment may include a first joint (see 1171 in FIG. 35), a second joint (sec 1172 in FIG. 35) a third joint (see 1173 in FIG. 35), a fourth joint (see 1174 in FIG. 35), and a fifth joint (see 1175 in FIG. 35). In addition, a trocar 1300 and a surgical instrument 1200 are coupled to the fifth link 1760 of the surgical robot arm 1700 described above.

Here, the body 1710 serves as a base of the entire surgical robot arm 1700.

Meanwhile, the base link 1715 may be formed on one surface of the body 1710, for example, an upper surface thereof. The base link 1715 may be formed to be inclined by a certain degree to have a predetermined angle with respect to a horizontal plane.

Meanwhile, the yaw drive assembly 1705 is rotatably coupled to the base link 1715. The yaw drive assembly 1705 is coupled to the base link 1715 by the first joint (see 1171 in FIG. 35), and may be formed to be yaw rotatable around the first yaw axis Y1 with respect to the base link 1715.

Here, the yaw drive assembly 1705 may include the first link 1720 and the second link 1730. The yaw drive assembly 1705 is coupled to the base link 1715 by the first joint (see 1171 in FIG. 35), and may be formed to be yaw rotatable around the first yaw axis Y1 with respect to the base link 1715. Here, the first link 1720 is coupled to the base link 1715 by the first joint (see 1171 in FIG. 35), and is formed to be yaw rotatable around the first yaw axis Y1 with respect to the base link 1715. In addition, in the second link 1730, one end portion is fixedly coupled to the first link 1720, and another end portion is coupled to the third link 1740 to be described later.

The third link 1740 is axially coupled to the second link 1730 so as to be rotatable around the third joint (see 1173 in FIG. 35) with respect to the second link 1730. Here, the third joint (see 1173 in FIG. 35) may include one or more pulleys.

The fourth link 1750 is axially coupled to the third link 1740 so as to be rotatable around the fourth joint (see 1174 in FIG. 35) with respect to the third link 1740. Here, the fourth joint (see 1174 in FIG. 35) may include one or more pulleys.

The fifth link 1760 is axially coupled to the fourth link 1750 so as to be rotatable around the fifth joint (see 1175 in FIG. 35) with respect to the fourth link 1750. Here, the fifth joint (see 1175 in FIG. 35) may include one or more pulleys.

The surgical instrument 1200 is coupled to the fifth link 1760.

In this case, the third link 1740, the fourth link 1750, and the fifth link 1760 form a parallelogram, and configure a kind of RCM mechanism. That is, when the third link 1740 rotates around the third joint (see 1173 in FIG. 35) in a state in which the position of the third joint (see 1173 in FIG. 35) is fixed, due to the RCM mechanism of a link/belt described above, the third link 1740 and the fifth link 1760 rotate while maintaining a parallel state, and the fourth link 1750 and the extension line connecting the third joint (see 1173 in FIG. 35) to the RCM also rotate while maintaining a parallel state. Accordingly, the RCM may remain constant in position regardless of the rotation angle of the third link 1740.

Here, the surgical robot arm 1700 according to the ninth embodiment of the present disclosure further includes the setup link assembly 1790. That is, the setup and positioning of the surgical robot arm 1700 can be more easily performed by further including the setup link assembly 1790, which is formed between the body 1710 and the base link 1715, connects the body 1710 to the base link 1715, and allows the base link 1715 (and the links connected thereto) to move vertically or horizontally with respect to the body 1710. This will be described in more detail below.

In detail, the setup link assembly 1790 may include a vertical setup link 1791 and one or more horizontal setup links 1792 and 1793.

The vertical setup link 1791 is connected to the body 1710, and formed to be movable in the Z-axis direction with respect to the body 1710.

Here, the vertical setup link 1791 is formed in a cylindrical shape, and thus, linearly movable up and down while being drawn in or out from the body 1710 in the direction of an arrow B.

Meanwhile, the setup link assembly 1790 may include a first horizontal setup link 1792 and a second horizontal setup link 1793. The first horizontal setup link 1792 is axially coupled to the vertical setup link 1791 so as to be rotatable with respect thereto. The second horizontal setup link 1793 is axially coupled to the first horizontal setup link 1792 so as to be rotatable with respect thereto. In addition, the base link 1715 is formed at another end portion of the second horizontal setup link 1792.

As described above, since the setup link assembly 1790 includes one or more horizontal setup links 1792 and 1793, the base link 1715 connected to the setup link assembly 1790 may be disposed in various setup positions on the XY plane.

Meanwhile, in the drawing, it is illustrated that the vertical setup link 1791 is connected to the body 1710 and the horizontal setup links 1792 and 1793 are connected to the vertical setup link 1791, but the concept of the present disclosure is not limited thereto. That is, a configuration in which the horizontal setup links are connected to the body 1710 and the vertical setup link is connected to the horizontal setup links is also possible. Alternatively, a configuration in which only one of the vertical setup link and the horizontal setup link is provided is also possible. Alternatively, various configurations and arrangements of the horizontal setup links and vertical link are possible, such as a configuration in which the vertical setup link is disposed in the middle of a plurality of horizontal setup links.

Here, the setup link assembly 1790 may be formed to be operative only during a period in which the surgical robot arm 1700 is deployed at an appropriate position on one side of a patient before the surgical robot arm 1700 actually begins to perform a surgery, and to remain in a fixed state without moving during a period in which the surgical robot arm 1700 is completely deployed and actually performs a surgery. To this end, although not shown in the drawings, the setup link assembly 1790 may further include a brake module (not shown) capable of maintaining a stationary state, and the brake module may further include a manipulation member (not shown) capable of selecting an activated/deactivated state.

By further including the setup link assembly 1790 as described above, the setup and positioning of the surgical robot arm 1700 can be more easily performed.

<Tenth Embodiment of Surgical Robot Arm>

Hereinafter, a surgical robot arm 2100 according to a tenth embodiment of the present disclosure will be described. Here, the surgical robot arm 2100 according to the tenth embodiment of the present disclosure is different from the surgical robot arm (see 1100 in FIG. 32 or the like) according to the seventh embodiment of the present disclosure described above in that the configuration and arrangement surface of links are changed. Such a configuration that is changed from that of the seventh embodiment will be described in detail below.

Figure 48:
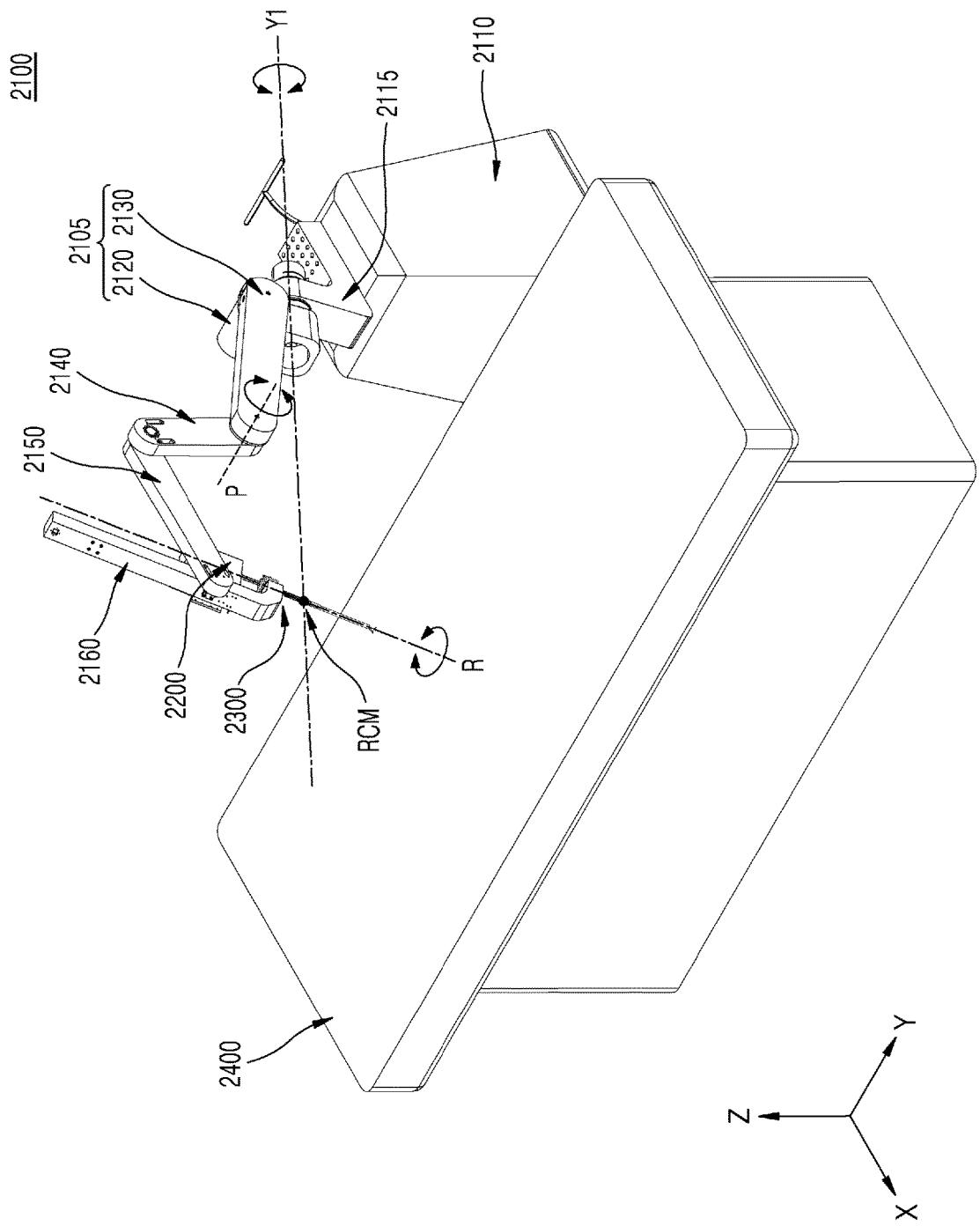
FIG. 48 is a perspective view illustrating a surgical robot arm according to a tenth embodiment of the present disclosure.
Figure 49:
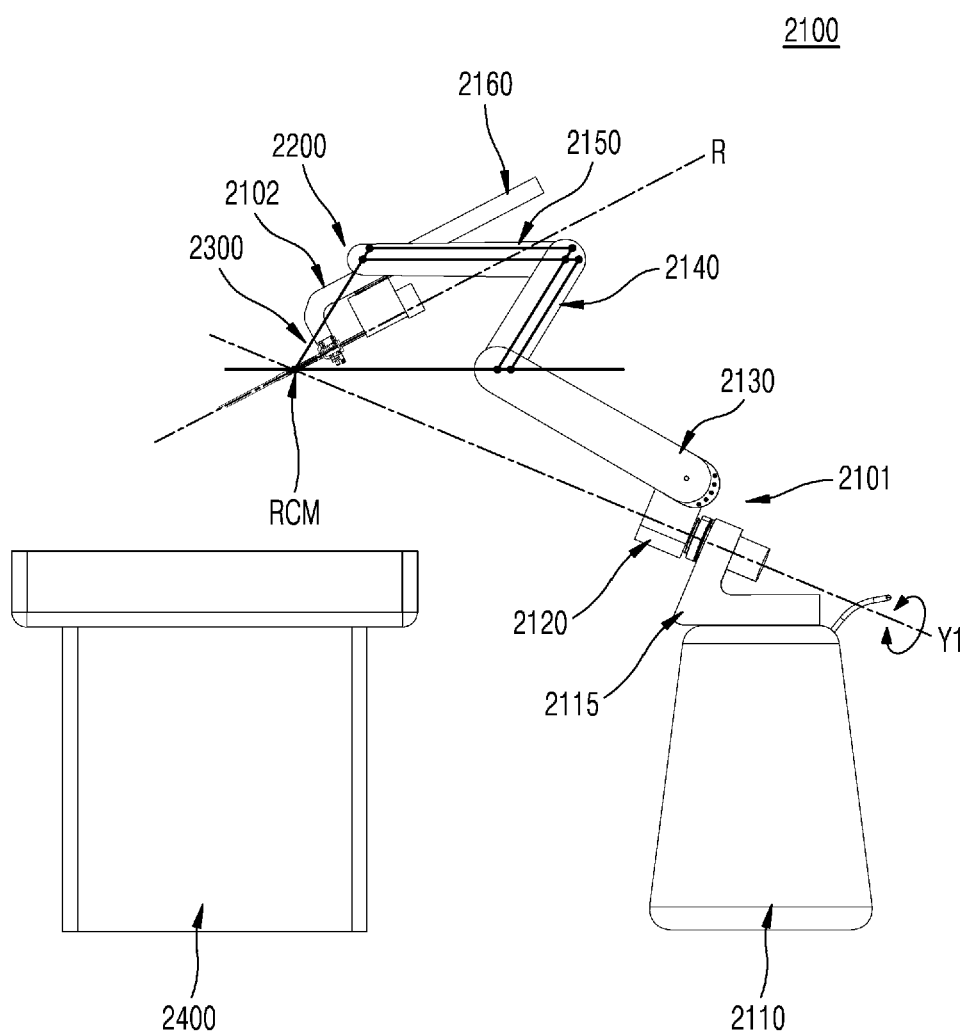
FIG. 49 is a side view of the surgical robot arm of FIG. 48.
Figure 50:
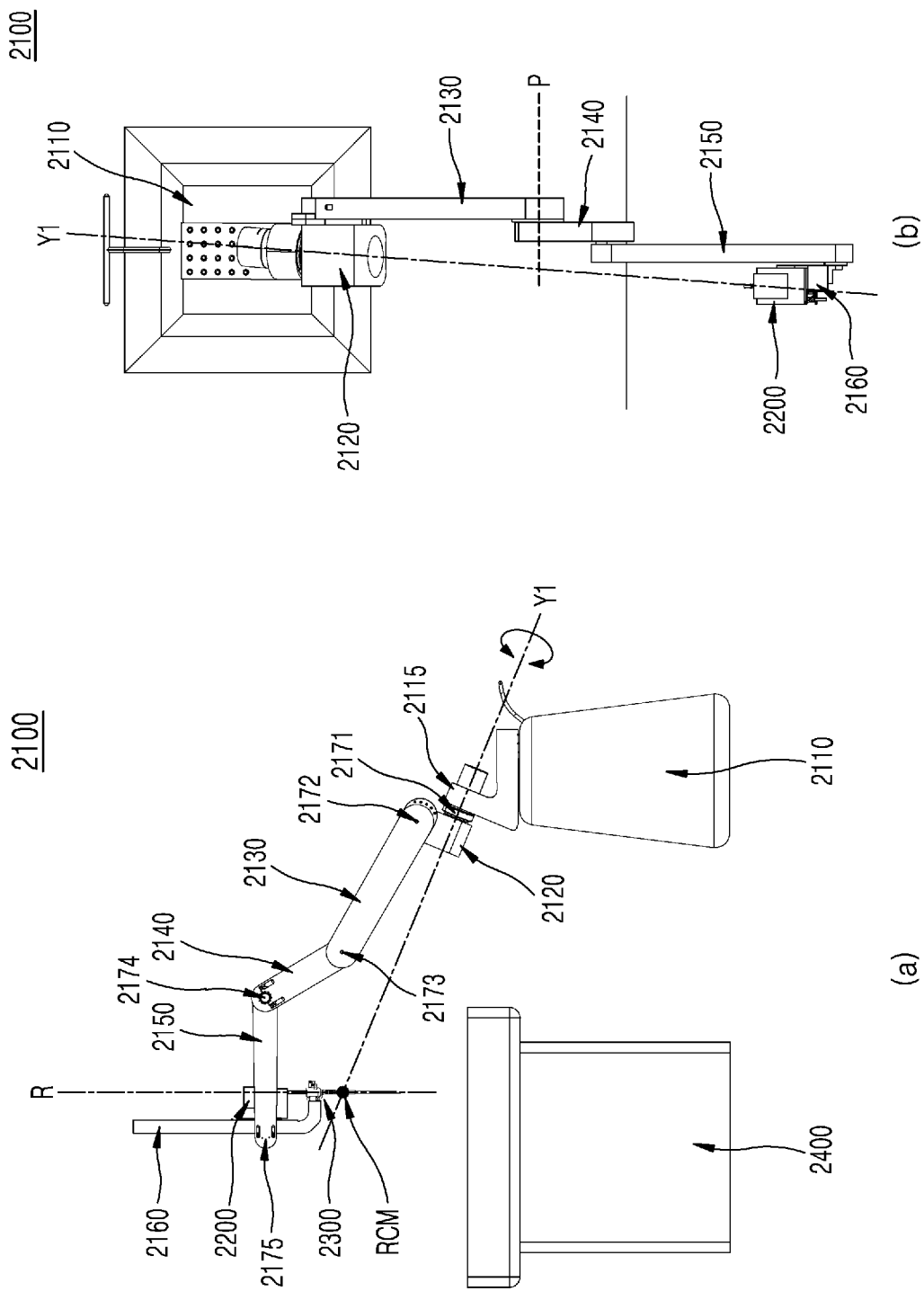
FIGS. 50 to 52 are views illustrating an RCM motion (pitch motion) of the surgical robot arm of FIG. 48 around a pitch axis P, each view including both a side view and a plan view.
Figure 51:
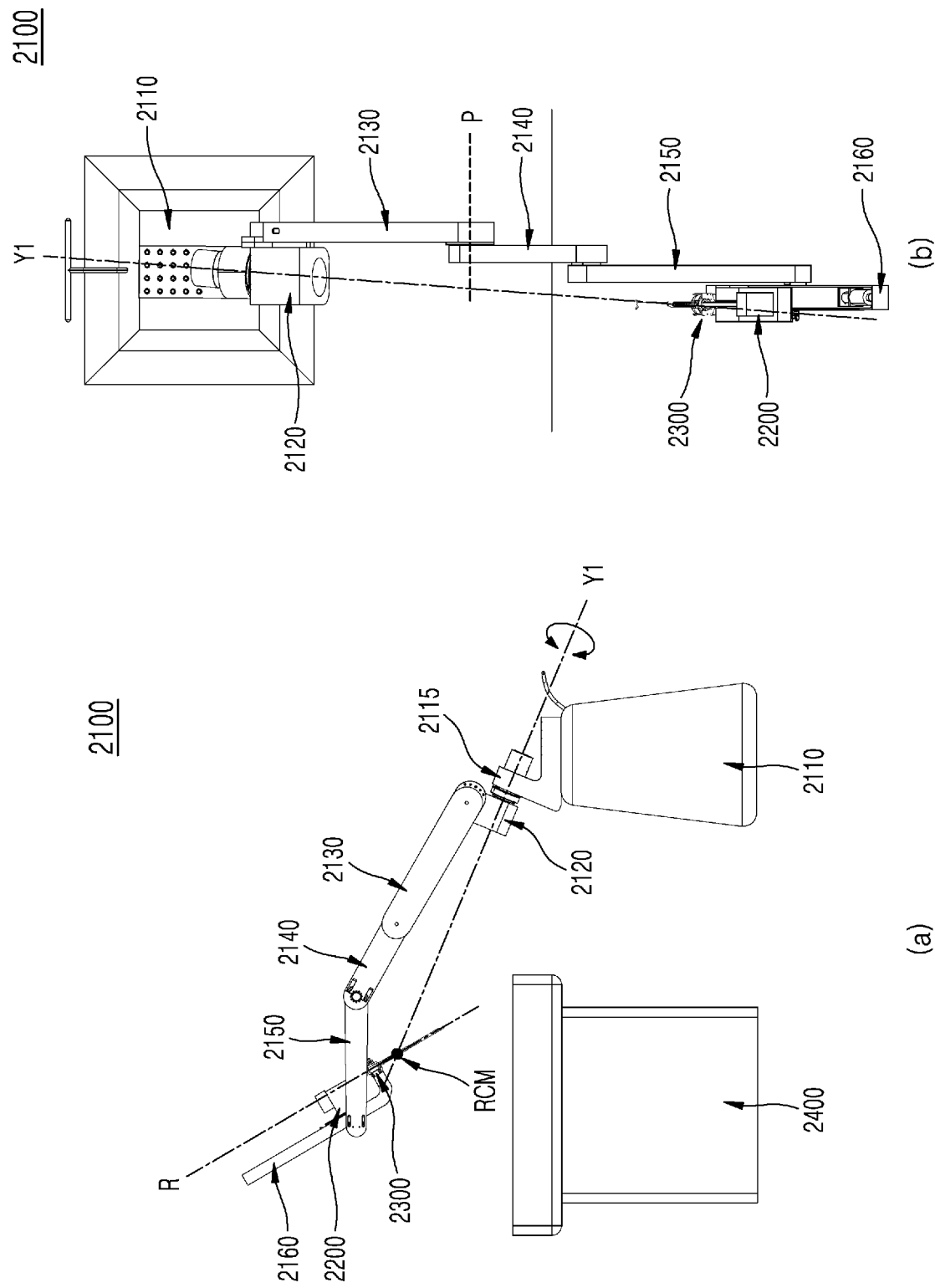
Figure 52:
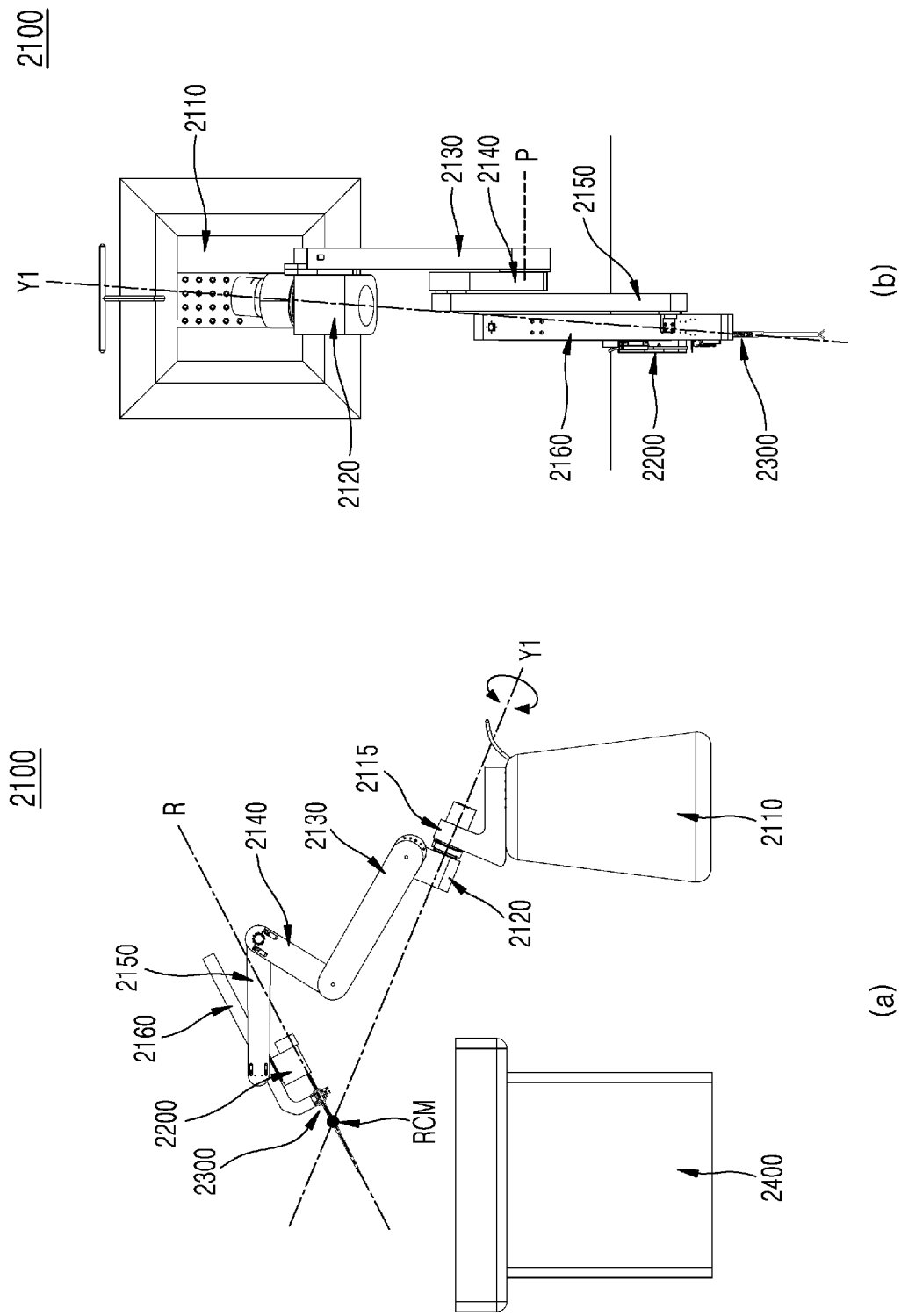
Figure 53:
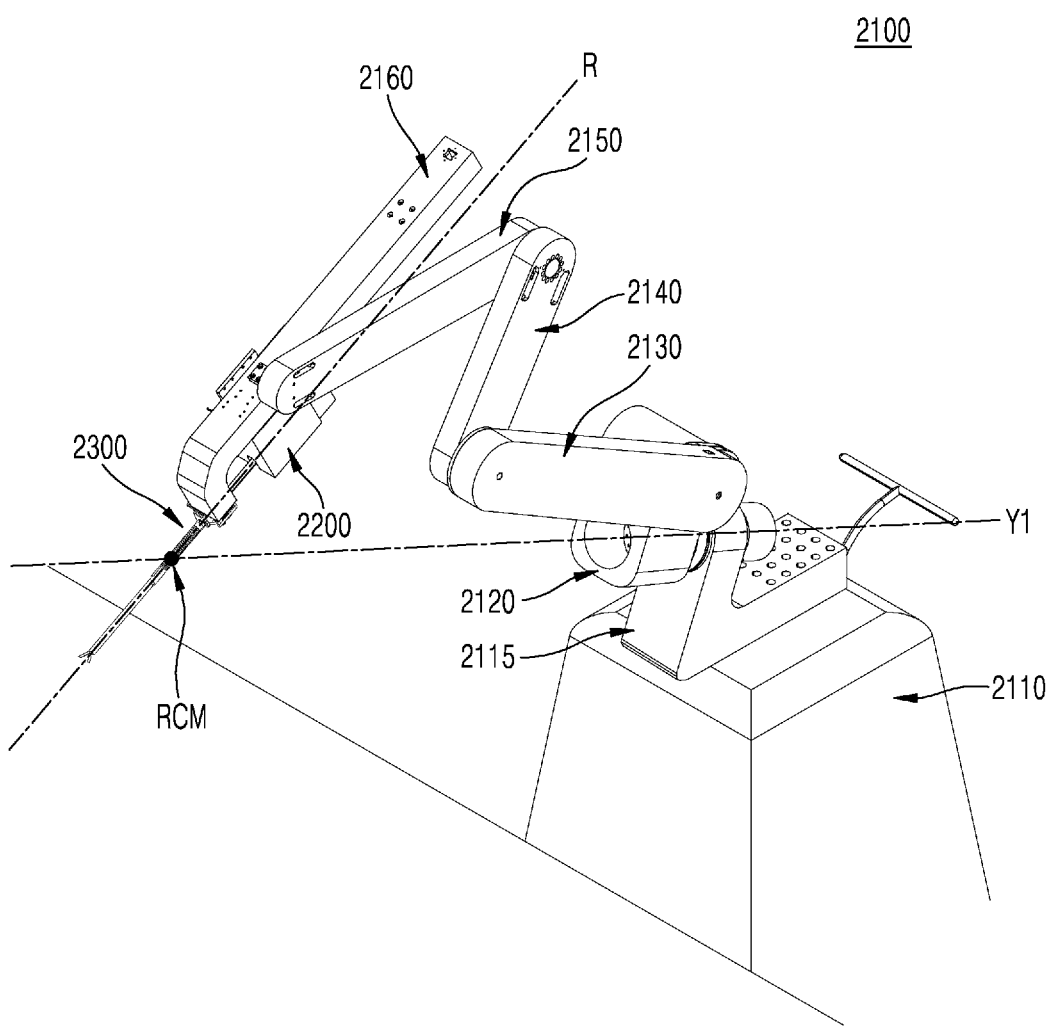
FIGS. 53 to 55 are perspective views illustrating an RCM motion (yaw motion) of the surgical robot arm of FIG. 48 around a first yaw axis Y1.
Figure 54:
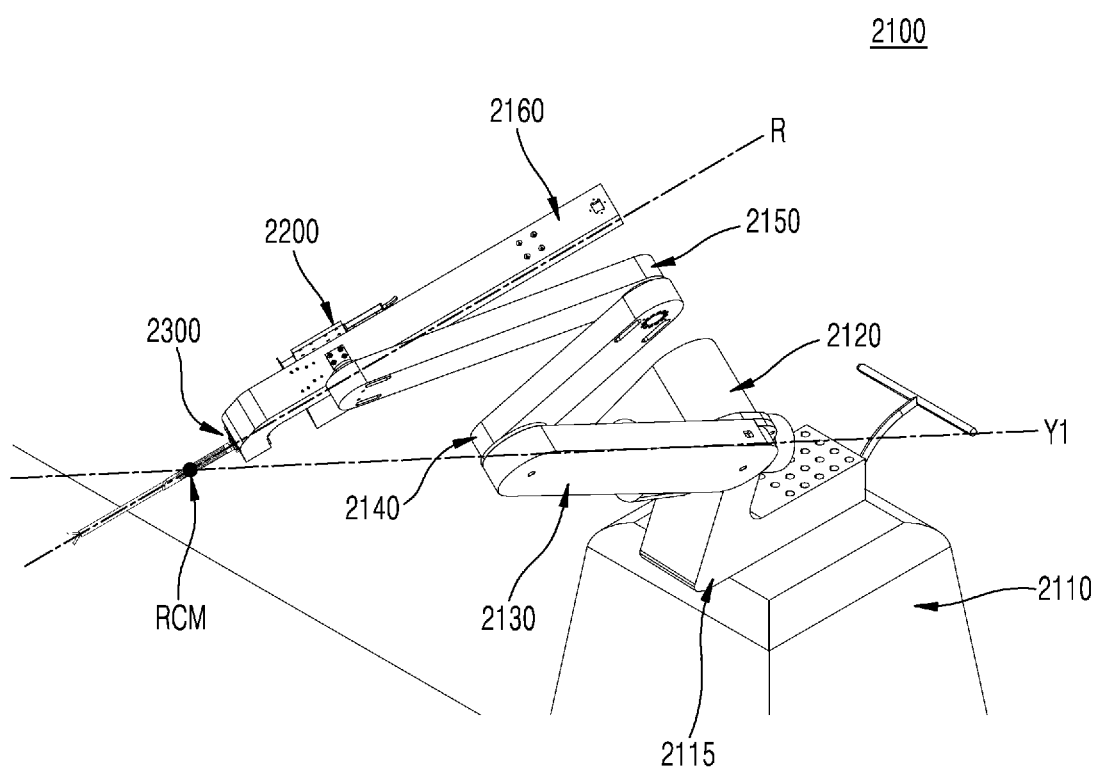
Figure 55:
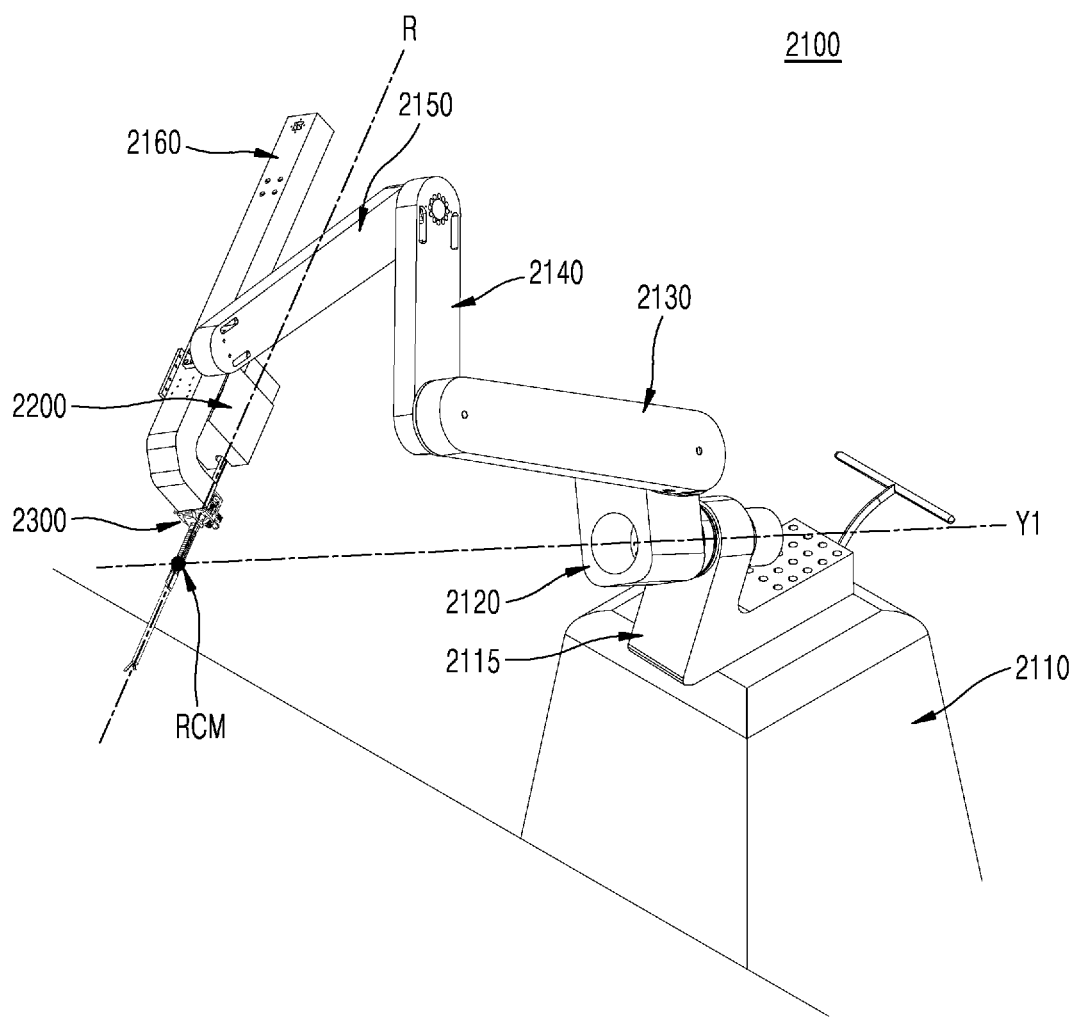
Figure 56:
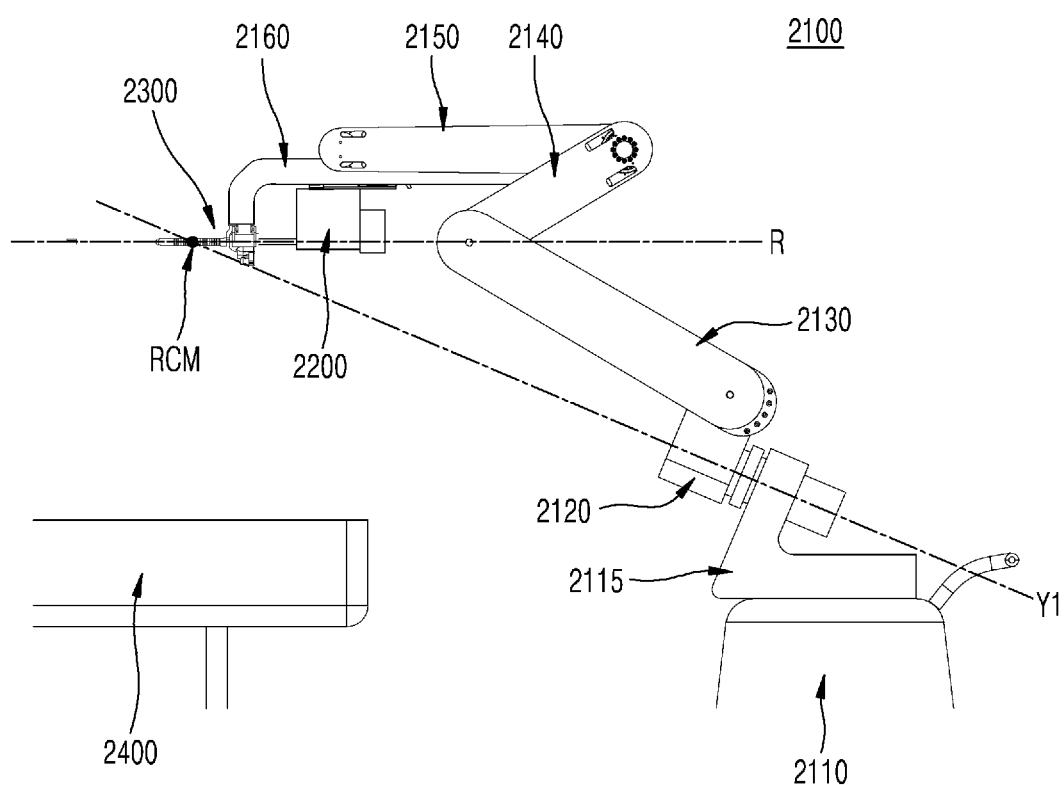
FIG. 56 is a view illustrating a state in which a fifth link of the surgical robot arm of FIG. 48 and a surgical instrument coupled thereto are disposed parallel to each other.
Figure 57:
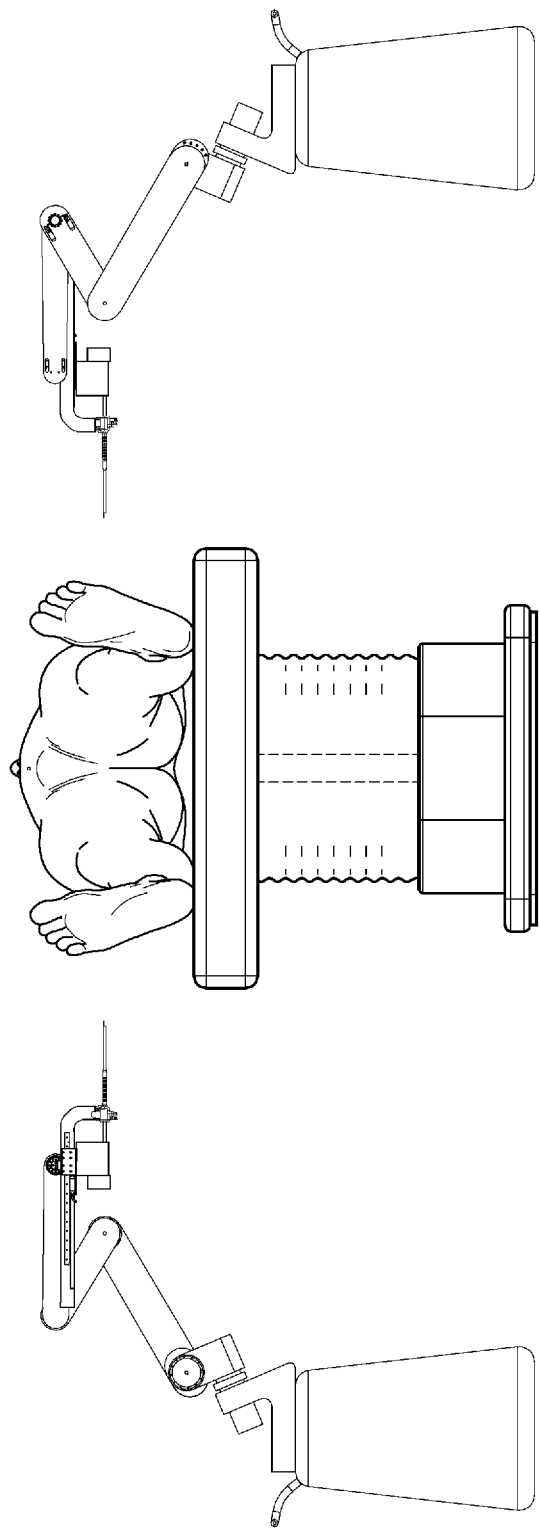
FIG. 57 is a view illustrating a state in which the surgical robot arm illustrated in FIG. 56 is disposed near a patient's surgical site and the surgical instrument is disposed directly facing a patient.
Figure 58:
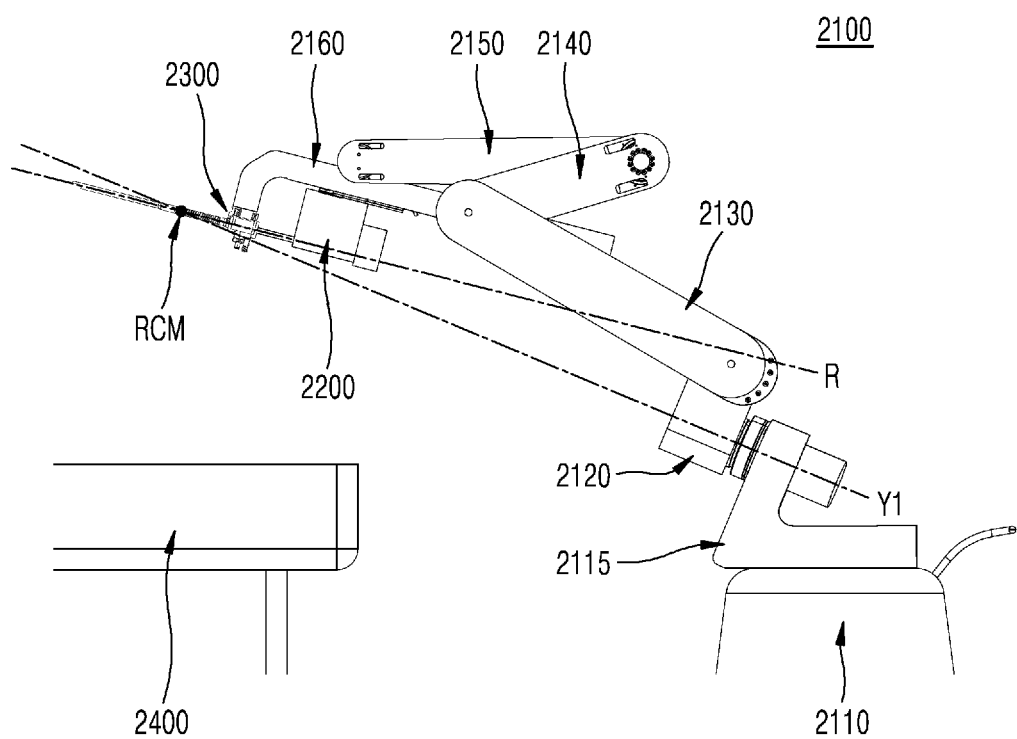
FIG. 58 is a view illustrating a state in which an end tool of the surgical instrument coupled to the fifth link of the surgical robot arm of FIG. 48 is disposed facing upward from below.

FIG. 48 is a perspective view illustrating the surgical robot arm according to the tenth embodiment of the present disclosure, and FIG. 49 is a side view of the surgical robot arm of FIG. 48. FIGS. 50 to 52 are views illustrating an RCM motion (pitch motion) of the surgical robot arm of FIG. 48 around a pitch axis P, each view including both a side view and a plan view. FIGS. 53 to 55 are perspective views illustrating an RCM motion (yaw motion) of the surgical robot arm of FIG. 48 around a first yaw axis Y1. FIG. 56 is a view illustrating a state in which a fifth link of the surgical robot arm of FIG. 48 and a surgical instrument coupled thereto are disposed parallel to each other, and FIG. 57 is a view illustrating a state in which the surgical robot arm illustrated in FIG. 56 is disposed near a patient's surgical site and the surgical instrument is disposed directly facing a patient. FIG. 58 is a view illustrating a state in which an end tool of the surgical instrument coupled to the fifth link of the surgical robot arm of FIG. 48 is disposed facing upward from below.

Referring to FIGS. 48 to 58, the surgical robot arm 2100 according to the tenth embodiment of the present disclosure includes a body 2110, a base link 2115, a yaw drive assembly 2105, a third link 2140, a fourth link 2150, and a fifth link 2160. Here, the yaw drive assembly 2105 may include a first link 2120 and a second link 2130. In addition, as in the seventh embodiment of FIG. 32, the surgical robot arm 2100 of the present embodiment may include a first joint 2171, a second joint 2172, a third joint 2173, a fourth joint 2174, and a fifth joint 2175. In addition, a trocar 2300 and a surgical instrument 2200 are coupled to the fifth link 2160 of the surgical robot arm 2100 described above.

Here, the body 2110 serves as a base of the entire surgical robot arm 2100.

Meanwhile, a base link 2115 may be formed on one surface of the body 2110, for example, an upper surface thereof. The base link 2115 may be formed to be inclined by a certain degree to have a predetermined angle with respect to a horizontal plane.

In detail, the base link 2115 may be formed in the form of a bent flat plate or wedge, with one region coupled to the upper surface of the body 2110 and another one bent region disposed to be inclined with respect to the upper surface of the body 2110. Here, the base link 2115 may be formed to be inclined by a certain degree (e.g., 30°) with respect to the horizontal plane rather than a right angle, so that the first yaw axis Y1 passing through the base link 2115 may be formed not to be parallel to the horizontal direction (i.e., the X-axis direction). This will be described in more detail later.

Meanwhile, the yaw drive assembly 2105 is rotatably coupled to the base link 2115.

In detail, the yaw drive assembly 2105 may include the first link 2120 and the second link 2130. The yaw drive assembly 2105 is coupled to the base link 2115 by the first joint 2171, and formed to be yaw rotatable around the first yaw axis Y1 with respect to the base link 2115.

Here, the first link 2120 is coupled to the base link 2115 by the first joint 2171, and formed to be yaw rotatable around the first yaw axis Y1 with respect to the base link 2115. In addition, one end portion of the second link 2130 is fixedly coupled to the first link 2120, and another end portion thereof is coupled to the third link 2140 to be described later.

In an example, the first link 2120 may be formed in a substantially cylindrical shape, and thus may yaw-rotate around the first yaw axis Y1 with respect to the base link 2115. In addition, the second link 2130 is coupled to one side of the first link 2120 having a cylindrical shape, and thus, may yaw-rotate around the first yaw axis Y1 together with the first link 2120. Here, the second link 2130 may be formed to be approximately parallel to the first yaw axis Y1. This will be described in more detail later.

The first joint 2171 rotatably couples the first link 2120 to the base link 2115. In detail, the first joint 2171 is formed so that the first link 2120 yaw-rotates around the first yaw axis Y1 formed to pass through an RCM. Here, although not shown in the drawings, the first joint 2171 may include a motor for rotating the first link 2120.

Here, the first yaw axis Y1 may be formed in an oblique direction that is not parallel to the X-axis/Y-axis/Z-axis. Specifically, the first yaw axis Y1 and an extension line connecting the third joint 2173 to the RCM may be formed to be different from each other, and the first yaw axis Y1 and the extension line connecting the third joint 2173 to the RCM may be formed to intersect each other at the RCM. In this case, the RCM to be described later may be positioned on an extension line of the first yaw axis Y1. By forming the RCM to be positioned on the extension line of the first yaw axis Y1 as described above, the position and orientation of the RCM with respect to the base link 2115 remains constant regardless of how much yaw rotation the first link 2120 has made relative to the base link 2115.

Here, as described above, as the base link 2115 is formed to be inclined by a certain degree (e.g., 30°) rather than a right angle, the first yaw axis Y1 passing through the base link 2115 may be formed not to be parallel to the horizontal direction (i.e., the X-axis direction).

In other words, it may be said that a height of the RCM in the Z-axis direction is formed to be greater than a height of a point (i.e., the first joint 2171) of the base link 2115, through which the first yaw axis Y1 passes through, in the Z-axis direction.

In other words, it may be said that a height of the first yaw axis Y1 in the Z-axis direction at a distal end 2102 of the surgical robot arm 2100 is formed to be greater than a height of the first yaw axis Y1 in the Z-axis direction at a proximal end 2101 of the surgical robot arm 2100.

Here, In other words, it may be described that the base link 2115 is formed to be inclined at a predetermined angle with respect to the horizontal plane, so that a central axis of the base link 2115 is formed to coincide with the first yaw axis Y1.

By forming the first yaw axis Y1 and the extension line connecting the third joint 2173 to the RCM to be different from each other as described above, the fifth link 2160 and the surgical instrument 2200 coupled thereto can be disposed in the horizontal direction without inducing a gimbal lock phenomenon.

When the first link 2120 rotates around the first yaw axis Y1 with respect to the base link 2115, the second link 2140, the third link 2140, the fourth link 2150, the fifth link 2160, and the surgical instrument 2200 that are connected to the first link 2120 rotate around the first yaw axis Y1 together with the first link 2120. Accordingly, a coordinate system of the surgical instrument 2200 and each of the links is not fixed but is relatively continuously changed according to the rotation of the first link 2120. However, for convenience of description, in the present specification, unless described otherwise, the description will be provided based on the state in which the second link 2130 is positioned parallel to the X-axis as shown in FIG. 48.

Meanwhile, the second joint 2172 connects the second link 2130 to the first link 2120. In this case, since the second link 2130 is fixedly coupled the first link 2120, a relative position of the second link 2130 with respect to the first link 2120 may be formed to be constant. That is, the second link 2130 and the first link 2120 may operate together as one body. Here, the second link 2130 and the first link 2120 are illustrated as being formed as separate members and fixedly coupled to each other, but the concept of the present disclosure is not limited thereto, and it would also be possible that the second link 2130 and the first link 2120 are integrally formed and function as the yaw drive assembly 2105.

Here, in the surgical robot arm 2100 according to the tenth embodiment of the present disclosure, the second link 2130 is not formed parallel to the horizontal plane but is formed to be inclined by a certain degree. For example, the second link 2130 may be formed to be approximately parallel to the first yaw axis Y1 that is formed to be inclined.

Here, the second joint 2172 may include a motor, and may be connected to the third joint 2173 by a belt, a wire, or the like. Accordingly, a driving force of the second joint 2172 may be transmitted to the third joint 2173. Alternatively, the second joint 2172 may not include a motor, and the third joint 2173 may be formed to include a motor.

The third link 2140 is axially coupled to the second link 2130 so as to be rotatable around the third joint 2173 with respect to the second link 2130. Here, the third joint 2173 may include one or more pulleys.

The fourth link 2150 is axially coupled to the third link 2140 so as to be rotatable around the fourth joint 2174 with respect to the third link 2140. Here, the fourth joint 2174 may include one or more pulleys.

The fifth link 2160 is axially coupled to the fourth link 2150 so as to be rotatable around the fifth joint 2175 with respect to the fourth link 2150. Here, the fifth joint 2175 may include one or more pulleys.

The surgical instrument 2200 is coupled to the fifth link 2160. In this case, at least a portion of the surgical instrument 2200 is formed to be rotatable around a roll axis (i.e., a shaft axis), and is formed to be linearly reciprocally movable along a roll axis R with respect to the fifth link 2160. Here, the roll axis R of the surgical instrument 2200 is formed to pass through the RCM.

Meanwhile, although not shown in the drawings, an instrument mounting part (not shown) and a guide rail (not shown) are formed in the fifth link 2160, which is an instrument mounting link, and the instrument mounting part (not shown) may linearly move along the guide rail (not shown), which is formed in a direction of the roll axis R, in a state in which the surgical instrument 2200 is mounted on the instrument mounting part (not shown). In order to implement such a linear movement, a linear actuator (not shown) may be provided in the instrument mounting part (not shown).

In addition, the surgical instrument 2200 may be mounted on the above-described instrument mounting part (not shown) of the fifth link 2160 of the surgical robot arm 2100.

Meanwhile, the third link 2140, the fourth link 2150, and the fifth link 2160 form a parallelogram, and configure a kind of RCM mechanism.

In detail, the third joint 2173, the fourth joint 2174, the fifth joint 2175, and the RCM may be four vertices of a parallelogram. That is, the third joint 2173, the fourth joint 2174, the fifth joint 2175, and the RCM may form a single parallelogram.

In detail, when three vertices, which are the third joint 2173, the fourth joint 2174, and the fifth joint 2175, are established, the position of the RCM in the parallelogram including these three vertices is automatically defined.

In addition, when the third link 2140 rotates around the third joint 2173 in a state in which the position of the third joint 2173 is fixed, due to the RCM mechanism of a link/belt described above, the third link 2140 and the fifth link 2160 rotate while maintaining a parallel state, and the fourth link 2150 and the extension line connecting the third joint 2173 to the RCM also rotate while maintaining a parallel state. Accordingly, the RCM may remain constant in position regardless of the rotation angle of the third link 2140.

In this structure, once the surgical robot arm is set up, the RCM always maintains its position. In addition, whenever each of the links rotates around the RCM, regardless of its position, the links maintain the parallelogram. That is, in a state in which the body 2110 and the base link 2115 are fixed, the position of the RCM will not change no matter where the third link 2140 or the fifth link 2160 is positioned, and the third joint 2173, the fourth joint 2174, the fifth joint 2175, and the RCM maintain the parallelogram.

Meanwhile, in the tenth embodiment of the present disclosure, each of the links, in particular, the second link 2130, the third link 2140, the fourth link 2150, and the fifth link 2160 are arranged side by side without overlapping each other, so that no collision occurs when one link rotates with respect to another link. In addition, the links are formed in such a manner that no one link interferes with the rotation of another link, so that a driving range of each link is increased.

In detail, referring to FIG. 50B, which is a plan view of the surgical robot arm 2100 according to an embodiment of the present disclosure, or the like, when viewed from the XY plane, each of the second link 2130, the third link 2140, the fourth link 2150, and the fifth link 2160 is formed to be offset by a certain degree in a direction of the rotation axes thereof (i.e., the Y-axis direction). In other words, based on the Y-axis direction, the third link 2140 is disposed on one side of the second link 2130, the fourth link 2150 is disposed on one side of the third link 2140, and the fifth link 2160 is disposed on one side of the fourth link 2150. In other words, it may be expressed that the second link 2130, the third link 2140, the fourth link 2150, and the fifth link 2160 are sequentially arranged in the Y-axis direction.

In particular, by disposing the fifth link 2160, on which the surgical instrument 2200 is mounted, to be offset by a certain degree with respect to the fourth link 2150, a restriction on the rotation angle of the fifth link 2160 (and the surgical instrument 2200 coupled thereto) with respect to the fourth link 2150 is eliminated, thereby achieving an effect of allowing the fifth link 2160 (and the surgical instrument 2200 coupled thereto) to rotate freely.

Meanwhile, in the tenth embodiment of the present disclosure, the surgical instrument 2200 coupled to the fifth link 2160 is disposed to face inwardly of the surgical robot arm 2100.

In detail, in the fifth link 2160, a surface on which the instrument mounting part is formed, or, in other words, a surface to which the surgical instrument 2200 is coupled is assumed to be a first surface, and a surface opposite to the surface is assumed to be a second surface.

At this time, in a state in which the end tool 2210 of the surgical instrument 2200 coupled to the fifth link 2160 faces vertically downward, the first surface is disposed in a direction approaching the body 2110 or in a direction facing the body 2110. In other words, the surgical instrument 2200 coupled to the first surface of the fifth link 2160 is disposed closer to the body 2110 than the fifth link 2160.

Meanwhile, in a state in which the surgical instrument 2200 coupled to the fifth link 2160 is horizontally disposed and the end tool 2210 is disposed in a direction away from the body 2110, the first surface is disposed to face downward. In other words, the surgical instrument 2200 coupled to the first surface of the fifth link 2160 is disposed below the fifth link 2160.

With this configuration, even when the modular surgical robot arm 2100 is horizontally positioned in a state of being disposed adjacent to a port of the patient, the fifth link 2160, on which the surgical instrument 2200 is mounted, is prevented from coming into direct contact with a patient, thereby having the advantage of reducing vibration and improving rigidity.

Operations of Surgical Robot Arm

FIGS. 50 to 52 are views illustrating an RCM motion (pitch motion) of the surgical robot arm of FIG. 48 around the pitch axis P, each view including both a side view and a plan view.

As shown in FIGS. 50 to 52, when a motor (not shown) is driven, the third link 2140 rotates around the third joint 2173 with respect to the second link 2130. In addition, in conjunction therewith, the fourth link 2150 rotates with respect to the third link 2140, and the fifth link 2160 rotates with respect to the fourth link 2150. At this time, due to the above-described belt or link structure, the fourth link 2150 and the extension line connecting the third joint 2173 to the RCM maintain a parallel state, and the third link 2140 and the fifth link 2160 maintain a parallel state. In other words, the RCM remains constant even in any state of motion of the surgical robot arm 2100 around the pitch axis P.

Meanwhile, as shown in the plan view of each drawing, the second link 2130, the third link 2140, the fourth link 2150, and the fifth link 2160 may be disposed to be adjacent to each other without overlapping each other in the Y-axis direction.

FIGS. 53 to 55 are perspective views illustrating an RCM motion (yaw motion) of the surgical robot arm of FIG. 48 around the first yaw axis Y1.

As shown in FIGS. 53 to 55, when a motor (not shown) is driven, the first link 2120 of the yaw drive assembly 2105 rotates around the first yaw axis Y1 with respect to the base link 2115. At this time, since the first yaw axis Y1 passes through the RCM, the RCM remains constant no matter what angle the first link 2120 rotates with respect to the base link 2115.

FIG. 56 is a view illustrating a state in which the fifth link 2160 of the surgical robot arm 2100 of FIG. 48 and the surgical instrument 2200 coupled thereto are disposed parallel to each other.

As described above, the surgical robot arm 2100 according to the tenth embodiment of the present disclosure is formed such that the first yaw axis Y1 and the extension line connecting the third joint 2173 to the RCM are different from each other, so that the fifth link 2160 and the surgical instrument 2200 coupled thereto can be disposed in the horizontal direction without inducing a gimbal lock phenomenon.

FIG. 57 is a view illustrating a state in which the surgical robot arm 2100 illustrated in FIG. 56 is disposed near the patient's surgical site, and the surgical instrument 2200 is disposed directly facing the patient.

As described above, in the surgical robot arm 2100 according to the tenth embodiment of the present disclosure, each robot arm is formed in a modular manner, and the fifth link 2160 and the surgical instrument 2200 coupled thereto may be disposed parallel to each other. Accordingly, each modular surgical robot arm 2100 may be disposed near the patient's surgical site, and the surgical instrument 2200 may be disposed directly facing the patient.

FIG. 58 is a view illustrating a state in which the end tool 2210 of the surgical instrument 2200 coupled to the fifth link 2160 of the surgical robot arm 2100 of FIG. 48 is disposed facing upward from below.

As described above, the surgical robot arm 2100 according to the tenth embodiment of the present disclosure is formed such that the first yaw axis Y1 and the extension line connecting the third joint 2173 to the RCM intersect each other at the RCM, so that the surgical instrument 2200 can be disposed facing upward from below, beyond the horizontal direction.

According to the tenth embodiment of the present disclosure described above, by forming the first yaw axis Y1 and the extension line connecting the third joint 2173 to the RCM to be different from each other, the fifth link 2160 and the surgical instrument 2200 coupled thereto can be disposed in the horizontal direction without inducing a gimbal lock phenomenon. Furthermore, the surgical instrument 2200 can be disposed facing upward from below, beyond the horizontal direction.

Further, by disposing each of the links to be offset by a certain degree, the rotational motion of each link is not constrained by another link, so that the range of motion of the instrument is increased, such as the moving direction of the instrument is directed upward beyond the horizontal direction. Accordingly, even in the frequent case of surgery, in which the instrument is disposed in the horizontal direction, an effect of preventing the gimbal lock and allowing the instrument to move with a sufficient range of motion may be obtained.

<Eleventh Embodiment of Surgical Robot Arm>

Hereinafter, a surgical robot arm 2600 according to an eleventh embodiment of the present disclosure will be described. Here, the surgical robot arm 2600 according to the eleventh embodiment of the present disclosure is different from the surgical robot arm (see 2100 in FIG. 48 or the like) according to the tenth embodiment of the present disclosure described above in that a setup link assembly 2690 is further included. Such a configuration that is changed from that of the tenth embodiment will be described in detail below.

Figure 59:
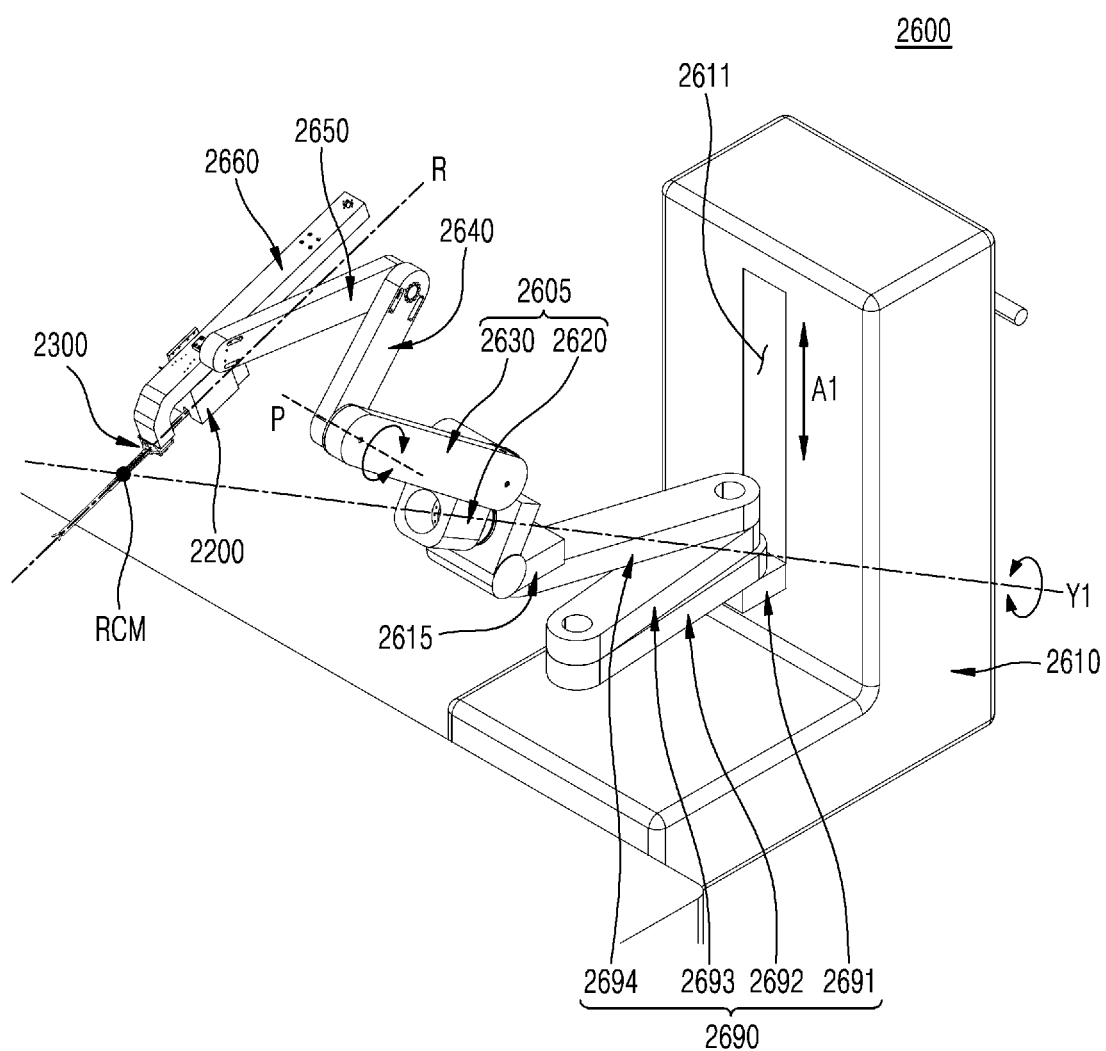
FIG. 59 is a perspective view illustrating a surgical robot arm according to an eleventh embodiment of the present disclosure.

FIG. 59 is a perspective view illustrating the surgical robot arm according to the eleventh embodiment of the present disclosure.

Referring to FIG. 59, the surgical robot arm 2600 according to the eleventh embodiment of the present disclosure includes a body 2610, a base link 2615, a yaw drive assembly 2605, a third link 2640, a fourth link 2650, and a fifth link 2660. Here, the yaw drive assembly 2605 may include a first link 2620 and a second link 2630. Further, the surgical robot arm 2600 according to the eleventh embodiment of the present disclosure further includes the setup link assembly 2690. In addition, as in the tenth embodiment illustrated with reference to FIG. 32, the surgical robot arm 2600 of the present embodiment may include a first joint (sec 2171 in FIG. 50), a second joint (see 2172 in FIG. 50) a third joint (see 2173 in FIG. 50), a fourth joint (see 2174 in FIG. 50), and a fifth joint (see 2175 in FIG. 50). In addition, a trocar 1300 and a surgical instrument 2200 are coupled to the fifth link 2660 of the surgical robot arm 2600 described above.

Here, the body 2610 serves as a base of the entire surgical robot arm 2600.

Meanwhile, the base link 2615 may be formed on one surface of the body 2610, for example, an upper surface thereof. The base link 2615 may be formed to be inclined by a certain degree to have a predetermined angle with respect to a horizontal plane.

Meanwhile, the yaw drive assembly 2605 is rotatably coupled to the base link 2615. The yaw drive assembly 2605 is coupled to the base link 2615 by the first joint (sec 2171 in FIG. 50), and formed to be yaw rotatable around the first yaw axis Y1 with respect to the base link 2615.

Here, the yaw drive assembly 2605 may include the first link 2620 and the second link 2630. The yaw drive assembly 2605 is coupled to the base link 2615 by the first joint (sec 2171 in FIG. 50), and formed to be yaw rotatable around the first yaw axis Y1 with respect to the base link 2615. Here, the first link 2620 is coupled to the base link 2615 by the first joint (see 2171 in FIG. 50), and formed to be yaw rotatable around the first yaw axis Y1 with respect to the base link 2615. In addition, one end portion of the second link 2630 is fixedly coupled to the first link 2620, and another end portion thereof is coupled to the third link 2640 to be described later.

The third link 2640 is axially coupled to the second link 2630 so as to be rotatable around the third joint (see 2173 in FIG. 50) with respect to the second link 2630. Here, the third joint (see 2173 in FIG. 50) may include one or more pulleys.

The fourth link 2650 is axially coupled to the third link 2640 so as to be rotatable around the fourth joint (see 2174 in FIG. 50) with respect to the third link 2640. Here, the fourth joint (see 2174 in FIG. 50) may include one or more pulleys.

The fifth link 2660 is axially coupled to the fourth link 2650 so as to be rotatable around the fifth joint (see 2175 in FIG. 50) with respect to the fourth link 2650. Here, the fifth joint (sec 2175 in FIG. 50) may include one or more pulleys.

The surgical instrument 2200 is coupled to the fifth link 2660.

Here, the third link 2640, the fourth link 2650, and the fifth link 2660 form a parallelogram, and configure a kind of RCM mechanism. That is, when the third link 2640 rotates around the third joint (sec 2173 in FIG. 50) in a state in which the position of the third joint (see 2173 in FIG. 50) is fixed, due to the RCM mechanism of a link/belt described above, the third link 2640 and the fifth link 2660 rotate while maintaining a parallel state, and the fourth link 2650 and an extension line connecting the third joint (sec 2173 in FIG. 50) to an RCM also rotate while maintaining a parallel state. Accordingly, the RCM may remain constant in position regardless of the rotation angle of the third link 2640.

Here, the surgical robot arm 2600 according to the eleventh embodiment of the present disclosure further includes the setup link assembly 2690. That is, the setup and positioning of the surgical robot arm 2600 can be more easily performed by further including the setup link assembly 2690, which is formed between the body 2610 and the base link 2615, connects the body 2610 to the base link 2615, and allows the base link 2615 (and the links connected thereto) to move vertically or horizontally with respect to the body 2610. This will be described in more detail below.

In detail, the setup link assembly 2690 may include a vertical setup link 2691 and one or more horizontal setup links 2692, 2693, and 2694.

The vertical setup link 2691 is connected to the body 2610, and formed to be movable in the Z-axis direction with respect to the body 2610.

Here, a guide groove 2611 is vertically formed in the body 2610, and the vertical setup link 2691 is linearly movable up and down along the guide groove 2611 in the direction of an arrow A.

Meanwhile, the setup link assembly 2690 may include a first horizontal setup link 2692, a second horizontal setup link 2693, and a third horizontal setup link 2694. The first horizontal setup link 2692 is axially coupled to the vertical setup link 2691 so as to be rotatable with respect thereto. The second horizontal setup link 2693 is axially coupled to the first horizontal setup link 2692 so as to be rotatable with respect thereto. One end portion of the third horizontal setup link 2693 is rotatably axially coupled to the second horizontal setup link 2692. In addition, the base link 2615 is formed at another end portion of the third horizontal setup link 2693.

As described above, since the setup link assembly 2690 includes one or more horizontal setup links 2692, 2693, and 2694, the base link 2615 connected to the setup link assembly 2690 may be disposed in various setup positions on the XY plane.

Meanwhile, in the drawing, it is illustrated that the vertical setup link 2691 is connected to the body 2610 and the horizontal setup links 2692, 2693, and 2694 are connected to the vertical setup link 2691, but the concept of the present disclosure is not limited thereto. That is, a configuration in which the horizontal setup links are connected to the body 2610 and the vertical setup link is connected to the horizontal setup links is also possible. Alternatively, a configuration in which only one of the vertical setup link and the horizontal setup link is provided is also possible. Alternatively, various configurations and arrangements of the horizontal setup links and vertical setup link are possible, such as a configuration in which the vertical link is disposed in the middle of a plurality of horizontal setup links.

Here, the setup link assembly 2690 may be formed to be operative only during a period in which the surgical robot arm 2600 is deployed at an appropriate position on one side of a patient before the surgical robot arm 2600 actually begins to perform a surgery, and to remain in a fixed state without moving during a period in which the surgical robot arm 2600 is completely deployed and actually performs a surgery. To this end, although not shown in the drawings, the setup link assembly 2690 may further include a brake module (not shown) capable of maintaining a stationary state, and the brake module may further include a manipulation member (not shown) capable of selecting an activated/deactivated state.

By further including the setup link assembly 2690 as described above, the setup and positioning of the surgical robot arm 2600 can be more easily performed.

<Twelfth Embodiment of Surgical Robot Arm>

Hereinafter, a surgical robot arm 2700 according to a twelfth embodiment of the present disclosure will be described. Here, the surgical robot arm 2700 according to the twelfth embodiment of the present disclosure is different from the surgical robot arm (see 2100 in FIG. 48 or the like) according to the tenth embodiment of the present disclosure described above in that a setup link assembly 2790 is further included. Such a configuration that is changed from that of the tenth embodiment will be described in detail below.

Figure 60:
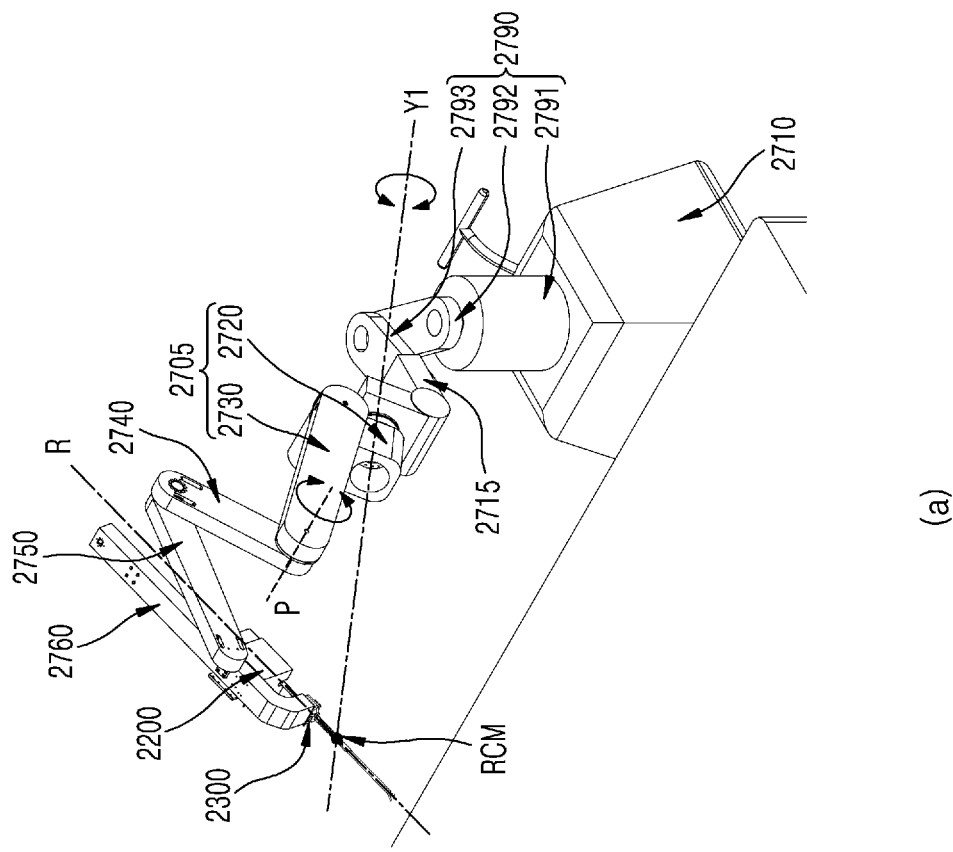
FIG. 60 is a perspective view illustrating a surgical robot arm according to a twelfth embodiment of the present disclosure.
Figure 61:
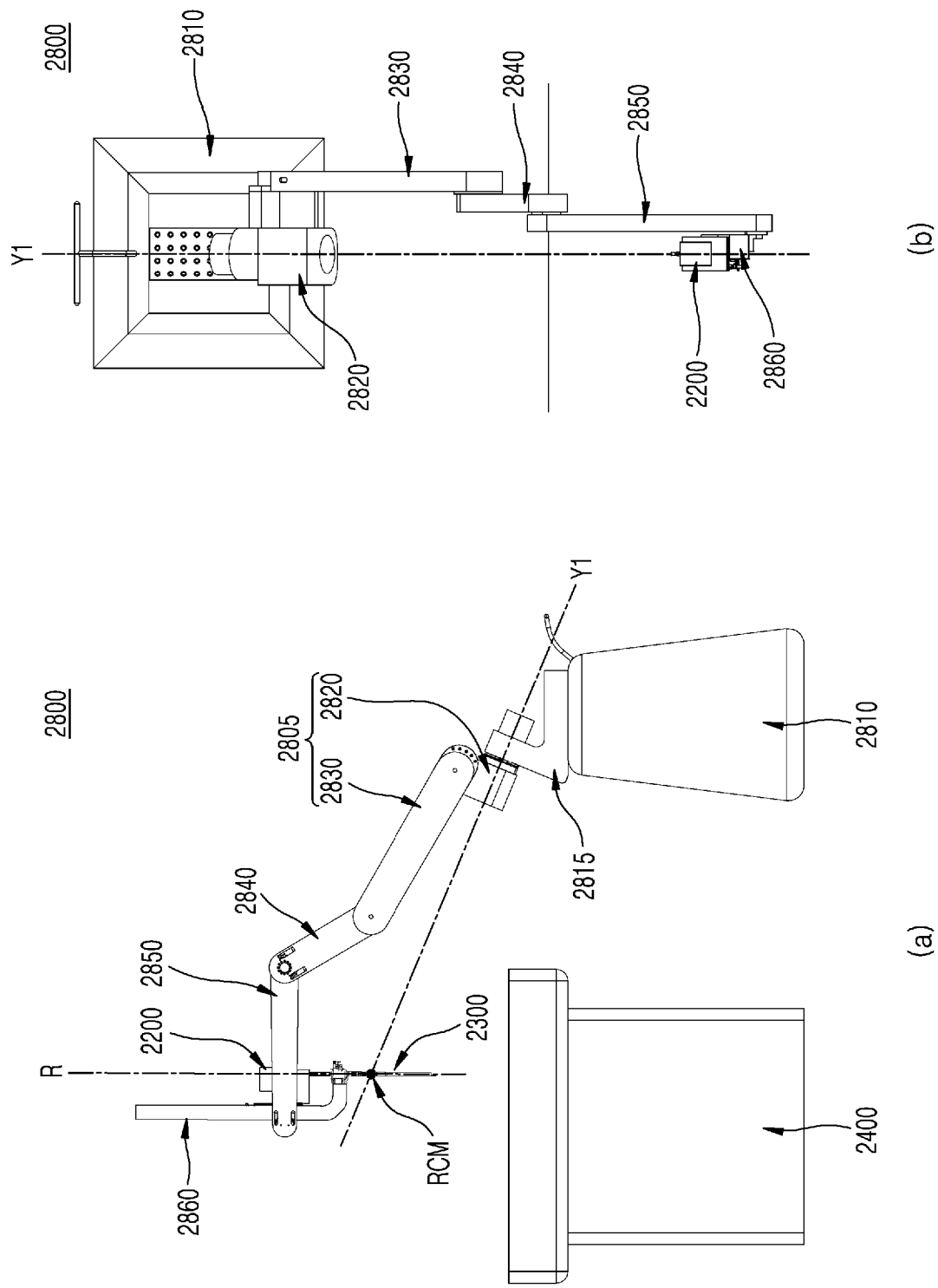
FIG. 61 is a perspective view illustrating a surgical robot arm according to a thirteenth embodiment of the present disclosure.

FIG. 60 is a perspective view illustrating the surgical robot arm according to the twelfth embodiment of the present disclosure.

Referring to FIG. 60, the surgical robot arm 2700 according to the twelfth embodiment of the present disclosure includes a body 2710, a base link 2715, a yaw drive assembly 2705, a third link 2740, a fourth link 2750, and a fifth link 2760. Here, the yaw drive assembly 2705 may include a first link 2720 and a second link 2730. In addition, the surgical robot arm 2700 according to the twelfth embodiment of the present disclosure further includes the setup link assembly 2790. In addition, as in the tenth embodiment illustrated with reference to FIG. 48, the surgical robot arm 2700 of the present embodiment may include a first joint (see 2171 in FIG. 50), a second joint (see 2172 in FIG. 50), a third joint (see 2173 in FIG. 50), a fourth joint (see 2174 in FIG. 50), and a fifth joint (sec 2175 in FIG. 50). In addition, a trocar 2300 and a surgical instrument 2200 are coupled to the fifth link 2760 of the surgical robot arm 2700 described above.

Here, the body 2710 serves as a base of the entire surgical robot arm 2700.

Meanwhile, the base link 2715 may be formed on one surface of the body 2710, for example, an upper surface thereof. The base link 2715 may be formed to be inclined by a certain degree to have a predetermined angle with respect to a horizontal plane.

Meanwhile, the yaw drive assembly 2705 is rotatably coupled to the base link 2715. The yaw drive assembly 2705 is coupled to the base link 2715 by the first joint (see 2171 in FIG. 50), and formed to be yaw rotatable around a first yaw axis Y1 with respect to the base link 2715.

Here, the yaw drive assembly 2705 may include the first link 2720 and the second link 2730. The yaw drive assembly 2705 is coupled to the base link 2715 by the first joint (see 2171 in FIG. 50), and formed to be yaw rotatable around a first yaw axis Y1 with respect to the base link 2715. Here, the first link 2720 is coupled to the base link 2715 by the first joint (see 2171 in FIG. 50), and formed to be yaw rotatable around the first yaw axis Y1 with respect to the base link 2715. In addition, one end portion of the second link 2730 is fixedly coupled to the first link 2720, and another end portion thereof is coupled to the third link 2740 to be described later.

The third link 2740 is axially coupled to the second link 2730 so as to be rotatable around the third joint (see 2173 in FIG. 50) with respect to the second link 2730. Here, the third joint (see 2173 in FIG. 50) may include one or more pulleys.

The fourth link 2750 is axially coupled to the third link 2740 so as to be rotatable around the fourth joint (see 2174 in FIG. 50) with respect to the third link 2740. Here, the fourth joint (see 2174 in FIG. 50) may include one or more pulleys.

The fifth link 2760 is axially coupled to the fourth link 2750 so as to be rotatable around the fifth joint (see 2175 in FIG. 50) with respect to the fourth link 2750. Here, the fifth joint (sec 2175 in FIG. 50) may include one or more pulleys.

The surgical instrument 2200 is coupled to the fifth link 2760.

In this case, the third link 2740, the fourth link 2750, and the fifth link 2760 form a parallelogram, and configure a kind of RCM mechanism. That is, when the third link 2740 rotates around the third joint (see 2173 in FIG. 50) in a state in which the position of the third joint (see 2173 in FIG. 50) is fixed, due to the RCM mechanism of a link/belt described above, the third link 2740 and the fifth link 2760 rotate while maintaining a parallel state, and the fourth link 2750 and an extension line connecting the third joint (see 2173 in FIG. 50) to an RCM also rotate while maintaining a parallel state. Accordingly, the RCM may remain constant in position regardless of the rotation angle of the third link 2740.

Here, the surgical robot arm 2700 according to the twelfth embodiment of the present disclosure further includes the setup link assembly 2790. That is, the setup and positioning of the surgical robot arm 2700 can be more easily performed by further including the setup link assembly 2790, which is formed between the body 2710 and the base link 2715, connects the body 2710 to the base link 2715, and allows the base link 2715 (and the links connected thereto) to move vertically or horizontally with respect to the body 2710. This will be described in more detail below.

In detail, the setup link assembly 2790 may include a vertical setup link 2791 and one or more horizontal setup links 2792 and 2793.

The vertical setup link 2791 is connected to the body 2710, and formed to be movable in the Z-axis direction with respect to the body 2710.

Here, the vertical setup link 2791 is formed in a cylindrical shape, and thus, linearly movable up and down while being drawn in or out from the body 2710 in the direction of an arrow B.

Meanwhile, the setup link assembly 2790 may include a first horizontal setup link 2792 and a second horizontal setup link 2793. The first horizontal setup link 2792 is axially coupled to the vertical setup link 2791 so as to be rotatable with respect thereto. The second horizontal setup link 2793 is axially coupled to the first horizontal setup link 2792 so as to be rotatable with respect thereto. In addition, the base link 2715 is formed at another end portion of the second horizontal setup link 2792.

As described above, since the setup link assembly 2790 includes one or more horizontal setup links 2792 and 2793, the base link 2715 connected to the setup link assembly 2790 may be disposed in various setup positions on the XY plane.

Meanwhile, in the drawing, it is illustrated that the vertical setup link 2791 is connected to the body 2710 and the horizontal setup links 2792 and 2793 are connected to the vertical setup link 2791, but the concept of the present disclosure is not limited thereto. That is, a configuration in which the horizontal setup links are connected to the body 2710 and the vertical setup link is connected to the horizontal setup links is also possible. Alternatively, a configuration in which only one of the vertical setup link and the horizontal setup link is provided is also possible. Alternatively, various configurations and arrangements of the horizontal setup links and vertical link are possible, such as a configuration in which the vertical setup link is disposed in the middle of a plurality of horizontal setup links.

Here, the setup link assembly 2790 may be formed to be operative only during a period in which the surgical robot arm 2700 is deployed at an appropriate position on one side of a patient before the surgical robot arm 2700 actually begins to perform a surgery, and to remain in a fixed state without moving during a period in which the surgical robot arm 2700 is completely deployed and actually performs a surgery. To this end, although not shown in the drawings, the setup link assembly 2790 may further include a brake module (not shown) capable of maintaining a stationary state, and the brake module may further include a manipulation member (not shown) capable of selecting an activated/deactivated state.

By further including the setup link assembly 2790 as described above, the setup and positioning of the surgical robot arm 2700 can be more easily performed.

<Thirteenth Embodiment of Surgical Robot Arm>

Hereinafter, a surgical robot arm 2800 according to a thirteenth embodiment of the present disclosure will be described. Here, the surgical robot arm 2800 according to the thirteenth embodiment of the present disclosure is different from the surgical robot arm (see 2100 in FIG. 48 or the like) according to the tenth embodiment of the present disclosure described above in that a first yaw axis Y1 is formed parallel to links. Such a configuration that is changed from that of the tenth embodiment will be described in detail below.

Figure 62:
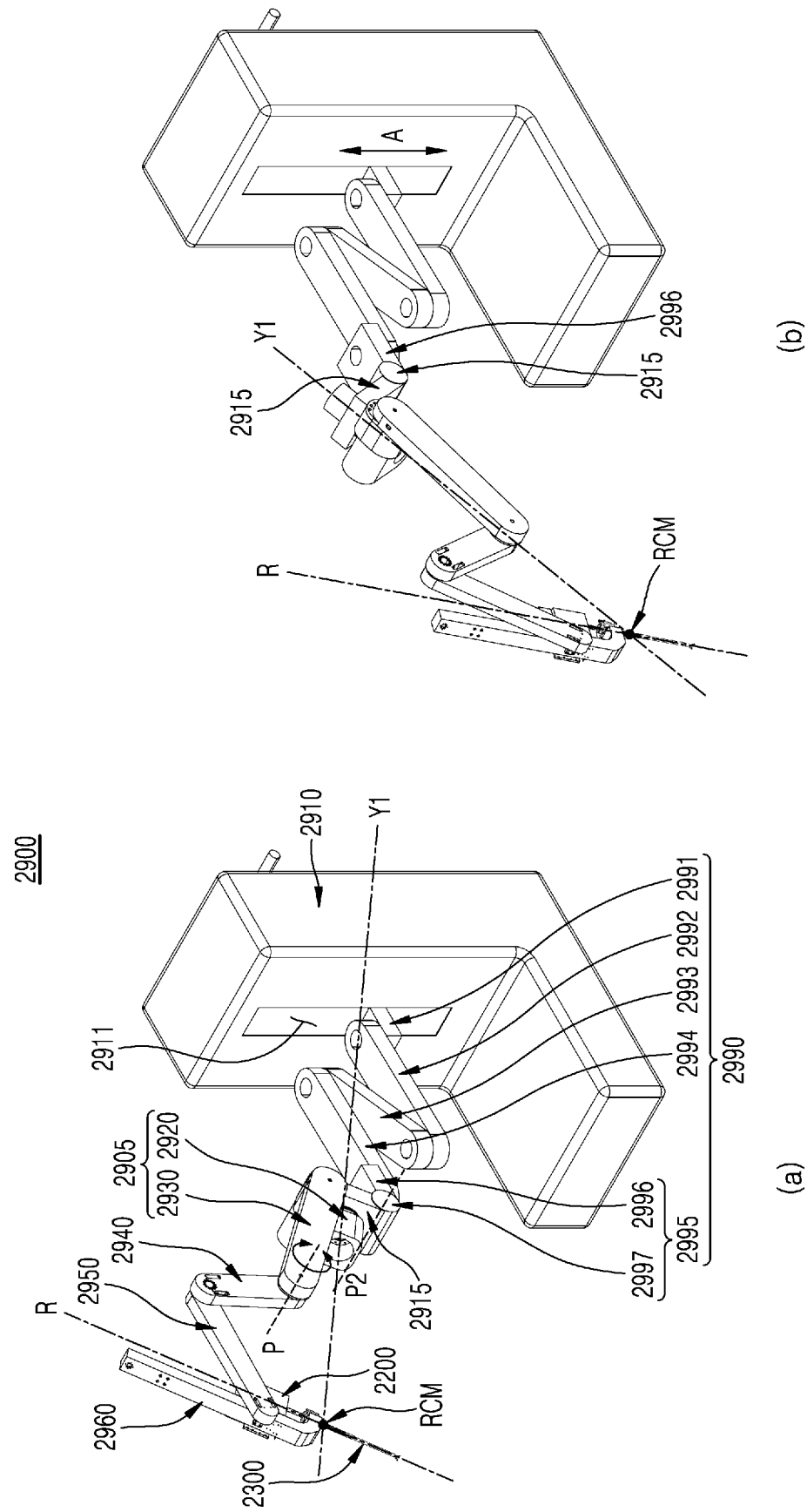
FIG. 62 is a perspective view illustrating a surgical robot arm according to a fourteenth embodiment of the present disclosure.

FIG. 62 is a perspective view illustrating the surgical robot arm according to the thirteenth embodiment of the present disclosure.

Referring to FIG. 62, the surgical robot arm 2800 according to the thirteenth embodiment of the present disclosure includes a body 2810, a base link 2815, a yaw drive assembly 2805, a third link 2840, a fourth link 2850, and a fifth link 2860. Here, the yaw drive assembly 2805 may include a first link 2820 and a second link 2830. In addition, the surgical robot arm 2800 according to the thirteenth embodiment of the present disclosure further includes a setup link assembly 2890. In addition, as in the tenth embodiment illustrated with reference to FIG. 48, the surgical robot arm 2800 of the present embodiment may include a first joint (sec 2171 in FIG. 50), a second joint (sec 2172 in FIG. 50), a third joint (see 2173 in FIG. 50), a fourth joint (see 2174 in FIG. 50), and a fifth joint (see 2175 in FIG. 50). In addition, a trocar 2300 and a surgical instrument 2200 are coupled to the fifth link 2860 of the surgical robot arm 2800 described above.

Here, the body 2810 serves as a base of the entire surgical robot arm 2800.

Meanwhile, the base link 2815 may be formed on one surface of the body 2810, for example, an upper surface thereof. The base link 2815 may be formed to be inclined by a certain degree to have a predetermined angle with respect to a horizontal plane.

Meanwhile, the yaw drive assembly 2805 is rotatably coupled to the base link 2815. The yaw drive assembly 2805 is coupled to the base link 2815 by the first joint (sec 2171 in FIG. 50), and formed to be yaw rotatable around the first yaw axis Y1 with respect to the base link 2815.

Here, the yaw drive assembly 2805 may include the first link 2820 and the second link 2830. The yaw drive assembly 2805 is coupled to the base link 2815 by the first joint (sec 2171 in FIG. 50), and formed to be yaw rotatable around the first yaw axis Y1 with respect to the base link 2815. Here, the first link 2820 is coupled to the base link 2815 by the first joint (sec 2171 in FIG. 50), and formed to be yaw rotatable around the first yaw axis Y1 with respect to the base link 2815. In addition, one end portion of the second link 2830 is fixedly coupled to the first link 2820, and another end portion thereof is coupled to the third link 2840 to be described later.

The third link 2840 is axially coupled to the second link 2830 so as to be rotatable around the third joint (see 2173 in FIG. 50) with respect to the second link 2830. Here, the third joint (see 2173 in FIG. 50) may include one or more pulleys.

The fourth link 2850 is axially coupled to the third link 2840 so as to be rotatable around the fourth joint (see 2174 in FIG. 50) with respect to the third link 2840. Here, the fourth joint (see 2174 in FIG. 50) may include one or more pulleys.

The fifth link 2860 is axially coupled to the fourth link 2850 so as to be rotatable around the fifth joint (see 2175 in FIG. 50) with respect to the fourth link 2850. Here, the fifth joint (see 2175 in FIG. 50) may include one or more pulleys.

The surgical instrument 2200 is coupled to the fifth link 2860.

In this case, the third link 2840, the fourth link 2850, and the fifth link 2860 form a parallelogram, and configure a kind of RCM mechanism. That is, when the third link 2840 rotates around the third joint (sec 2173 in FIG. 50) in a state in which the position of the third joint (see 2173 in FIG. 50) is fixed, due to the RCM mechanism of a link/belt described above, the third link 2840 and the fifth link 2860 rotate while maintaining a parallel state, and the fourth link 2850 and an extension line connecting the third joint (see 2173 in FIG. 50) to an RCM also rotate while maintaining a parallel state. Accordingly, the RCM may remain constant in position regardless of the rotation angle of the third link 2840.

Here, in the surgical robot arm 2800 according to the thirteenth embodiment of the present disclosure, the first yaw axis Y1 is formed parallel to the links.

In detail, in the case of the tenth embodiment illustrated with reference to FIGS. 50 to 52 and the like, the first yaw axis Y1 is formed not parallel to the links (i.e., the base link 2815, the first link 2820, the second link 2830, the third link 2840, the fourth link 2850, and the fifth link 2860), but formed to form a predetermined angle with at least some of the links.

In contrast, in the surgical robot arm 2800 according to the thirteenth embodiment of the present disclosure, the first yaw axis Y1 is formed parallel to at least some of the base link 2815, first link 2820, second link 2830, third link 2840, fourth link 2850, and fifth link 2860 when viewed from the XY plane.

By forming the first yaw axis Y1 parallel to at least some of the links as described above, the surgical robot arm 2800 can be disposed in a more compact manner.

<Fourteenth Embodiment of Surgical Robot Arm>

Hereinafter, a surgical robot arm 2900 according to a fourteenth embodiment of the present disclosure will be described. Here, the surgical robot arm 2900 according to the fourteenth embodiment of the present disclosure is different from the surgical robot arm (sec 2100 in FIG. 48 or the like) according to the tenth embodiment of the present disclosure described above in that a setup link assembly 2990 is further included. Such a configuration that is changed from that of the tenth embodiment will be described in detail below.

Figure 63:
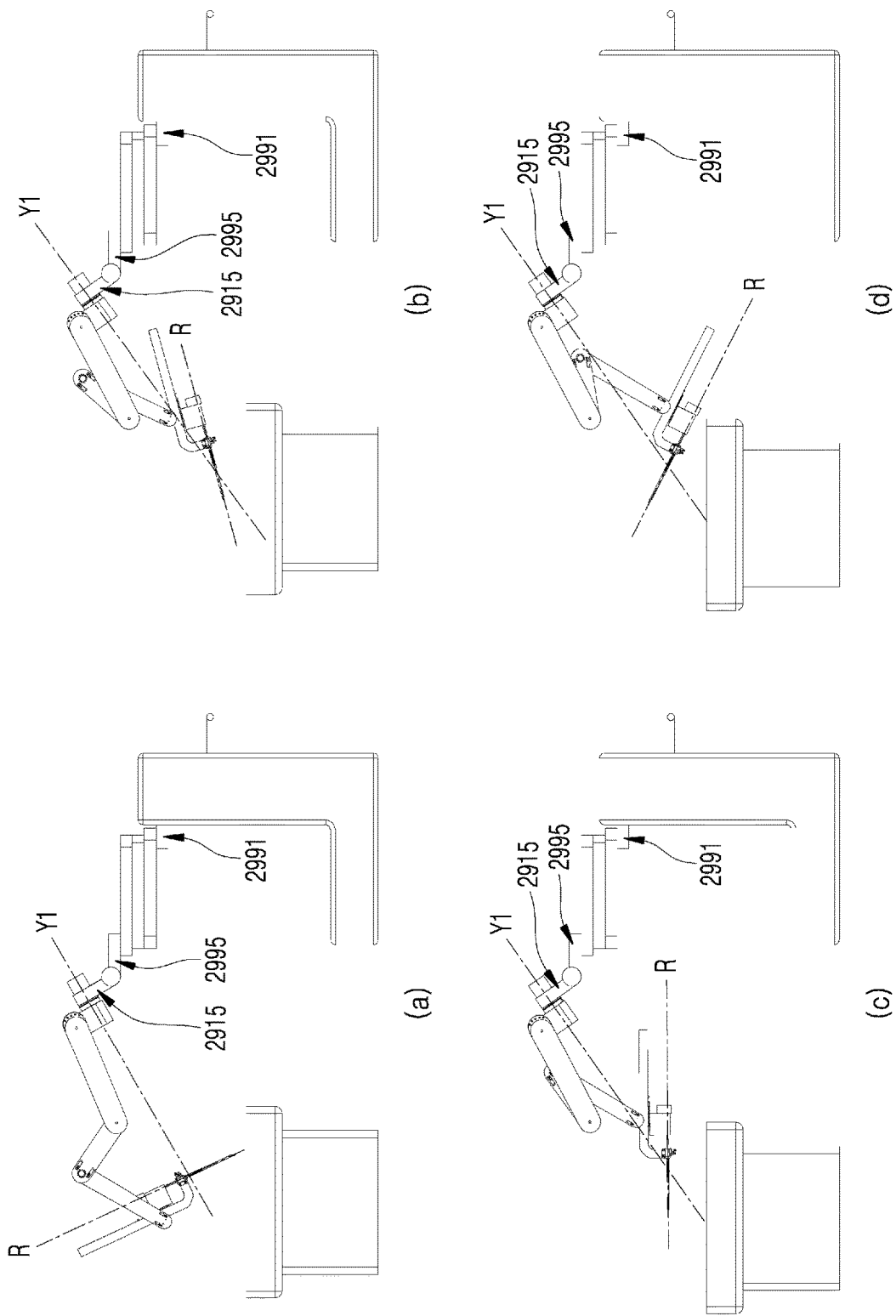
FIG. 63 is a side view illustrating various motion states of the surgical robot arm of FIG. 62.

FIG. 62 is a perspective view illustrating the surgical robot arm according to the fourteenth embodiment of the present disclosure, and FIG. 63 is a side view illustrating various motion states of the surgical robot arm of FIG. 62.

Referring to FIGS. 62 and 63, the surgical robot arm 2900 according to the fourteenth embodiment of the present disclosure includes a body 2910, a base link 2915, a yaw drive assembly 2905, a third link 2940, a fourth link 2950, and a fifth link 2960. Here, the yaw drive assembly 2905 may include a first link 2920 and a second link 2930. In addition, the surgical robot arm 2900 according to the fourteenth embodiment of the present disclosure further includes the setup link assembly 2990. In addition, as in the tenth embodiment illustrated with reference to FIG. 48, the surgical robot arm 2900 of the present embodiment may include a first joint (see 2171 in FIG. 50), a second joint (see 2172 in FIG. 50), a third joint (see 2173 in FIG. 50), a fourth joint (see 2174 in FIG. 50), and a fifth joint (see 2175 in FIG. 50). In addition, a trocar 2300 and a surgical instrument 2200 are coupled to the fifth link 2960 of the surgical robot arm 2900 described above.

Here, the body 2910 serves as a base of the entire surgical robot arm 2900.

Meanwhile, the base link 2915 may be formed on one surface of the body 2910, for example, an upper surface thereof. The base link 2915 may be formed to be inclined by a certain degree to have a predetermined angle with respect to a horizontal plane.

Meanwhile, the yaw drive assembly 2905 is rotatably coupled to the base link 2915. The yaw drive assembly 2905 is coupled to the base link 2915 by the first joint (see 2171 in FIG. 50), and formed to be yaw rotatable around the first yaw axis Y1 with respect to the base link 2915.

Here, the yaw drive assembly 2905 may include the first link 2920 and the second link 2930. The yaw drive assembly 2905 is coupled to the base link 2915 by the first joint (see 2171 in FIG. 50), and formed to be yaw rotatable around the first yaw axis Y1 with respect to the base link 2915. Here, the first link 2920 is coupled to the base link 2915 by the first joint (see 2171 in FIG. 50), and formed to be yaw rotatable around the first yaw axis Y1 with respect to the base link 2915. In addition, one end portion of the second link 2930 is fixedly coupled to the first link 2920, and another end portion thereof is coupled to the third link 2940 to be described later.

The third link 2940 is axially coupled to the second link 2930 so as to be rotatable around the third joint (see 2173 in FIG. 50) with respect to the second link 2930. Here, the third joint (see 2173 in FIG. 50) may include one or more pulleys.

The fourth link 2950 is axially coupled to the third link 2940 so as to be rotatable around the fourth joint (see 2174 in FIG. 50) with respect to the third link 2940. Here, the fourth joint (see 2174 in FIG. 50) may include one or more pulleys.

The fifth link 2960 is axially coupled to the fourth link 2950 so as to be rotatable around the fifth joint (see 2175 in FIG. 50) with respect to the fourth link 2950. Here, the fifth joint (see 2175 in FIG. 50) may include one or more pulleys.

The surgical instrument 2200 is coupled to the fifth link 2960.

In this case, the third link 2940, the fourth link 2950, and the fifth link 2960 form a parallelogram, and configure a kind of RCM mechanism. That is, when the third link 2940 rotates around the third joint (see 2173 in FIG. 50) in a state in which the position of the third joint (see 2173 in FIG. 50) is fixed, due to the RCM mechanism of a link/belt described above, the third link 2940 and the fifth link 2960 rotate while maintaining a parallel state, and the fourth link 2950 and an extension line connecting the third joint (see 2173 in FIG. 50) to an RCM also rotate while maintaining a parallel state. Accordingly, the RCM may remain constant in position regardless of the rotation angle of the third link 2940.

Here, the surgical robot arm 2900 according to the fourteenth embodiment of the present disclosure further includes the setup link assembly 2990. That is, the setup and positioning of the surgical robot arm 2900 can be more easily performed by further including the setup link assembly 2990, which is formed between the body 2910 and the base link 2915, connects the body 2910 to the base link 2915, and allows the base link 2915 (and the links connected thereto) to move vertically or horizontally with respect to the body 2910. This will be described in more detail below.

In detail, the setup link assembly 2990 may include a vertical setup link 2991 and one or more horizontal setup links 2992, 2993, and 2994.

The vertical setup link 2991 is connected to the body 2910, and formed to be movable in the Z-axis direction with respect to the body 2910.

Here, a guide groove 2911 is vertically formed in the body 2910, and the vertical setup link 2991 is linearly movable up and down along the guide groove 2911 in the direction of an arrow A.

Meanwhile, the setup link assembly 2990 may include a first horizontal setup link 2992, a second horizontal setup link 2993, and a third horizontal setup link 2994. The first horizontal setup link 2992 is axially coupled to the vertical setup link 2991 so as to be rotatable with respect thereto. The second horizontal setup link 2993 is axially coupled to the first horizontal setup link 2992 so as to be rotatable with respect thereto. One end portion of the third horizontal setup link 2993 is rotatably axially coupled to the second horizontal setup link 2992. In addition, a pitch positioning joint 2995, which will be described later, and the base link 2915 connected thereto are formed at another end portion of the third horizontal setup link 2993. Here, a rotation axis of each of the one or more horizontal setup links 2992, 2993, and 2994 may be parallel to the Z-axis. That is, the one or more horizontal setup links 2992, 2993, and 2994 may rotate on the XY plane.

As described above, since the setup link assembly 2990 includes one or more horizontal setup links 2992, 2993, and 2994, the base link 2915 connected to the setup link assembly 2990 may be disposed in various setup positions on the XY plane.

Meanwhile, the setup link assembly 2990 may further include the pitch positioning joint 2995. In addition, the pitch positioning joint 2995 may further include a pitch positioning base 2996 and a pitch positioning shaft 2997. The pitch positioning base 2996 is coupled to one end portion of the third horizontal setup link 2994. In addition, the pitch positioning base 2996 and the base link 2915 may be coupled by the pitch positioning shaft 2997 so as to be rotatable around a second pitch axis P2. Here, the pitch positioning shaft 2997 or the second pitch axis P2 may be substantially parallel to a pitch axis P or a rotation axis of the third joint (see 173 in FIG. 4).

That is, as shown in FIGS. 62 and 63, as the base link 2915 rotates around the pitch positioning shaft 2997 with respect to the pitch positioning base 2996, additional setup adjustments along the direction of the second pitch axis P2 could also be made.

As described above, since the setup link assembly 2990 includes the pitch positioning joint 2995, the base link 2915 connected to the setup link assembly 2990 may be disposed in various setup positions on the XZ plane.

Meanwhile, in the drawing, it is illustrated that the vertical setup link 2991 is connected to the body 2910 and the horizontal setup links 2992, 2993, and 2994 are connected to the vertical setup link 2991, but the concept of the present disclosure is not limited thereto. That is, a configuration in which the horizontal setup links are connected to the body 2910 and the vertical setup link is connected to the horizontal setup links is also possible. Alternatively, a configuration in which only one of the vertical setup link and the horizontal setup link is provided is also possible. Alternatively, various configurations and arrangements of the horizontal setup links and vertical setup link are possible, such as a configuration in which the vertical link is disposed in the middle of a plurality of horizontal setup links.

Here, the setup link assembly 2990 may be formed to be operative only during a setup period in which the surgical robot arm 2900 is deployed at an appropriate position on one side of a patient before the surgical robot arm 2900 actually begins to perform a surgery, and to remain in a fixed state without moving during a period in which the surgical robot arm 2900 is completely deployed and actually performs a surgery. To this end, although not shown in the drawings, the setup link assembly 2990 may further include a brake module (not shown) capable of maintaining a stationary state, and the brake module may further include a manipulation member (not shown) capable of selecting an activated/deactivated state.

As a result, as shown in FIG. 63, as the surgical robot arm 2900 according to the fourteenth embodiment of the present disclosure further includes the setup link assembly 2990 including the vertical setup link 2991, one or more horizontal setup links 2992, 2993, and 2994, and the pitch positioning joint 2995, the surgical robot arm 2900 can be set up in various positions and angles, and setting up and positioning becomes easier.

<Surgical Method Using Surgical Robot>

Hereinafter, a surgical method using a surgical robot including the surgical robot arm according to embodiments of the present disclosure will be described.

Here, a position through which a trocar is inserted and the surgical instrument passes is referred to as a port.

Figure 64:
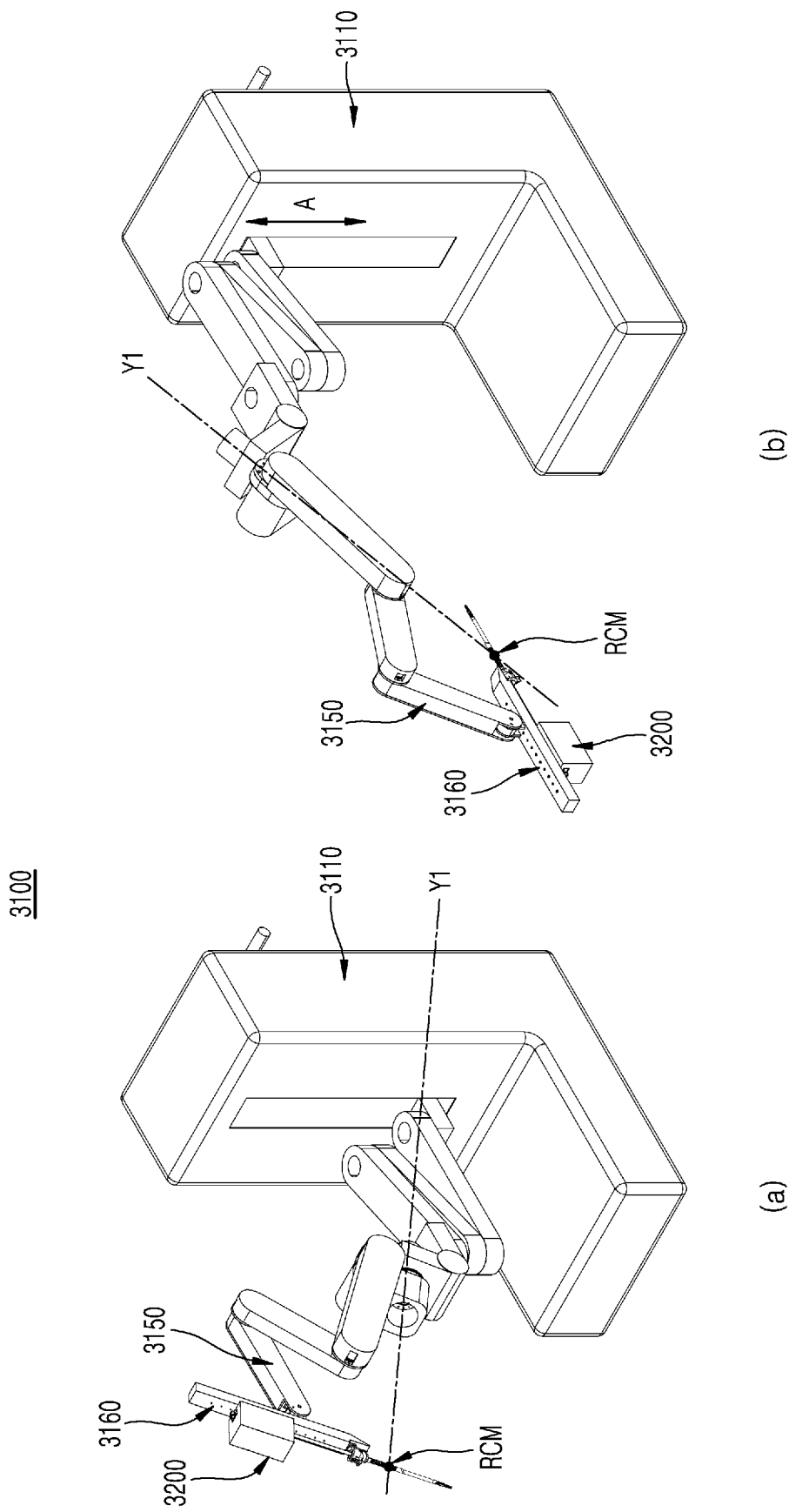
FIGS. 64 to 66 are views illustrating the surgical robot arm.

A surgical robot arm 3100 illustrated in FIG. 64 has a structure, in which a surgical instrument 3200 is facing upward (outward) in a stationary position, and a fifth link 3160, on which the surgical instrument 3200 is mounted and a fourth link 3150 connected thereto are formed on the same plane and will not overlap each other.

Accordingly, in the case of a surgery in which the surgical instrument 3200 is to be inserted in a direction that is horizontal to a plane of an operating table on which a patient is lying, in order to prevent the fifth link 3160, on which the surgical instrument 3200 is mounted, from coming into direct contact with the patient, as shown in FIG. 64B, a body 3110 should be positioned across from a patient's surgical site (i.e., port), links of the surgical robot arm 3100 should be deployed to extend away from the body 3110 as if covering an upper portion of the patient's body, and the surgical instrument 3200 should be disposed in an opposite direction so as to face again toward the patient. Accordingly, disadvantages such as increased vibration and reduced rigidity may occur due to the shape of the surgical robot arm 3100 extending away from the body 3110, which is a support thereof.

Figure 65:
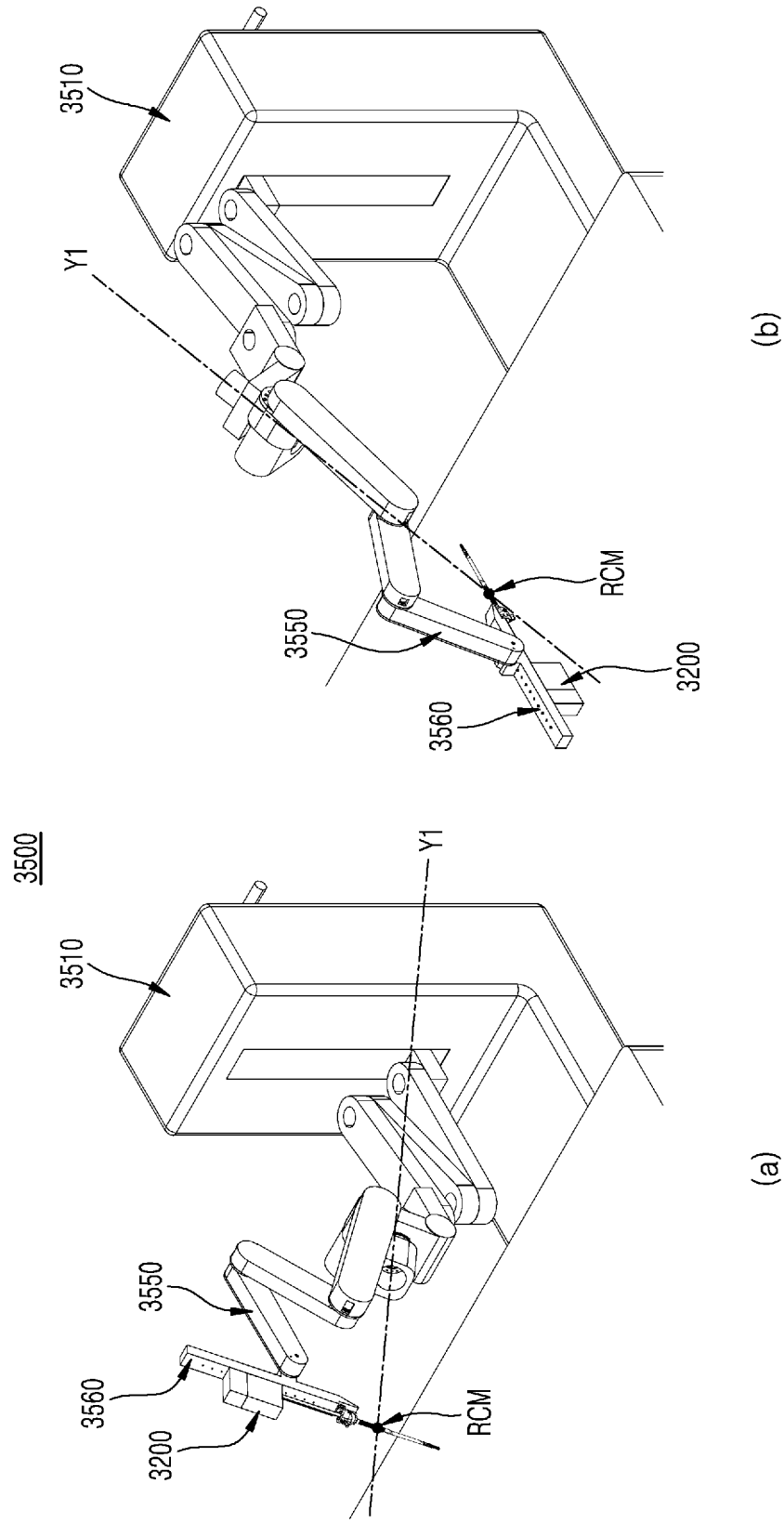

Meanwhile, a surgical robot arm 3500 illustrated in FIGS. 65 and 66 also has a structure in which the surgical instrument 3200 is facing upward (outward) in a stationary position.

Even in this case, as in the case of FIG. 64, in order to prevent a fifth link 3260, on which the surgical instrument 3200 is mounted, from coming into direct contact with the patient, a body 3510 should be positioned across from a patient's surgical site (i.e., port), links of the surgical robot arm 3500 should be deployed to extend away from the body 3510 as if covering an upper portion of the patient's body, and the surgical instrument 3200 should be disposed in an opposite direction so as to face again toward the patient. Accordingly, disadvantages such as increased vibration and reduced rigidity may occur due to the shape of the surgical robot arm 3500 extending away from the body 3510, which is a support thereof.

Figure 67:
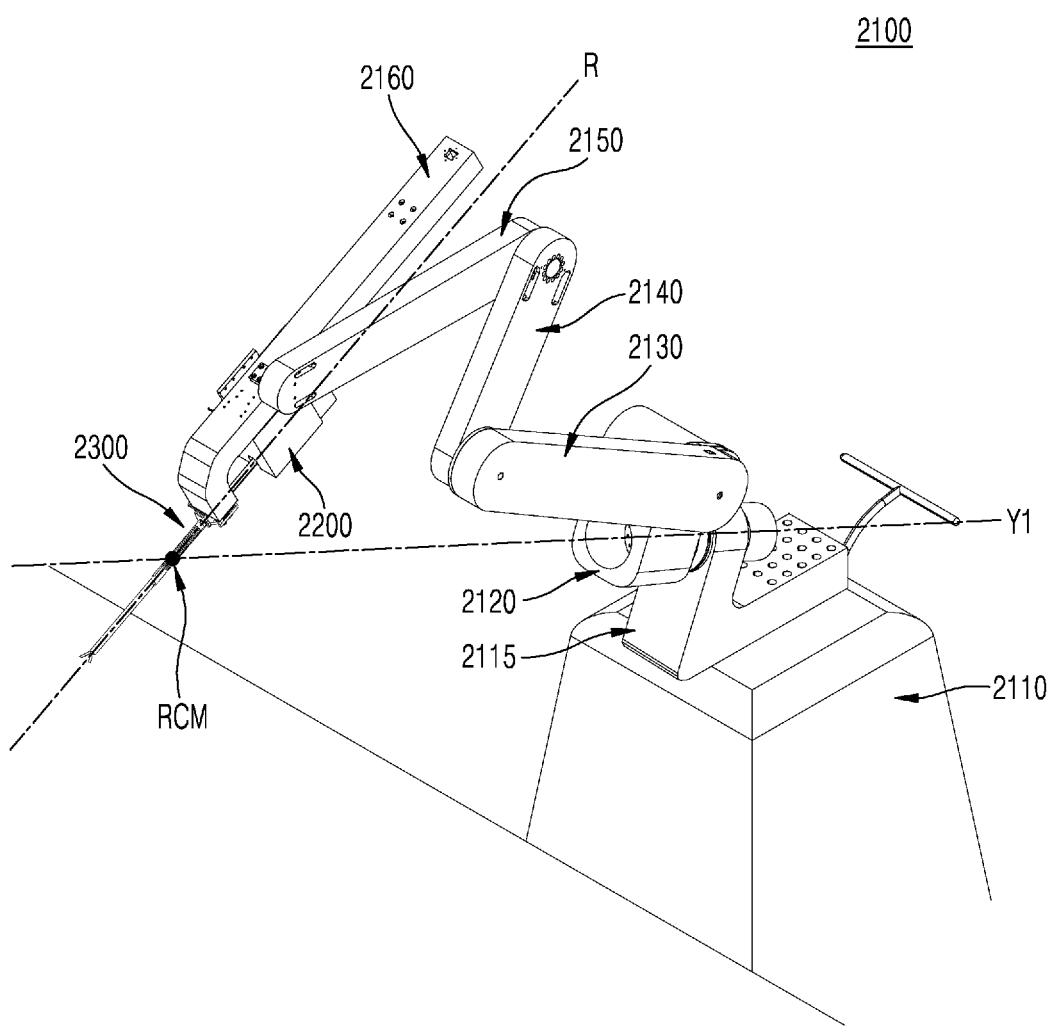
FIG. 67 is a view illustrating a surgical robot arm that implements a surgical method of the present disclosure.

In contrast, the surgical robot arm 2100 according to the tenth embodiment of the present disclosure illustrated in FIG. 67 has a structure in which the surgical instrument 2200 is facing downward (inward), which is an inverted position, and the fifth link 2160 and the fourth link 2150 are formed on different planes so as to overlap each other.

Thus, in the case of a surgery in which the surgical instrument 2200 is to be inserted in a direction that is horizontal to a plane of an operating table on which a patient is lying, the modular surgical robot arm 2100 has a structure in which the fifth link 2160, on which the surgical instrument 3200 is mounted, is prevented from coming into direct contact with the patient even when the surgical robot arm 2100 is positioned horizontally in a state of being disposed adjacent to the patient's port.

Figure 68:
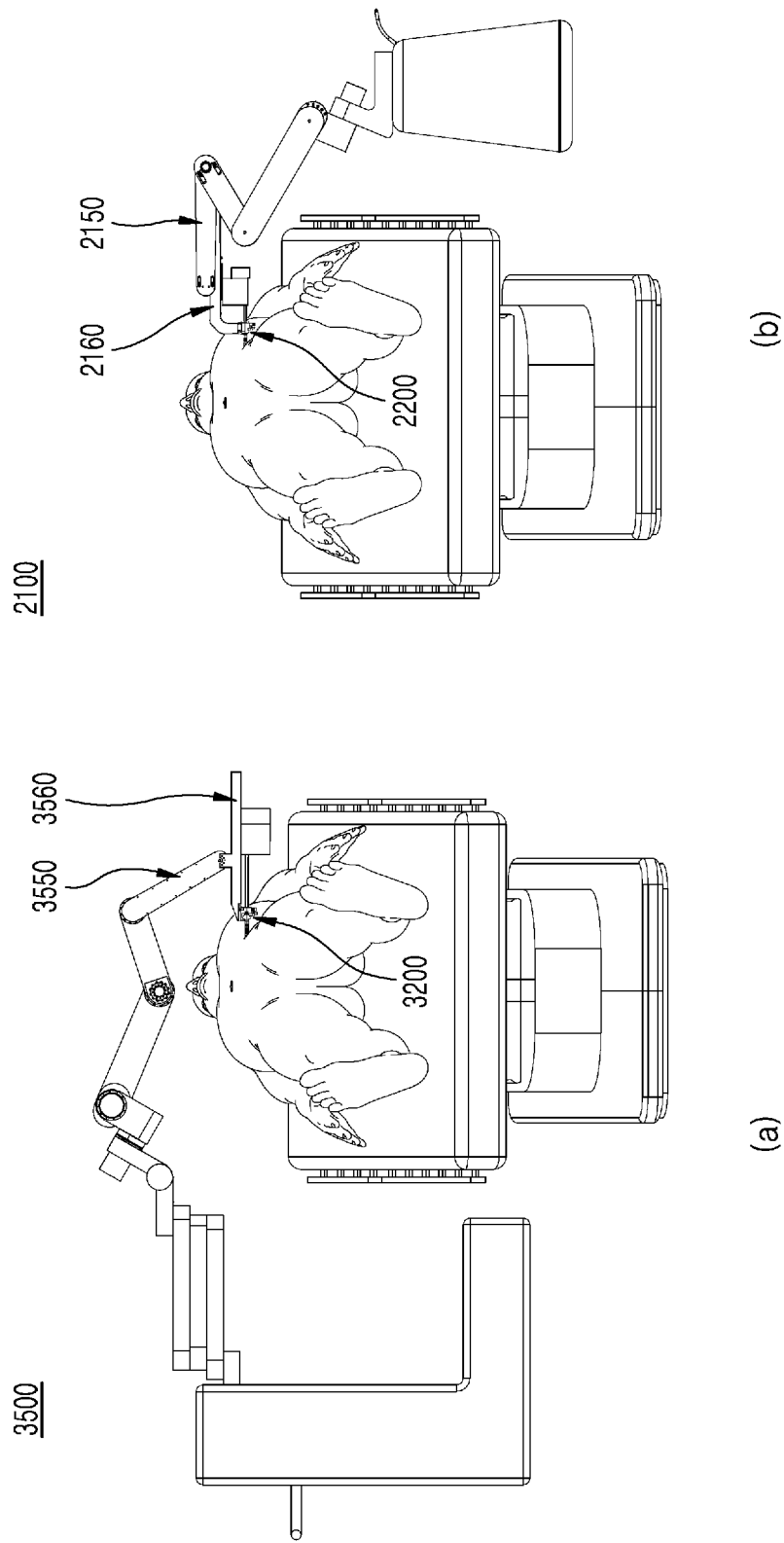
FIG. 68 is a view comparing a surgical operation using the surgical robot arm of FIG. 65 and a surgical operation using the surgical robot arm of FIG. 67.

That is, in the case of the surgical robot arm 3500 illustrated in FIGS. 66 and 68A, in order for the surgical instrument 3200 to be inserted in a direction that is horizontal to the plane of the operating table on which the patient is lying, the surgical robot arm 3100 should have to be disposed in such a shape that extends away from the body 3110 that is a support thereof, which could result in increased vibration and reduced rigidity. On the other hand, in the case of the surgical robot arm 3500 illustrated in FIGS. 67 and 68B, even when the modular surgical robot arm 2100 is positioned horizontally is a state of being disposed adjacent to the patient's port, the fifth link 2160, on which the surgical instrument 3200 is mounted, is prevented from coming into direct contact with the patient, thereby having the advantage of reducing vibration and improving rigidity.

Hereinafter, a surgical method using the surgical robot arm 2100 according to the tenth embodiment or the like of the present disclosure described above will be described in detail.

As described above, in the previous embodiments, in the case of a surgery in which the instrument should be inserted in a direction that is horizontal to the plane of the operating table on which the patient is lying, the base (cart) should be positioned across from a patient's surgical site, the robot arm should be deployed while extending so as to face toward the patient again, and the instrument should be disposed in a direction opposite to a direction, in which the robot arm extends, to face the patient. Thus, this may result in a disadvantage such as deploying one or more robot arms above the patient, along with other drawbacks like an increase in vibration and a reduction in rigidity occurring due to the way the surgical robot arm extends away from its support, i.e., the tower.

In order to address such a problem, the surgical robot arm 2100 according to the tenth embodiment or the like of the present disclosure may be configured to ensure that the rotational motion of one link is not constrained by another link by 1) forming each surgical robot arm 2100 in a modular manner, 2) forming the first yaw axis Y1 and the extension line connecting the third joint 2173 to the RCM to be different from each other, such that the extension line and the first yaw axis Y1 intersect each other at the RCM, and 3) arranging the links side by side (when viewed from the XZ plane) to be adjacent to each other so that the links overlap, thereby increasing the range of motion of the instrument. 4) Furthermore, the surgical robot arm 2100 may be configured such that when the surgical instrument 2200 is mounted on the fifth link 2160, the surgical instrument 2200 is positioned at the bottom of the fifth link 2160 rather than at the top thereof (i.e., positioned in a direction in which the links are positioned when all links are folded). That is, it may be said that the surgical instrument 2200 is in an upside-down state as compared to the related art.

With this configuration of the present disclosure, even in the case of a surgery in which the surgical instrument 2200 should be inserted in a direction that is horizontal to the plane of the operating table on which the patient is lying, the fifth link 2160, on which the surgical instrument 2200 is mounted, is prevented from coming into direct contact with the patient even when the body 2110 of the surgical robot arm 2100 is positioned at a position near the patient's port (the position through which the trocar is inserted), that is, on a side through which the surgical instrument 2200 is to be inserted, and the surgical instrument 2200 is inserted horizontally into the patient's port (trocar) from the position. In addition, this may facilitate the design and implementation of the surgical robot arm 2200 and further increase the range of motion of the surgical instrument 2200.

A surgical method using the above-described surgical robot arm of the present disclosure may include arranging the body of the modular surgical robot arm 2100 on one side of a patient's port through which the surgical instrument 2200 is to be inserted, arranging the fifth link 2150, on which the surgical instrument 2200 is mounted, to be a substantially horizontal state in the surgical robot arm 2100, mounting the surgical instrument 2200 on the fifth link 2150 of the surgical robot arm 2100, inserting the surgical instrument 2200 into the patient's body by moving the surgical instrument 2200 mounted on the surgical robot arm 2100, performing a surgery by the surgical instrument 2200 while maintaining an RCM. This will be described below in more detail.

Figure 69:
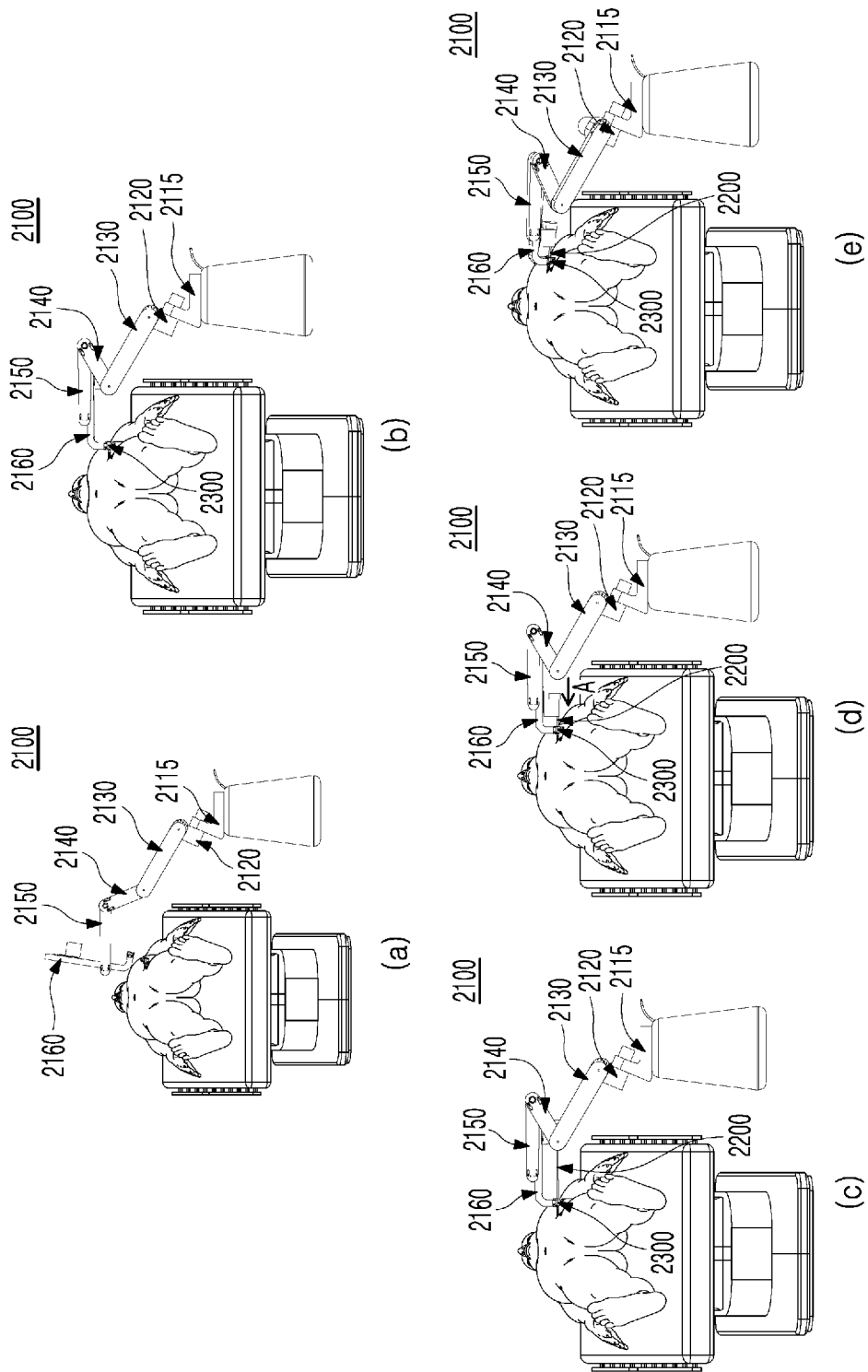
FIG. 69 is a view illustrating a surgical method performed by the surgical robot arm of the present disclosure.

First, as shown in FIG. 69A, the modular surgical robot arm 2100 is disposed on one side of a patient. In this case, the body 2110 of the modular surgical robot arm 2100 may be disposed adjacent to a patient's port (the position through which the trocar is inserted), on the same side as the patient's port based on the bed, rather than being located on the opposite side of the patient' port.

Next, as shown in FIG. 69B, the surgical robot arm 2100 is set to a horizontal (or at a predetermined angle similar to the horizontal) state. In this case, the links may be disposed to overlap each other by folding two or more links rather than having a plurality of links stretched out long.

Next, as shown in FIG. 69C, the surgical instrument 2100 is mounted on the fifth link 2160 of the surgical robot arm 2100. In this case, no components, such as links, are positioned between the surgical instrument 2200 and the patient. That is, as described above, the surgical robot arm 2100 may be configured such that when the surgical instrument 2200 is mounted on the fifth link 2160, the surgical instrument 2200 is positioned at the bottom of the fifth link 2160 rather than at the top thereof (i.e., positioned in a direction in which the links are positioned when all links are folded).

In other words, the surgical instrument 2200 coupled to the fifth link 2160 is disposed to face inwardly of the surgical robot arm 2100. That is, in a state in which the surgical instrument 2200 coupled to the fifth link 2160 is horizontal and the end tool 2210 thereof is disposed in a direction away from the body 2110, the fifth link 2160 is disposed such that a surface thereof to which the surgical instrument 2200 is coupled faces downward. In other words, the surgical instrument 2200 coupled to one surface of the fifth link 2160 is disposed below the fifth link 2160.

With this configuration, even when the modular surgical robot arm 2100 is horizontally positioned in a state of being disposed adjacent to the patient' port, the fifth link 2160, on which the surgical instrument 2200 is mounted, is prevented from coming into direct contact with the patient, thereby having the advantage of reducing vibration and improving rigidity.

Next, as shown in FIG. 69D, the surgical instrument 2200 mounted on the fifth link 2160 is linearly moved and the end tool of the surgical instrument 2200 is insert into the patient's body.

Next, as shown in FIG. 69E, the surgical robot arm 2100 performs a surgery while maintaining an RCM point.

As described above, in the present disclosure, by forming the first yaw axis Y1 and the extension line connecting the third joint 2173 to the RCM to be different from each other, and forming the extension line and the first yaw axis Y1 to intersect each other at the RCM, gimbal lock is prevented from occurring even in the most commonly used positioning of the surgical instrument, and as a result, the overall surgical robot configuration can be made more compact.

In addition, in the present disclosure, the surgical robot arm is formed in a modular manner, in which one surgical instrument is deployed from a body of one surgical robot arm, and a plurality of modular surgical robot arms, each equipped with one surgical instrument, are provided. In addition, each of these surgical robot arms is disposed in the vicinity of each of a plurality of ports of the patient, so that the overall length of the deployed surgical robot arms is shortened, thereby obtaining an effect of reducing vibration and increasing rigidity.

Furthermore, in the present disclosure, the fourth link 2150 and the fifth link 2160 are arranged side by side to be adjacent to each other (when viewed from the XY plane) so that the fourth link 2150 and the fifth link 2160 overlap each other (when viewed from the XZ plane), and thus, the rotational motion of the fourth link 2150 is not constrained by other links such as the fifth link 2160, thereby increasing the range of motion of the instrument, such as allowing a moving direction of the instrument to extend beyond the horizontal direction and face upward. Accordingly, even in the frequent case of surgery, in which the instrument is disposed in the horizontal direction, an effect of preventing the gimbal lock and allowing the instrument to move with a sufficient range of motion may be obtained.

Furthermore, in the present disclosure, the surface to which the surgical instrument 2200 is coupled is disposed to face downward in a state in which the surgical instrument is horizontally disposed, and no components such as links are positioned between the surgical instrument 2200 and the patient. With this configuration, in the surgical robot arm, vibration can be reduced and rigidity can be improved.

As described above, the present disclosure has been described with reference to the embodiments described with reference to the drawings, but it will be understood that this is merely exemplary, and those of ordinary skill in the art will understand that various modifications and variations of the embodiments are possible therefrom. Accordingly, the true technical protection scope of the present disclosure should be defined by the technical spirit of the appended claims.

INDUSTRIAL APPLICABILITY

The present disclosure relates to a surgical robot arm, and more particularly, may be used in a minimally invasive surgical robot arm that is formed in a modular manner for use in a laparoscopic surgery or other various surgeries.

The invention claimed is:

1. A surgical robot arm to which a surgical instrument is mounted, the surgical robot arm comprising:
   a body;
   a base link formed on one surface of the body;
   a yaw drive assembly coupled to the base link by a first joint and formed to be yaw rotatable around a first yaw axis with respect to the base link;
   a third link axially coupled to the yaw drive assembly so as to be rotatable around a third joint with respect to the yaw drive assembly;
   a fourth link axially coupled to the third link so as to be rotatable around a fourth joint with respect to the third link; and a fifth link axially coupled to the fourth link so as to be rotatable around a fifth joint with respect to the fourth link, and formed to allow the surgical instrument to be mounted thereto, wherein a remote center of motion (RCM) is formed at the remaining vertex of a parallelogram with the third joint, the fourth joint, and the fifth joint constituting vertices, and the first yaw axis and an extension line connecting the third joint to the RCM are formed to be different from each other.

2. The surgical robot arm of claim 1, wherein
the first yaw axis and the extension line connecting the third joint to the RCM are formed to form a predetermined angle rather than being parallel to each other.

3. The surgical robot arm of claim 1, wherein
the RCM is positioned on an extension line of the first yaw axis.

4. The surgical robot arm of claim 1, wherein
when the third link rotates around the third joint,
the third link and the fifth link rotate while maintaining a parallel state, and
the fourth link and the extension line connecting the third joint to the RCM rotate while maintaining a parallel state.

5. The surgical robot arm of claim 1, wherein
the RCM remains constant in position regardless of the rotation of the third link.

6. The surgical robot arm of claim 1, wherein
the third link and the fifth link maintain a parallel state in any state of motion of the surgical robot arm, and
the fourth link and the extension line connecting the third joint to the RCM maintain a parallel state in any state of motion of the surgical robot arm.

7. The surgical robot arm of claim 1, wherein
a height of the RCM in a Z-axis direction is formed to be greater than a height of a point of the base link, through which the first yaw axis passes, in the Z-axis direction.

8. The surgical robot arm of claim 1, wherein
the yaw drive assembly further includes:
a first link coupled to the base link by the first joint and formed to be yaw rotatable around the first yaw axis with respect to the base link;
a sixth link coupled to the first link by a sixth joint and formed to be yaw rotatable around a second yaw axis with respect to the first link; and
a second link having one end portion fixedly coupled to the sixth link and another end portion coupled to the third link.

9. The surgical robot arm of claim 8, wherein
the RCM is positioned on an extension line of the second yaw axis.

10. The surgical robot arm of claim 8, wherein
an extension line of the first yaw axis and an extension line of the second yaw axis intersect at the RCM.

11. The surgical robot arm of claim 8, wherein
the first link formed to be yaw rotatable around the first yaw axis and
the sixth link formed to be yaw rotatable around the second yaw axis are formed to be rotatable independently of each other.

12. The surgical robot arm of claim 8, wherein
when a roll axis of the surgical instrument is parallel to the first yaw axis, a yaw motion is performed by rotation of the second yaw axis.

13. The surgical robot arm of claim 8, wherein
when a roll axis of the surgical instrument is parallel to the second yaw axis, a yaw motion is performed by rotation of the first yaw axis.

14. The surgical robot arm of claim 1, wherein
the yaw drive assembly further includes:
a first link coupled to the base link by the first joint and formed to be yaw rotatable around the first yaw axis with respect to the base link; and
a second link having one end portion fixedly coupled to the first link and another end portion coupled to the third link.

15. The surgical robot arm of claim 14, wherein
the second link is formed parallel to the extension line connecting the third joint to the RCM.

16. The surgical robot arm of claim 14, wherein
the second link and the fourth link are formed parallel to each other.

17. The surgical robot arm of claim 14, wherein
the second link is formed to be inclined with respect to the extension line connecting the third joint to the RCM.

18. The surgical robot arm of claim 14, wherein
the second link the fourth link are formed to form a predetermined angle rather than being parallel to each other.

19. The surgical robot arm of claim 1, wherein
each of the third link, the fourth link, and the fifth link is formed to be offset by a certain degree in a direction of a rotation axis thereof.

20. The surgical robot arm of claim 1, wherein
based on a direction of a rotation axis of the third link, the fourth link is disposed on one side of the third link and the fifth link is disposed on one side of the fourth link.

21. The surgical robot arm of claim 1, wherein
based on a direction of the first yaw axis, at least a portion of each of the third link, the fourth link, and the fifth link overlap each other.

22. The surgical robot arm of claim 1, wherein
in a state in which the surgical instrument coupled to the fifth link is horizontal and an end tool of the surgical instrument is disposed in a direction away from the body,
a first surface of the fifth link, to which the surgical instrument is coupled, is disposed to face upward in a Z-axis direction.

23. The surgical robot arm of claim 22, wherein
in the state, the surgical instrument is disposed above the fifth link.

24. The surgical robot arm of claim 1, wherein
in a state in which the surgical instrument coupled to the fifth link is horizontal and an end tool of the surgical instrument is disposed in a direction away from the body,
a first surface of the fifth link, to which the surgical instrument is coupled, is disposed to face downward in a Z-axis direction.

25. The surgical robot arm of claim 24, wherein
in the state, the surgical instrument is disposed below the fifth link.

26. The surgical robot arm of claim 1, wherein
based on a plane perpendicular to a Z-axis, the first yaw axis and at least some of the third link, the fourth link, and the fifth link are formed to form a predetermined angle.

27. The surgical robot arm of claim 1, wherein
the first yaw axis and at least some of the third link, the fourth link, and the fifth link are formed parallel to each other.

28. The surgical robot arm of claim 1, wherein
a height of the first yaw axis in a Z-axis direction at a distal end is formed greater than a height of the first yaw axis in the Z-axis direction at a proximal end.

29. The surgical robot arm of claim 1, wherein
the base link is formed to be inclined at a predetermined angle with respect to the extension line connecting the third joint to the RCM, so that a central axis of the base link is formed to coincide with the first yaw axis.

30. The surgical robot arm of claim 1, wherein
the first yaw axis and the extension line connecting the third joint to the RCM intersect at the RCM.

* * * * *